(12) United States Patent
Cholli et al.

(10) Patent No.: US 11,578,285 B2
(45) Date of Patent: Feb. 14, 2023

(54) MACROMOLECULAR CORROSION (MCIN) INHIBITORS: STRUCTURES, METHODS OF MAKING AND USING THE SAME

(71) Applicant: Polnox Corporation, Lowell, MA (US)

(72) Inventors: Ashok L. Cholli, Lowell, MA (US); Murat Tonga, Lowell, MA (US)

(73) Assignee: Polnox Corporation, Lowell, MA (US)

( * ) Notice: Subject to any disclaimer, the term of this patent is extended or adjusted under 35 U.S.C. 154(b) by 0 days.

(21) Appl. No.: 17/094,457

(22) Filed: Nov. 10, 2020

(65) Prior Publication Data

US 2021/0130722 A1 May 6, 2021

Related U.S. Application Data

(63) Continuation of application No. 15/909,778, filed on Mar. 1, 2018, now abandoned.

(Continued)

(51) Int. Cl.
| | | |
|---|---|---|
| *C07F 5/04* | (2006.01) | |
| *C10M 105/36* | (2006.01) | |
| *C10L 10/04* | (2006.01) | |
| *C10M 129/72* | (2006.01) | |
| *C07C 69/604* | (2006.01) | |
| *C23F 11/12* | (2006.01) | |
| *C07C 67/08* | (2006.01) | |
| *C07C 67/14* | (2006.01) | |

(Continued)

(52) U.S. Cl.
CPC ............... *C10L 10/04* (2013.01); *A23D 7/00* (2013.01); *A23D 9/00* (2013.01); *C07C 67/08* (2013.01); *C07C 67/14* (2013.01); *C07C 69/604* (2013.01); *C10L 1/19* (2013.01); *C10L 1/1905* (2013.01); *C10L 1/1981* (2013.01); *C10M 129/72* (2013.01); *C10M 169/04* (2013.01); *C10M 169/041* (2013.01); *C11C 3/003* (2013.01); *C11D 3/0073* (2013.01); *C23F 11/128* (2013.01); *C10L 1/1616* (2013.01); *C10L 1/1641* (2013.01); *C10L 1/1802* (2013.01); *C10L 1/191* (2013.01); *C10L 1/1983* (2013.01); *C10L 1/1985* (2013.01); *C10L 2200/0423* (2013.01); *C10L 2200/0446* (2013.01); *C10L 2200/0469* (2013.01); *C10L 2200/0476* (2013.01); *C10L 2200/0484* (2013.01); *C10M 2203/1006* (2013.01); *C10M 2203/1025* (2013.01); *C10M 2205/0285* (2013.01); *C10M 2207/28* (2013.01); *C10M 2207/282* (2013.01); *C10M 2207/288* (2013.01); *C10M 2207/2835* (2013.01); *C10M 2207/401* (2013.01); *C10M 2209/101* (2013.01); *C10M 2209/1023* (2013.01); *C10M 2209/1033* (2013.01); *C10N 2020/02* (2013.01); *C10N 2030/12* (2013.01); *C10N 2030/24* (2020.05); *C10N 2030/64* (2020.05)

(58) Field of Classification Search
CPC .......... C10L 10/04; C10L 1/19; C10L 1/1905; C10L 1/1981; C10L 1/1616; C10L 1/1641; C10L 1/1802; C10L 1/191; C10L 1/1983; C10L 1/1985; C10L 2200/0423; C10L 2200/0446; C10L 2200/0469; C10L 2200/0476; C10L 2200/0484; A23D 7/00; A23D 9/00; C07C 67/08; C07C 67/14; C07C 69/604; C10M 129/72; C10M 169/04; C10M 169/041; C10M 2203/1006; C10M 2203/1025; C10M 2205/0285; C10M 2207/28; C10M 2207/282; C10M 2207/2835; C10M 2207/288; C10M 2207/401; C10M 2209/101; C10M 2209/1023; C10M 2209/1033; C11C 3/003; C11D 3/0073; C23F 11/128; C10N 2020/02; C10N 2030/12; C10N 2030/24; C10N 2030/64
USPC .................................................. 508/496, 200
See application file for complete search history.

(56) References Cited

U.S. PATENT DOCUMENTS

| | | |
|---|---|---|
| 2,467,358 A | 4/1949 | Neumann |
| 3,116,305 A | 12/1963 | Morris et al. |

(Continued)

FOREIGN PATENT DOCUMENTS

| | | |
|---|---|---|
| CZ | 111291 A | 4/1908 |
| DE | 19747644 A1 | 5/1999 |

(Continued)

OTHER PUBLICATIONS

Akkara et al., "Hematin-catalyzed polymerization of phenol compounds," Macromolecules, 33(7):2377-2382 (2000).

(Continued)

*Primary Examiner* — Prem C Singh
*Assistant Examiner* — Francis C Campanell
(74) *Attorney, Agent, or Firm* — Foley Hoag LLP; N. Scott Pierce

(57) ABSTRACT

Disclosed are multifunctional compounds represented by structural formula (I):

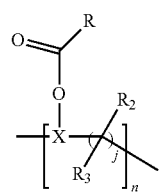

(Continued)

methods of producing compounds represented by structural formula (I) and their use in inhibiting corrosion in corrodible material.

14 Claims, No Drawings

Related U.S. Application Data

(60) Provisional application No. 62/465,666, filed on Mar. 1, 2017.

(51) Int. Cl.
| | | |
|---|---|---|
| *C10M 169/04* | (2006.01) | |
| *C10L 1/198* | (2006.01) | |
| *C10L 1/19* | (2006.01) | |
| *C11D 3/00* | (2006.01) | |
| *A23D 7/00* | (2006.01) | |
| *A23D 9/00* | (2006.01) | |
| *C11C 3/00* | (2006.01) | |
| *C10L 1/16* | (2006.01) | |
| *C10L 1/18* | (2006.01) | |
| *C10N 20/02* | (2006.01) | |
| *C10N 30/12* | (2006.01) | |
| *C10N 30/00* | (2006.01) | |

(56) References Cited

U.S. PATENT DOCUMENTS

| | | |
|---|---|---|
| 3,294,836 A | 12/1966 | Peterson et al. |
| 3,441,545 A | 4/1969 | Blatz et al. |
| 3,459,704 A | 8/1969 | Peterson et al. |
| 3,557,245 A | 1/1971 | Phillips et al. |
| 3,632,785 A | 1/1972 | Bornstein |
| 3,645,970 A | 2/1972 | Kleiner |
| 3,649,667 A | 3/1972 | Song et al. |
| 3,655,831 A | 4/1972 | Friedman |
| 3,870,680 A | 3/1975 | Schurdak |
| 3,907,939 A | 9/1975 | Robin et al. |
| 3,936,479 A | 2/1976 | Avar et al. |
| 3,953,402 A | 4/1976 | Kline |
| 3,965,039 A | 6/1976 | Chaplits et al. |
| 3,983,091 A | 9/1976 | Gloth et al. |
| 3,994,828 A | 11/1976 | Zaffaroni |
| 3,996,160 A | 12/1976 | Dale et al. |
| 3,996,198 A | 12/1976 | Wang et al. |
| 4,054,676 A | 10/1977 | Weinshenker et al. |
| 4,094,857 A | 6/1978 | Wolfe, Jr. |
| 4,096,319 A | 6/1978 | Willette et al. |
| 4,097,464 A | 6/1978 | Kline |
| 4,098,829 A | 7/1978 | Weinshenker et al. |
| 4,107,144 A | 8/1978 | Russell et al. |
| 4,136,055 A | 1/1979 | Lyons |
| 4,202,816 A | 5/1980 | Moser et al. |
| 4,205,151 A | 5/1980 | Dale et al. |
| 4,213,892 A | 7/1980 | Scott |
| 4,219,453 A | 8/1980 | Sakurai et al. |
| 4,267,358 A | 5/1981 | Hechenbleikner et al. |
| 4,281,192 A | 7/1981 | Jacquet et al. |
| 4,283,572 A | 8/1981 | Klicker |
| 4,317,933 A | 3/1982 | Parker |
| 4,341,879 A | 7/1982 | Sugio et al. |
| 4,355,148 A | 10/1982 | Layer et al. |
| 4,377,666 A | 3/1983 | Farrar |
| 4,380,554 A | 4/1983 | Serres, Jr. |
| 4,447,657 A | 5/1984 | Firth et al. |
| 4,465,871 A | 8/1984 | Firth et al. |
| 4,480,108 A | 10/1984 | Foster |
| 4,510,296 A | 4/1985 | Hergenrother |
| 4,511,491 A | 4/1985 | Ishii et al. |
| 4,634,728 A | 1/1987 | Dunski et al. |
| 4,690,995 A | 9/1987 | Key et al. |
| 4,761,247 A | 8/1988 | Rei et al. |
| 4,788,282 A | 11/1988 | Deziel |
| 4,824,929 A | 4/1989 | Arimatsu et al. |
| 4,849,503 A | 7/1989 | Cotter et al. |
| 4,855,345 A | 8/1989 | Rosenberger et al. |
| 4,857,596 A | 8/1989 | MacLeay et al. |
| 4,859,736 A | 8/1989 | Rink |
| 4,870,214 A | 9/1989 | Mina et al. |
| 4,894,263 A | 1/1990 | Dubois et al. |
| 4,897,438 A | 1/1990 | Kikuchi et al. |
| 4,900,671 A | 2/1990 | Pokora et al. |
| 4,925,591 A | 5/1990 | Nakauchi et al. |
| 4,968,759 A | 11/1990 | Kikuchi et al. |
| 4,977,004 A | 12/1990 | Bettie, III et al. |
| 4,978,739 A | 12/1990 | Arnone et al. |
| 4,981,917 A | 1/1991 | MacLeay et al. |
| 4,994,628 A | 2/1991 | Goddard et al. |
| 5,004,781 A | 4/1991 | Rink |
| 5,013,470 A | 5/1991 | Benfaremo |
| 5,017,727 A | 5/1991 | Olivier |
| 5,082,358 A | 1/1992 | Tabata et al. |
| 5,102,962 A | 4/1992 | Kikuchi et al. |
| 5,117,063 A | 5/1992 | Stern et al. |
| 5,143,828 A | 9/1992 | Akkara et al. |
| 5,153,298 A | 10/1992 | Pokora et al. |
| 5,155,153 A | 10/1992 | Neri et al. |
| 5,185,391 A | 2/1993 | Stokich, Jr. |
| 5,185,407 A | 2/1993 | Wong |
| 5,188,953 A | 2/1993 | Johnson et al. |
| 5,191,008 A | 3/1993 | Frost et al. |
| 5,196,142 A | 3/1993 | Mollet et al. |
| 5,206,303 A | 4/1993 | Tse et al. |
| 5,207,939 A | 5/1993 | Farng et al. |
| 5,212,044 A | 5/1993 | Liang et al. |
| 5,274,060 A | 12/1993 | Schadeli |
| 5,278,055 A | 1/1994 | Cyrus, Jr. et al. |
| 5,304,589 A | 4/1994 | Davidson et al. |
| 5,320,889 A | 6/1994 | Bettie, III |
| 5,444,143 A | 8/1995 | Ohta et al. |
| 5,449,715 A | 9/1995 | Plochocka et al. |
| 5,498,809 A | 3/1996 | Emert et al. |
| RE35,247 E | 5/1996 | Cyrus, Jr. et al. |
| 5,516,856 A | 5/1996 | Sanchez |
| 5,541,091 A | 7/1996 | Wheeler et al. |
| 5,565,300 A | 10/1996 | Uenishi et al. |
| 5,574,118 A | 11/1996 | Olivier |
| 5,652,201 A | 7/1997 | Papay et al. |
| 5,739,341 A | 4/1998 | Dubs et al. |
| 5,834,544 A | 11/1998 | Lin et al. |
| 5,837,798 A | 11/1998 | Hutchings et al. |
| 5,869,592 A | 2/1999 | Gagne et al. |
| 5,911,937 A | 6/1999 | Hekal |
| 5,994,498 A | 11/1999 | Tripathy et al. |
| 6,018,018 A | 1/2000 | Samuelson et al. |
| 6,028,131 A | 2/2000 | Meier et al. |
| 6,040,111 A | 3/2000 | Karasawa et al. |
| 6,046,263 A | 4/2000 | Rasberger et al. |
| 6,096,695 A | 8/2000 | Lam et al. |
| 6,096,859 A | 8/2000 | Akkara et al. |
| 6,150,491 A | 11/2000 | Akkara |
| 6,232,101 B1 | 5/2001 | Budolfsen et al. |
| 6,232,314 B1 | 5/2001 | Jarrott et al. |
| 6,242,010 B1 | 6/2001 | Hersh |
| 6,306,991 B1 | 10/2001 | Fischer et al. |
| 6,342,549 B1 | 1/2002 | Hirose et al. |
| 6,444,450 B2 | 9/2002 | Akkara et al. |
| 6,537,546 B2 | 3/2003 | Echigo et al. |
| 6,569,651 B1 | 5/2003 | Samuelson et al. |
| 6,646,035 B2 | 11/2003 | Koch et al. |
| 6,723,815 B2 | 4/2004 | Callaghan et al. |
| 6,743,525 B2 | 6/2004 | Berntsen et al. |
| 6,770,785 B1 | 8/2004 | Desai et al. |
| 6,794,480 B2 | 9/2004 | Goto et al. |
| 6,800,228 B1 | 10/2004 | Semen |
| 6,828,364 B2 | 12/2004 | Gugumus |
| 6,846,859 B2 | 1/2005 | Coffy et al. |
| 6,933,319 B2 | 8/2005 | Browning et al. |
| 7,087,799 B2 | 8/2006 | Tsuihiji et al. |
| 7,132,496 B2 | 11/2006 | Kerres et al. |

(56) References Cited

U.S. PATENT DOCUMENTS

| | | |
|---|---|---|
| 7,169,844 B2 | 1/2007 | Inokami |
| 7,205,350 B2 | 4/2007 | Thibaut |
| 7,223,432 B2 | 5/2007 | Cholli et al. |
| 7,262,319 B2 | 8/2007 | Rehm et al. |
| 7,323,511 B2 | 1/2008 | Cholli et al. |
| 7,507,454 B2 | 3/2009 | Cholli et al. |
| 7,595,074 B2 | 9/2009 | Cholli et al. |
| 7,601,378 B2 | 10/2009 | Cholli et al. |
| 7,678,877 B2 | 3/2010 | Yang et al. |
| 7,705,075 B2 | 4/2010 | Kumar et al. |
| 7,705,176 B2 | 4/2010 | Cholli et al. |
| 7,705,185 B2 | 4/2010 | Kumar et al. |
| 7,727,571 B2 | 6/2010 | Cholli et al. |
| 7,754,267 B2 | 7/2010 | Cholli et al. |
| 7,767,853 B2 | 8/2010 | Cholli et al. |
| 7,799,948 B2 | 9/2010 | Kumar et al. |
| 7,902,317 B2 | 3/2011 | Kumar et al. |
| 7,923,587 B2 | 4/2011 | Cholli |
| 7,956,153 B2 | 6/2011 | Cholli et al. |
| 8,008,423 B2 | 8/2011 | Kumar et al. |
| 8,039,673 B2 | 10/2011 | Cholli et al. |
| 8,080,689 B2 | 12/2011 | Kumar |
| 8,242,230 B2 | 8/2012 | Cholli et al. |
| 8,252,884 B2 | 8/2012 | Kumar et al. |
| 8,481,670 B2 | 7/2013 | Kumar et al. |
| 8,598,382 B2 | 12/2013 | Cholli et al. |
| 8,691,933 B2 | 4/2014 | Kumar et al. |
| 8,710,266 B2 | 4/2014 | Kumar et al. |
| 8,846,847 B2 | 9/2014 | Cholli et al. |
| 8,927,472 B2 | 1/2015 | Cholli et al. |
| 9,193,675 B2 | 11/2015 | Cholli et al. |
| 9,388,120 B2 | 7/2016 | Kumar et al. |
| 9,523,060 B2 | 12/2016 | Cholli et al. |
| 9,950,990 B2 | 4/2018 | Cholli et al. |
| 10,294,423 B2 | 5/2019 | Cholli et al. |
| 10,683,455 B2 | 6/2020 | Cholli et al. |
| 11,060,027 B2 | 7/2021 | Cholli et al. |
| 2001/0041203 A1 | 11/2001 | Uno et al. |
| 2002/0007020 A1 | 1/2002 | Higashimura et al. |
| 2002/0049166 A1 | 4/2002 | Romanczyk et al. |
| 2002/0128493 A1 | 9/2002 | Romanczyk, Jr. et al. |
| 2002/0143025 A1 | 10/2002 | Pratt et al. |
| 2002/0183470 A1 | 12/2002 | Tripathy et al. |
| 2003/0030033 A1 | 2/2003 | Duyck et al. |
| 2003/0078346 A1 | 4/2003 | Nakamura et al. |
| 2003/0091837 A1 | 5/2003 | Aoki |
| 2003/0176620 A1 | 9/2003 | Romanczyk, Jr. et al. |
| 2003/0191242 A1 | 10/2003 | Zedda et al. |
| 2003/0229196 A1 | 12/2003 | Braat et al. |
| 2003/0230743 A1 | 12/2003 | Cholli et al. |
| 2004/0015021 A1 | 1/2004 | Adams et al. |
| 2004/0063783 A1 | 4/2004 | Lardy et al. |
| 2004/0164279 A1 | 8/2004 | Stevenson et al. |
| 2004/0171787 A1 | 9/2004 | Shim |
| 2004/0180994 A1 | 9/2004 | Pearson et al. |
| 2004/0186167 A1 | 9/2004 | Dou et al. |
| 2004/0186214 A1 | 9/2004 | Li et al. |
| 2004/0198875 A1 | 10/2004 | Kaprinidis et al. |
| 2004/0214935 A1 | 10/2004 | Cholli et al. |
| 2004/0260114 A1 | 12/2004 | Lee et al. |
| 2005/0170978 A1 | 8/2005 | Migdal et al. |
| 2005/0209379 A1 | 9/2005 | Botkin et al. |
| 2005/0238789 A1 | 10/2005 | Cholli et al. |
| 2005/0242328 A1 | 11/2005 | Baranski |
| 2006/0029706 A1 | 2/2006 | Cholli et al. |
| 2006/0040833 A1 | 2/2006 | Al-Akhdar et al. |
| 2006/0041087 A1 | 2/2006 | Cholli |
| 2006/0041094 A1 | 2/2006 | Cholli |
| 2006/0128929 A1 | 6/2006 | Yang et al. |
| 2006/0128930 A1 | 6/2006 | Dhawan et al. |
| 2006/0128931 A1 | 6/2006 | Kumar et al. |
| 2006/0128939 A1 | 6/2006 | Kumar et al. |
| 2006/0154818 A1 | 7/2006 | Destro et al. |
| 2006/0189820 A1 | 8/2006 | Rehm et al. |
| 2006/0189824 A1 | 8/2006 | Kumar et al. |
| 2006/0208227 A1 | 9/2006 | Shiraki |
| 2006/0233741 A1 | 10/2006 | Kumar et al. |
| 2007/0010632 A1 | 1/2007 | Kaplan et al. |
| 2007/0106059 A1 | 5/2007 | Cholli et al. |
| 2007/0135539 A1 | 6/2007 | Cholli et al. |
| 2007/0149660 A1 | 6/2007 | Kumar et al. |
| 2007/0154430 A1 | 7/2007 | Cholli et al. |
| 2007/0154608 A1 | 7/2007 | Cholli et al. |
| 2007/0154720 A1 | 7/2007 | Cholli et al. |
| 2007/0161522 A1 | 7/2007 | Cholli et al. |
| 2008/0249335 A1 | 10/2008 | Cholli et al. |
| 2008/0293856 A1 | 11/2008 | Kumar et al. |
| 2008/0311065 A1 | 12/2008 | Cholli |
| 2009/0184294 A1 | 7/2009 | Cholli et al. |
| 2010/0084607 A1 | 4/2010 | Cholli et al. |
| 2011/0040125 A1 | 2/2011 | Kumar et al. |
| 2011/0282098 A1 | 11/2011 | Cholli et al. |
| 2012/0004150 A1 | 1/2012 | Cholli et al. |
| 2012/0071596 A1 | 3/2012 | Kumar et al. |
| 2012/0123145 A1 | 5/2012 | Cholli et al. |
| 2012/0142968 A1 | 6/2012 | Kumar et al. |
| 2013/0041171 A1 | 2/2013 | Cholli et al. |
| 2013/0072586 A1 | 3/2013 | Kumar et al. |
| 2013/0130955 A1 | 5/2013 | Cholli et al. |
| 2013/0327594 A1* | 12/2013 | Raczkowski ........ C10M 133/18 184/6 |
| 2014/0011901 A1 | 1/2014 | Kumar et al. |
| 2014/0014880 A1 | 1/2014 | Cholli et al. |
| 2014/0316163 A1 | 10/2014 | Kumar et al. |
| 2015/0159109 A1 | 6/2015 | Cholli et al. |
| 2016/0115117 A1 | 4/2016 | Cholli et al. |
| 2016/0289558 A1 | 10/2016 | Cholli et al. |
| 2018/0251695 A1 | 9/2018 | Cholli et al. |
| 2020/0392406 A1 | 12/2020 | Cholli et al. |

FOREIGN PATENT DOCUMENTS

| | | |
|---|---|---|
| DE | 19843875 A1 | 3/2000 |
| EP | 01/48057 A2 | 7/1985 |
| EP | 0181023 A1 | 5/1986 |
| EP | 0289077 A2 | 11/1988 |
| EP | 0358157 A1 | 3/1990 |
| EP | 0404039 A1 | 12/1990 |
| EP | 0618203 A1 | 10/1994 |
| EP | 0688805 A1 | 12/1995 |
| EP | 1067144 A1 | 1/2001 |
| EP | 1468968 A1 | 10/2004 |
| FR | 2183973 A1 | 12/1973 |
| GB | 1042639 A | 9/1966 |
| GB | 1283103 A | 7/1972 |
| GB | 1320169 A | 6/1973 |
| GB | 1372042 A | 10/1974 |
| GB | 1389442 A | 4/1975 |
| GB | 1469245 A | 4/1977 |
| GB | 1482649 A | 8/1977 |
| JP | 69002715 | 1/1966 |
| JP | 43016392 | 7/1968 |
| JP | 43018453 | 8/1968 |
| JP | 44024274 | 10/1969 |
| JP | 44028850 | 11/1969 |
| JP | 57085366 | 5/1982 |
| JP | 59025814 | 2/1984 |
| JP | 59197447 | 11/1984 |
| JP | 60199832 | 10/1985 |
| JP | 62249945 A | 4/1986 |
| JP | H0452980 A | 2/1992 |
| JP | H05199858 A | 8/1993 |
| JP | H06135876 A | 5/1994 |
| JP | H06247959 A | 9/1994 |
| JP | H08027226 A | 1/1996 |
| JP | H09262069 A | 10/1997 |
| JP | 9322784 | 12/1997 |
| JP | H09309519 A | 12/1997 |
| JP | H09328521 A | 12/1997 |
| JP | H1180063 A | 3/1999 |
| JP | H11158103 A | 6/1999 |
| JP | 2003138258 A | 5/2003 |
| JP | 4929339 B2 | 5/2012 |
| NL | 7905000 A | 3/1980 |

(56) References Cited

FOREIGN PATENT DOCUMENTS

| | | |
|---|---|---|
| WO | WO-92/20734 A1 | 11/1992 |
| WO | WO-1997/14678 A1 | 4/1997 |
| WO | WO-00/39064 A1 | 7/2000 |
| WO | WO-01/18125 A1 | 3/2001 |
| WO | WO-01/48057 A1 | 7/2001 |
| WO | WO-02/28820 A1 | 4/2002 |
| WO | WO-02/079130 A1 | 10/2002 |
| WO | WO-2003/087260 A1 | 10/2003 |
| WO | WO-03/102004 A1 | 12/2003 |
| WO | WO-2004/024070 A2 | 3/2004 |
| WO | WO-2004/050795 A2 | 6/2004 |
| WO | WO-2005/025513 A2 | 3/2005 |
| WO | WO-2005/025646 A2 | 3/2005 |
| WO | WO-2005/060500 A2 | 7/2005 |
| WO | WO-2005/070974 A2 | 8/2005 |
| WO | WO-2005/071005 A1 | 8/2005 |
| WO | WO-2006/018403 A1 | 2/2006 |
| WO | WO-2006/014674 A3 | 4/2006 |
| WO | WO-2006/014605 A3 | 5/2006 |
| WO | WO-2006/060800 A1 | 6/2006 |
| WO | WO-2006/060801 A2 | 6/2006 |
| WO | WO-2006/060802 A1 | 6/2006 |
| WO | WO-2006/091705 A2 | 8/2006 |
| WO | WO-2006/104957 A2 | 10/2006 |
| WO | WO-2006/060803 A3 | 1/2007 |
| WO | WO-2007/050985 A2 | 5/2007 |
| WO | WO-2007/050987 A2 | 5/2007 |
| WO | WO-2007/050991 A1 | 5/2007 |
| WO | WO-2007/064843 A1 | 6/2007 |
| WO | WO-2008/005358 A2 | 1/2008 |
| WO | WO-2009/139005 A1 | 11/2009 |
| WO | WO-2015/077635 A2 | 5/2015 |
| WO | WO-2018/160879 A2 | 9/2018 |

OTHER PUBLICATIONS

Akkara et al., "Synthesis and characterization of polymers produced by horseradish peroxidase in dioxane," J of Polymer Science: Part A: Polymer Chemistry, 29(11):1561-1574 (1991).

Al-Malaika and Suharty, "Reactive processing of polymers: mechanisms of grafting reactions of functional antioxidants on polyolefins in the presence of a coagent," Polymer Degradation and Stability, 49:77-89 (1995).

Armengol et al., "Acid zeolites as catalysts in organic reactions, tert-butylation of anthracene, naphthalene and thianthrene," Appl Catal, A 149:411-423 (1997).

Ayyagari et al., "Controlled free-radical polymerization of phenol derivatices by enzyme-catalyzed reactions in organic solvents," Macromolecules, 28(15):5192-5197 (1995).

Badamali et al., "Influence of aluminium sources on the synthesis and catalytic activity of mesoporous AIMCM-41 molecular sieves," Catal Today, 63:291-295 (2000).

Belyaev et al., "Structure-activity relationship of diaryl phosphonate esters as potent irreversible dipeptidyl peptidase IV inhibitors," J Med Chem, 42:1041-1052 (1999).

Blokhin et al., "Phosphorylation of dihydric phenols with amides of phosphorous acid," Russian Chem Bulletin, 45(9):2250-2251 (1996).

Bruno et al., "Enzymatic template synthesis of polyphenol," Materials Research Society Symposium Proceedings, 600(EAO):255-259 (1999).

CAS Database No. XP002781515 (1968).

CAS Database XP-002387095, No. 1981:572206.

CAS Database XP-002429584, No. 81:153647, (1974).

Chandra and Sharma, "Alkylation of phenol with MTBE and other tertbutylethers: Cation exchange resins as catalysts," Catal Lett, 19(4):309-317 (1993).

Ciric-Marjanovic et al., "Chemical Oxidative Polymerization of Aminodiphenylamines," Journal of Physical Chemistry B, 112(23):6976-6987 (2008).

Coppinger et al., "Photo-fries rearrangement of aromatic esters. Role of steric and electronic factors," J of Phy Chem, 70(11):3479-3489 (1966).

Database Beilstein [online] Beilstein Institut Zur Forderung Der Chemischen Wissenschaften; XP002420027, Beilstein Registry No. 3517906.

Database Beilstein [online] Beilstein Institut Zur Forderung Der Chemischen Wissenschaften; XP002420028, Beilstein Registry No. 5840042.

Database Beilstein [online] Beilstein Institut Zur Forderung Der Chemischen Wissenschaften; XP002420029, Beilstein Registry No. 2311871.

Database Beilstein [online] Beilstein Institut Zur Forderung Der Chemischen Wissenschaften; XP002420030, Beilstein Registry No. 8876646.

Database Beilstein [online] Beilstein Institut Zur Forderung Der Chemischen Wissenschaften; XP002420031, Beilstein Registry No. 2271400.

Database Beilstein [online] Beilstein Institut Zur Forderung Der Chemischen Wissenschaften; XP002420032, Beilstein Registry No. 2212095.

Database Beilstein [online] Beilstein Institut Zur Forderung Der Chemischen Wissenschaften; XP002420033, Beilstein Registry No. 8941955.

Database Beilstein [online] Beilstein Institut Zur Forderung Der Chemischen Wissenschaften; XP002420034, Database Accession No. 2312425.

Database Beilstein [online] Beilstein Institut Zur Forderung Der Chemischen Wissenschaften; XP002420035, Beilstein Registry No. 905950.

Database Beilstein [online] Beilstein Institut Zur Forderung Der Chemischen Wissenschaften; XP002420036, Beilstein Registry No. 2140308.

Database Beilstein [online] Beilstein Institut Zur Forderung Der Chemischen Wissenschaften; XP002420037, Beilstein Registry No. 134886.

Database Beilstein [online] Beilstein Institut Zur Forderung Der Chemischen Wissenschaften; XP002420038, Beilstein Registry No. 1961007.

Devassy et al., "Zirconia supported phosphotungstic acid as an efficient catalyst for resorcinol tert-butylation and n-heptane hydroisomerization," J Mol Catalysis A: Chemical, 221:113-119 (2004).

Ding et al., "Chemical Trapping Experiments Support a Cation-Radical Mechanism for the Oxidative Polymerization of Aniline," Journal of Polymer Science, Part A: Polymer Chemistry, 37:2569-2579 (1999).

Dordick et al., "Polymerization of Phenols Catalyzed by Peroxidase in Nonaqueous Media," Biotechnology and Bioengineering, 30(1):31-36 (1987).

Dordick, "Enzymatic catalysis in monophasic organic dolvents," Enzyme Microb Technol, 11(4):194-211 (1989).

Faber, "Biotransformations in organic chemistry," A Textbook, Fourth Completely Revised and Extended Edition, 347-349 (1953).

FS&T 821 "Antioxidant,"http://class.fst.ohio-state.edu/fst/lect/aa.pdf, (Retrieved on Oct. 29, 2002).

FS&T 821 "Food Lipids," http://class.fst.ohio-state.edu/fst821/, (Retrieved on Oct. 29, 2002).

FST 821 "Course Schedule," http://class.fst.ohio-state.edu/fst821/, (Retrieved on Oct. 29, 2002).

Hatayama et al., "Anti-ulcer effect of isoprenyl flavonoids. III. 1) synthesis and anti-ulcer activity of metabolites of 2'-carboxymethoxyly-4,4'-bis(3-methyl-2-butenyloxy)chalcone2)," Chemical & Pharmaceutical Bulletin, 33(4):1327-1333 (1985).

Heidekum et al., "Nafion/Silica composite material reveals high catalytic potential in acylation reactions," J Catal, 188:230-232 (1999).

Hidalgo et al., "Antioxidant activity of depsides and sepsidones," Phytochemistry, 37(6)L1585-1587 (1994).

Hofer et al., "[[(Anilinooxalyl)amino]phenyl] phosphite stabilizers for polypropylene," Chemical Abstracts Service, 77:62780 (1972). http://www.machinerylubrication.com/Read/1028/Qxidation-Lubricant (Mar. 29, 2010, pp. 1-7).

Ikeda et al., "Novel synthetic pathway to a poly(phenylene oxide). Laccase-catalyzed oxidative polymerization of syringic acid," Macromolecules, 29:3053-3054 (1996).

(56) References Cited

OTHER PUBLICATIONS

International Search Report and Written Opinion for International Application No. PCT/US2018/020516 dated Sep. 9, 2018.
Irgafos 126 RTM., BASF publication, 1-3, (Jul. 2010).
Ismail and Wazzan, "Evaluation of new thermal stabilizers and antifatigue agents for rubber vulcanizates," Polymer-Plastics Tech and Eng, 45:751-758 (2006).
Jayaprakasha et al., "Antioxidant activity of grape seed (*Vitis vinifera*) extracts on peroxidation models in vitro," Food Chemistry, 73:285-290 (2001).
Jialanella and Pilrma, "Synthesis of poly(vinyl alcohol-co-vinyl gallate) by the chemical modification of poly(vinyl alcohol)," Polymer Bulletin, 18:385-389 (1987).
Joosens et al., "Diphenyl phosphonate inhibitors for the urokinase-type plasminogen activator: Optimization of the P4 position," J Med Chem, 49:5785-5793 (2006).
Kamalakar et al., "Influence of structural modification on lubricant properties of sal fat-based lubricant base stocks," Industrial Crops and products, 76(456-466 (2015).
Kamitori et al., "Silica gel as an effective catalyst for the alkylation of phenols and some heterocylic aromatic compounds," J Org Chem, 49:4161-4165 (1984).
Kammerer et al., "Der aufbau einiger homologer reihen von hydroxyphenylenmethylen-verbindungen und ihr schmelzverhalten," Die Makromolekulare Chemie, 169:1-13 (1973).
Kazandjian et al., "Enzymatic analses in organic solvents," Biotechnology and Bioengineering, XXVIII:417-421 (1986).
Khan et al., "An expedient esterification of aromatic carboxylic acids using sodium bromate and sodium hydrogen sulfite," Tetrahedron, 59(29):5549-5554 (2003).
Kim et al., "Melt free-radical grafting of hindered phenol antioxidant onto polyethylene," J Applied Polymer Science, 77:2968-2973 (2000).
Klibanov et al., "Enzymatic removal of toxic phenols and anilines from waste waters," J of Applied Biochemistry, 2(5):414-421 (1980).
Knobloch, "Ein neuer weg zu polymergebudenen alterungssjutzmittlen technologish einfach und effektiv a new way to polymer bound antioxidants technlogically simple and efficient," Kautschuk Und Gummi, Kutststiffe, Huthig, Verlag, Heidelberg, DE, 52(1):10-14 (1999).
Koshchii et al., "Alkylation of phenol by alcohols in the presence of aluminium phenolate," Org Chem, 24(7):1358-1361 (1988).
Kovalev et al., "Effectiveness of Inhibitors in the Oxidation of Jet Fuel With an Initiator," English Abstract, J. Neftekhimiya (Petroleum Chemistry), 21(2): 287-298 (1981).
Kovalev et al., "Study of the effectiveness of inhibitors in oxidation of jet fuel in a closed volume," English Abstract, Deposited Doc, VINITI:443-482 (1981).
Lalancette et al., "Metals intercalated in Graphite. II. The Friedel-crafts reactions with ALCL3-Graphite," Can J Chem, 52:589-591 (1974).
Li et al., "Novel multifunctional polymers," Chemical Reviews, 102(9):2925-2943 (2002).
Maki et al., "Weather-resistant colored polypropylene," Chemical Abstracts Service, 89:111364 (1978).
March, Advanced Organic Chemistry, McGraw Hill Book Company, New York, 251-259 (1977).
Masada and Oishi, "A new synthesis of aryl t-butul ethers," Chem Letters, 57-58 (1978).
Masada et al., "A new heterogeneous Williamson synthesis of ethers using t-allkyl substrates," The Chemical Society of Japan, 3:275-282 (1996).
Masada et al., "A new method for the williamson ether synthesis using t-allkyl halides in nonpolar solvents," The Chemical Society of Japan, 2:164-166 (1995).
Mehdipour-Ataei et al., "Novel Diols containing ester and amide groups and resulting poly(ester amide ester)s," J Applied Polymer Sci, 93:2699-2703 (2004).
Mejias et al., "New polymers from natural phenols using horseradish or soybean peroxidase," Macromol Biosci, 2:24-32 (2002).
Ol'dekop et al., "Simple synthesis of the tert-butyl ether of phenol," Inst Fiz-Org Khim, Zhurnal Obshchei Khimii, 50(2):475-476 (1980).
Orlando et al., "Elimination of acetic acid from protonated 4,5-diacetoxyphenanthrene and 2,2'-diacetoxybiphenyl: an example of an ion chemistry proximity effect," Organic Mass Spectrometry, 28(10):1184-1188 (1993).
Overgaag et al., "Rearrangement of alkyl phenyl ethers over dealuminated HY zeolites under liquid-phase conditions," Applied Catalysis A: General, 175(1-2):139-146 (1998).
Parmar et al., "Hydrolytic reactions on polyphenolic perpropanotes by porcine pancreatic lipase immobilized in microemulsion-based gels," 6(19):2269-2274 (1996).
Patoprsty et al., "13C NMR study of 3,9-Di(alkylphenoxy)-2,4,8,10-tetraoxa-3,9-diphosphaspiro[5.5]undecanes," Magnetic Resonance in Chem, 23(2):122-126 (1985).
Pirozhenko et al., "NMR study of topomerization of N-aroyl-p-benzoquinonemonoimines," Russian J of Organic Chem, 31(11):1514-1519 (1995).
Quaschning et al., "Propertoes of modified zirconia used as friedel-crafts-acylation catalysts," J Catal, 177:164-174 (1998).
RN 85660-63-1 (1984).
Ryu et al., "Peroxidase-catalyzed polymerization of phenols," Biocatalysis in agricultural biotechnology, Chapter 10:141-157 (1988).
Sakthivel et al., "Vapour phase tertiary butylation of phenol over sulfated zirconia catalyst," Catal Lett, 72(3-4):225-228 (2001).
Sartori et al., "Highly selective mono-tert-butylation of aromatic compounds," Chem Ind, 22:762-763 (1985).
Scharpe et al., "Serine peptidase modulators, their preparation, and their therapeutic use," Chemical Abstracts Service, ZCAPLUS, 131:223514 (1999).
Singh and Kaplan, "Biocatalytic route to ascorbic acid-modified polymers for free-radical scavenging," Adv Matter, 15(15):1291-1294 (2003).
Smith et al., "Development of chemical probes: Toward the mode of action of a methylene-linked di(aryl acetate) E1," Bioorganic & Medicinal Chemistry, 18(14):4917-4927 (2010).
Spano et al., "Substituted anilides of 3-monoethyl ester of 4-hydroxyisophthalic acid," Journal of Medicinal Chemistry, 15(5):552-553 (1987).
Thompson et al., "Stability of carotene in alfalfa meal: effect of antioxidants," Industrial and Engineering Chemistry, 42(5):922-925 (1950).
Tsvetkov et al., "Alkylation of phenols with higher olefins. Part I," Int Chem Eng, 7(1):104-121 (1967).
XP-002419239, "Discover Our World of Effects for Polyolefins," Ciba Speciality Chemicals, (2003).
Zinke et al., "Zur Kenntnis des Hartungsprozesses von Phenol-Formaldehyd-Harzen," Mh Chem, 89:135-142 (1958).

* cited by examiner

MACROMOLECULAR CORROSION (MCIN) INHIBITORS: STRUCTURES, METHODS OF MAKING AND USING THE SAME

RELATED APPLICATION

This application is a Continuation of U.S. application Ser. No. 15/909,778 filed on Mar. 1, 2018, which claims the benefit of U.S. Provisional Application 62/465,666 filed on Mar. 1, 2017. The entire teachings of the above application[s] are incorporated herein by reference.

GOVERNMENT SUPPORT

This invention was made with government support under IIP-1632258 from the National Science Foundation. The government has certain rights in the invention.

FIELD OF INVENTION

This invention relates newly developed multifunctional environmentally friendly macromolecular corrosion inhibitors utilize mainly the renewable and biobased raw material source. Most of the current corrosion inhibitors used in the industrial applications are not necessarily environmentally friendly and are based on petroleum based chemicals involving organic and inorganic species.

BACKGROUND OF THE INVENTION

This invention is directed to multifunctional macromolecular corrosion inhibitors and to fluid compositions containing minor amounts thereof. Multifunctional properties of this inhibitor include but not limited to rust inhibition, copper corrosion inhibition, and water and oil separating (demulsifier) capabilities. Fluids include but not limited to lubricants, biolubricants, bio-oils, bio-based oils, synthetic lubricants, fuels, bio-fuel, greases, bio-greases, aviation fuels, kerosene, gasoline, diesel, biodiesel, adhesives, and paints etc.

Corrosion in general terms is the degradation of a material caused by an aggressive environment such as water, air (oxygen), chemicals (acids, bases), organic liquids, oil, and gas, etc. Materials subject to corrosion include metals and their alloys, plastics, paints and coatings, concrete, or composites. Corrosion is a major concern in the durability of these materials, impacting safety, causing environmental damage, and incurring enormous repair and replacement costs. This is a major national concern. According to one United States federal government study in 2002, the total estimated cost of corrosion is a staggering $276 billion (approximately 3.1% of GDP) (Report FHWA-RD-01-156). If indirect costs are included, this increases to 6% of GDP ($552 billion), because of loss of productivity, delays, material failures, etc. It does not appear that newer studies exist. The direct effects of metal corrosion are (a) loss of mechanical strength and structural failure, (b) perforation of fluid transmission pipes, storage tanks, and ships, leading to leakage of harmful fluids into the environment, (c) contamination of fluid due to leaching of metal species from vessels' inner surfaces, (d) mechanical damage causing failure of structures, engines, pumps, and valves, and (e) events hazardous to human life due to excessive structural failure. Corrosion inhibitors play a key role in mitigating some of these corrosion issues. Corrosion inhibitors are typically added or treated (0.001% to 5%) to the corroding materials (metals, lubricants, fuels, plastics, oils and gas, adhesives, greases, paints and coating materials, cement, water reservoir, etc.) to protect against the corrosion from the surrounding environments like fluid, water, oxygen, moisture, weather, temperature, or their combinations, etc.

Environmental risks associated with corrosion inhibitors are forcing to seek more environmentally friendly products. Some products are also increasingly subject to restrictions by government agencies in the USA and other countries. These harmful substances can enter the environment directly when formulated fluids like lubricants come in contact with water, soil, or air, via leakage or spillage from industrial equipment, ships, automobiles, engines, earth-moving equipment, drilling, metal working fluids, hydropower plants, hydraulics and turbines (wind, water, steam, aviation), transformers, chain saw, gears, elevators, wire and ropes, two-stroke engines, etc. Corrosion inhibitors are added to fluids based on petroleum, synthetic and/or bio-oils, bio-based oils like lubricants, greases, adhesives, and fuels; and paints and coating materials. Thus, there is need to replace harmful compounds with environmentally-friendly and sustainable corrosion inhibitors without sacrificing performance. The present invention is a new material composition technology, Macromolecular Corrosion Inhibitors (McIn), described herein. McIn is envisioned as a disruptive technology that adds value to the supply chains of multiple market sectors.

BRIEF SUMMARY OF THE INVENTION

This invention is essentially directed to macromolecular corrosion inhibitors that are
  (a) the composition of polymers which are the reaction products of the starting materials comprising a substituted phenol and an aldehyde that is esterified further with an alkyl acid through oxalyl chloride or thionyl chloride or alkyl acids and using catalysts, if required to accelerate the esterification process,
  (b) the composition of polymers which are the reaction products of the starting materials comprising a substituted phenol and an aldehyde and are further reacted with an alkenyl succinic anhydride to form a half ester products having free carboxylic acid groups in the repeating units,
  (c) the composition of polymers which are the reaction products of the starting materials comprising a substituted phenol and an aldehyde and are further reacted with alkylene oxides (e.g. propylene oxide) to form phenol-derived alcohols in the repeating units,
  (d) the composition of polymers that are the reaction products of the starting materials of a substituted phenol and an aldehyde which are esterified further with oleic acid and then reacted with a maleic anhydride to form succinic anhydride adduct, and finally reacted with an alkyl alcohol to form a half ester product having free carboxylic acid groups in the repeating units,
  (e) the composition of reaction products derived from a maleic anhydride and an oleate which are the condensation products of oleic acid and alkyl alcohol that are further reacted with alkyl alcohol to form a half ester product having free carboxylic acid groups,
  (f) the composition of reaction products derived from a maleic anhydride and a substituted phenol-oleate further reacted with an alkyl alcohol to form a half ester product having free carboxylic acid groups. Substituted phenol-oleate is the condensation product of oleic acid and a substituted phenol, (g) the composition of reaction products of the starting materials comprising a substituted phenol and an alkylene oxides (e.g. propylene oxide) is further reacted with an alkenyl succinic anhydride to form a half ester product having free carboxylic acid groups, or (h) the composition of polymers which are the reaction products of the starting materials comprising a substituted phenol and an aldehyde and are further reacted with alkylene oxides (e.g. propylene oxide) to form phenol-derived alcohols in the repeating units, is further reacted with an alkenyl succinic anhydride to form a half ester product having free carboxylic acid groups, (i) the composition of polymers that are the reaction products of a substituted phenol and an aldehyde which are reacted with an alkylene oxide (e.g. propylene oxide) and then esterified further with an oleic acid and then reacted with a maleic anhydride to form succinic anhydride adduct, and finally reacted with an alkyl alcohol to form a half ester product having free carboxylic acid groups in the repeating units.

The present invention pertains to a compound represented by structural formula I and IA:

Structural Formula I

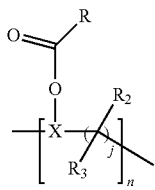

wherein:
X is:

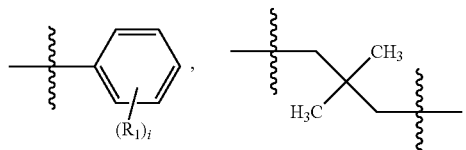

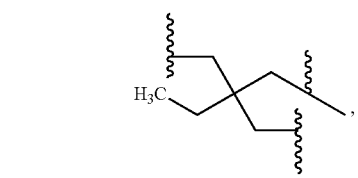

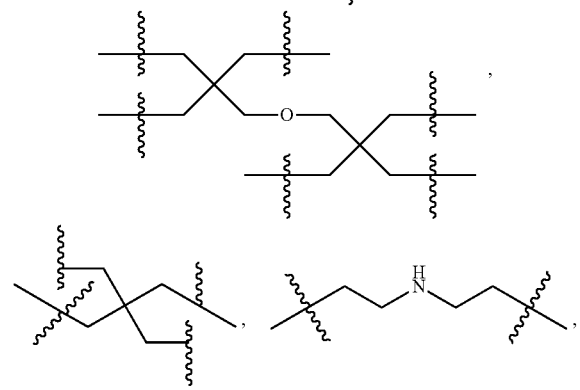

-continued

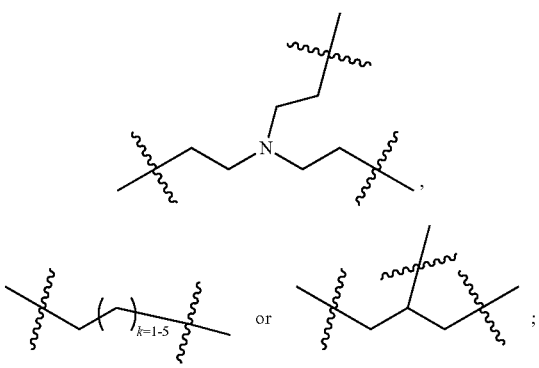

each $R_1$ is H, independently an optionally substituted $C_1$-$C_{20}$ alkyl group, an optionally substituted $C_1$-$C_{10}$ alkyl group, a tertiary carbon group, a methyl group, a methoxy group, an optionally substituted aryl group, and optionally substituted alkoxy group, an optionally substituted carbonyl group, an optionally substituted alkoxycarbonyl group, an optionally-CH(R''')(R'''COOH) wherein each R''' independently $C_1$-$C_{10}$ linear or branched alkyl chain, —OH, —SH or —NH$_2$ or an optionally substituted carbocyclic or heterocyclic non-aromatic ring;

i=0, 1, 2, 3;

j=0 or 1;

n is an integer from 1 to 1000, or an integer from 1 to 100, or an integer from 1 to 50, or an integer from 1 to 25, or an integer from 1 to 15, or preferably an integer from 1 to 10;

when n=1, then j=0;

when n>1 then j=1;

each $R_2$ and $R_3$ is independently H, a C1-C8 linear or branched or cyclic alkyl chain, an optionally substituted $C_1$-$C_{20}$ alkyl group, an optionally substituted $C_1$-$C_{10}$ alkyl group, a tertiary carbon group, a methyl group, a methoxy group, an optionally substituted aryl group, and optionally substituted alkoxy group, an optionally substituted carbonyl group, an optionally substituted alkoxycarbonyl group, or —CH(R''')(R'''COOH);

R is a $C_1$-$C_{24}$ linear or branched alkyl chain, alkenyl chain, or an isomerized structure or a mixture of isomerized (A) and (B):

(A)
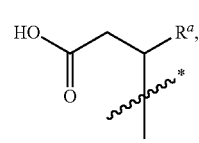

(B)
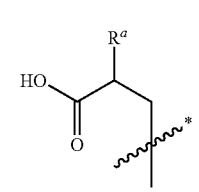

wherein $R^a$ is a $C_1$-$C_{24}$ alkenyl linear or branched chain, when n is 1 and j is 0, R in Structure I is a mixture of isomerized structures of

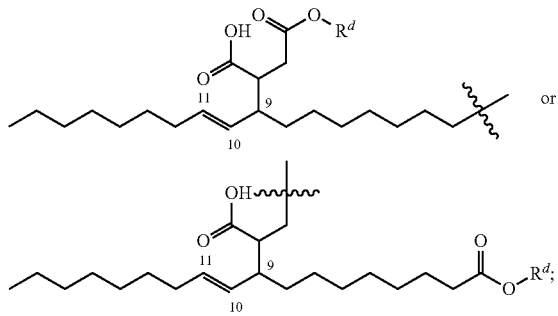

and $R^d$ is a C1-C24 linear or branched alkyl chain

DETAILED DESCRIPTION OF THE INVENTION

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e. to at least one) of the grammatical object of the article. By way of example, "an element" means one element or more than one element.

The terms "comprise" and "comprising" are used in the inclusive, open sense, meaning that additional elements may be included.

The term "including" is used herein to mean "including but not limited to". "Including" and "including but not limited to" are used interchangeably.

The term "polymer" is art-recognized and refers to a macromolecule comprising a repeating monomeric unit. The number of repeat units may vary as low as 2 and as high as million. In the present invention this number may vary from 2 to about 10,000, or less than 1,000, or less than about 100, or even less than about 10.

The term "monomer" is art-recognized and refers to a compound that is able to combine in long chains with other like or unlike molecules to produce.

The terms "number average molecular weight", or "Mn", "weight average molecular weight", "Z-average molecular weight" and "viscosity average molecular weight" are art-recognized. When the term "molecular weight" or an exemplary molecular weight is described herein, the measure of molecular weight will be clear from the context and/or will include all applicable measures.

"Small molecule" is an art-recognized term. In certain embodiments, this term refers to a molecule which has a molecular weight of less than about 2000 amu, or less than about 1000 amu, and even less than about 200 amu.

The term "aliphatic" is an art-recognized term and includes linear, branched, and cyclic alkanes, alkenes, or alkynes. In certain embodiments, aliphatic groups in the present invention are linear or branched and have from 1 to about 30 carbon atoms.

The term "alkyl" is art-recognized and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

The term "aralkyl" is art-recognized, and includes alkyl groups substituted with an aryl group (e.g., an aromatic or heteroaromatic group).

The terms "alkenyl" and "alkynyl" are art-recognized, and include unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to ten carbons, alternatively from one to about six carbon atoms in its backbone structure. Likewise, "lower alkenyl" and "lower alkynyl" have similar chain lengths.

The term "heteroatom" means nitrogen, oxygen, or sulfur and includes any oxidized form of nitrogen and sulfur and the quaternized form of any basic nitrogen. Also, the term "nitrogen" includes substitutable nitrogen of a heteroaryl or non-aromatic heterocyclic group. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR" (as in N-substituted pyrrolidinyl), wherein R" is a suitable substituent for the nitrogen atom in the ring of a non-aromatic nitrogen-containing heterocyclic group.

The term "aryl" is art-recognized, and includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" "heteroaryls," or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and apply to 1,2-, 1,3- and 1,4-disubstituted benzenes, respectively. For example, the names 1,2-dimethylbenzene and ortho-dimethylbenzene are synonymous.

The terms "heterocyclyl" and "heterocyclic group" are art-recognized, and include 3- to about 10-membered ring structures, such as 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" and "polycyclic group" are art-recognized, and include structures with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art recognized and includes an aromatic or non-aromatic ring in which each atom of the ring is carbon. The flowing art-recognized terms have the following meanings: "nitro" means —NO$_2$; the term "halogen" designates —F, —Cl, —Br or —I; the term "sulfhydryl" means —SH; the term "hydroxyl" means —OH; and the term "sulfonyl" means —SO$_2^-$.

The terms "amine" and "amino" are art-recognized and include both unsubstituted and substituted amines, e.g., a moiety that may be represented by the general formulas:

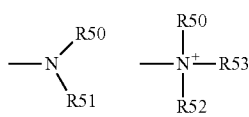

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and includes a moiety that may be represented by the general formula:

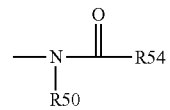

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

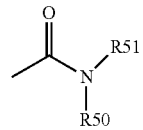

wherein R50 and R51 are as defined above. Certain embodiments of the amide in the present invention will not include imides which may be unstable.

The term "alkylthio" is art recognized and includes an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art recognized and includes such moieties as may be represented by the general formulas:

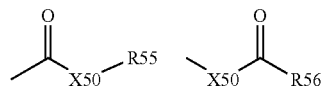

wherein X50 is a bond or represents an oxygen or a sulfur, and R55 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is oxygen and R55 or R56 is not hydrogen, the formula represents an "ester". Where X50 is oxygen, and R55 is as defined above, the moiety is referred to herein as a carboxyl group, and particularly when R55 is hydrogen, the formula represents a "carboxylic acid". Where X50 is an oxygen, and R56 is hydrogen, the formula represents a "formate". In general, where the oxygen atom of the above formula is replaced by sulfur, the formula represents a "thiocarbonyl" group. Where X50 is a sulfur and R55 or R56 is not hydrogen, the formula represents a "thioester." Where X50 is a sulfur and R55 is hydrogen, the formula represents a "thiocarboxylic acid." Where X50 is a sulfur and R56 is hydrogen, the formula represents a "thioformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art recognized and include an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and includes a moiety that may be represented by 290 the general formula:

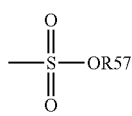

in which R57 is an electron pair, hydrogen, alkyl, cycloalkyl, or aryl.

The term "sulfate" is art recognized and includes a moiety that may be represented by the general formula:

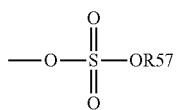

in which R57 is as defined above.

The term "sulfonamido" is art recognized and includes a moiety that may be represented by the general formula:

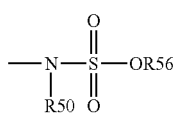

in which R50 and R56 are as defined above.

The term "sulfamoyl" is art-recognized and includes a moiety that may be represented by the general formula:

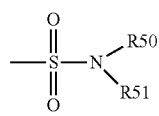

in which R50 and R51 are as defined above.

The term "sulfonyl" is art recognized and includes a moiety that may be represented by the general formula:

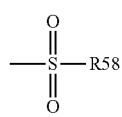

in which R58 is one of the following: hydrogen, alkyl, alkenyl, alkynyl, cycloalkyl, heterocyclyl, aryl or heteroaryl.

The term "sulfoxido" is art recognized and includes a moiety that may be represented by the general formula:

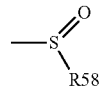

in which R58 is defined above.

The term "phosphoramidite" is art recognized and includes moieties represented by the general formulas:

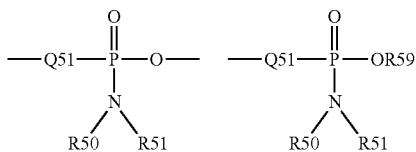

wherein Q51, R50, R51, and R59 are as defined above.

The term "phosphonamidite" is art recognized and includes moieties represented by the general formulas:

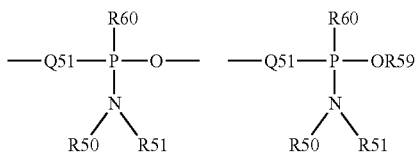

wherein Q51, R50, R51, and R59 are as defined above, and R60 represents a lower alkyl or an aryl.

As used herein the term non-aromatic carbocyclic ring as used alone or as part of a larger moiety refers to a non-aromatic carbon containing ring which can be saturated or unsaturated having three to fourteen atoms including monocyclic and polycyclic rings in which the carbocyclic ring can be fused to one or more non-aromatic carbocyclic or heterocyclic rings or one or more aromatic (carbocyclic or heterocyclic) rings.

An optionally substituted aryl group as defined herein may contain one or more substitutable ring atoms, such as carbon or nitrogen ring atoms. Examples of suitable substituents on a substitutable ring carbon atom of an aryl group include halogen (e.g., —Br, Cl, I and F), —OH, C1-C4 alkyl, C1-C4 haloalkyl, —NO$_2$, C1-C4 alkoxy, C1-C4 haloalkoxy, —CN, —NH$_2$, C1-C4 alkylamino, C1-C4 dialkylamino, —C(O)NH$_2$, —C(O)NH(C1-C4 alkyl), —C(O)(C1-C4 alkyl), —OC(O)(C1-C4 alkyl), —OC(O)(aryl), —OC(O)(substituted aryl), —OC(O)(aralkyl), —OC(O)(substituted aralkyl), —NHC(O)H, —NHC(O)(C1-C4 alkyl), —C(O)N(C1-C4 alkyl)$_2$, —NHC(O)O—(C1-C4 alkyl), —C(O)OH, —C(O)O—(C1-C4 alkyl), —NHC(O)NH$_2$, —NHC(O)NH(C1-C4 alkyl), —NHC(O)N(C1-C4 alkyl)$_2$, —NH—C(=NH)NH$_2$, —SO$_2$NH$_2$—SO$_2$NH(C1-C3alkyl), —SO$_2$N(C1-C3alkyl)$_2$, NHSO$_2$H, NHSO$_2$(C1-C4 alkyl) and optionally substituted aryl. Preferred substituents on aryl groups are as defined throughout the specification. In certain embodiments aryl groups are unsubstituted.

Examples of suitable substituents on a substitutable ring nitrogen atom of an aryl group include C1-C4 alkyl, NH$_2$, C1-C4 alkylamino, C1-C4 dialkylamino, —C(O)NH$_2$, —C(O)NH(C1-C4 alkyl), —C(O)(C1-C4 alkyl), —CO$_2$R, —C(O)C(O)R, —C(O)CH$_3$, —C(O)OH, —C(O)O—(C1-C4 alkyl), —SO$_2$NH$_2$—SO$_2$NH(C1-C3alkyl), —SO$_2$N(C1-C3alkyl)$_2$, NHSO$_2$H, NHSO$_2$(C1-C4 alkyl), —C(=S)NH$_2$, —C(=S)NH(C1-C4 alkyl), —C(=S)N(C1-C4 alkyl)$_2$, —C(=NH)—N(H)$_2$, —C(=NH)—NH(C1-C4 alkyl) and —C(=NH)—N(C1-C4 alkyl)$_2$, An optionally substituted alkyl group or non-aromatic carbocyclic or heterocyclic group as defined herein may contain one or more substituents. Examples of suitable substituents for an alkyl group include those listed above for a substitutable carbon of an aryl and the following: =O, =S, =NNHR, =NN(R)$_2$, =NNHC(O)R, =NNHCO$_2$ (alkyl), =NNHSO$_2$ (alkyl), =NR, spiro cycloalkyl group or fused cycloalkyl group. R** in each occurrence independently is —H or C1-C6 alkyl. Preferred substituents on alkyl groups are as defined throughout the specification. In certain embodiments optionally substituted alkyl groups are unsubstituted.

A "spiro cycloalkyl" group is a cycloalkyl group which shares one ring carbon atom with a carbon atom in an alkylene group or alkyl group, wherein the carbon atom being shared in the alkyl group is not a terminal carbon atom.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, etc., when it occurs more than once in any structure, is intended to be independent of its definition elsewhere in the same structure unless otherwise indicated expressly or by the context.

The term "selenoalkyl" is art recognized and includes an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R61, m, and R61 are defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to a trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms are art recognized and represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

The abbreviations OSA is for octenyl succinic anhydride, DDSA is for dodecenyl succinic anhydride, ODSA is for octadecenyl succinic anhydride, and PIMA is for polyisobutylene succinic anhydride preferably with low molecular weights (300-1500 molecular weight), and OASA is for oleic acid succinic anhydride.

The term an isomer is understood a molecule with the same molecular formula as another molecule, but with a different chemical structure. Isomers contain the same number of atoms of each element but have different arrangements of their atoms. Isomers do not necessarily share similar properties unless they also have the same functional groups. In structural isomers, sometimes referred to as constitutional isomers, the atoms, and functional groups are joined together in different ways. The chain isomers whereby hydrocarbon chains have variable amounts of branching; position isomers, which deals with the position of a functional group on a chain; and functional group isomerism, in which one functional group is split up into different ones. All such isomers, as well as mixtures thereof, are intended to be included in this invention.

Certain monomeric subunits of the present invention may exist in particular geometric or stereoisomeric forms. In addition, and other compositions of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986-87, inside cover. The term "hydrocarbon" is art recognized and includes all permissible compounds having at least one hydrogen and one carbon atom. For example, permissible hydrocarbons include acyclic and cyclic, branched and unbranched, carbocyclic and heterocyclic, aromatic and nonaromatic organic compounds that may be substituted or unsubstituted.

The phrase "protecting group" is art recognized and includes temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed. Greene et al., *Protective Groups in Organic Synthesis* 2$^{nd}$ ed., Wiley, New York, (1991).

The phrase "hydroxyl-protecting group" is art recognized and includes those groups intended to protect a hydroxyl group against undesirable reactions during synthetic procedures and includes, for example, benzyl or other suitable esters or ethers groups known in the art.

The term "electron-withdrawing group" is recognized in the art and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, March, *Advanced Organic Chemistry* 251-59, McGraw Hill Book Company, New York, (1977). The Hammett constant values are generally negative for electron donating groups (σ(P)=—0.66 for NH$_2$) and positive for electron withdrawing groups (σ(P)=0.78 for a nitro group), σ(P) indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

Contemplated equivalents of the or oligomers, subunits and other compositions described above include such materials which otherwise correspond thereto, and which have the same general properties thereof, wherein one or more simple variations of substituents are made which do not adversely affect the efficacy of such molecule to achieve its intended purpose of the present invention. In general, the methods of the present invention may be methods illustrated in the general reaction schemes as, for example, described below, or by modifications thereof, using readily available starting materials, reagents and conventional synthesis procedures. In these reactions, it is also possible to make use of variants which are in themselves known but are not mentioned here.

The present invention pertains to a compound represented by structural formula I:

Structural Formula I

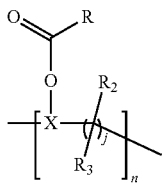

wherein:

X is:

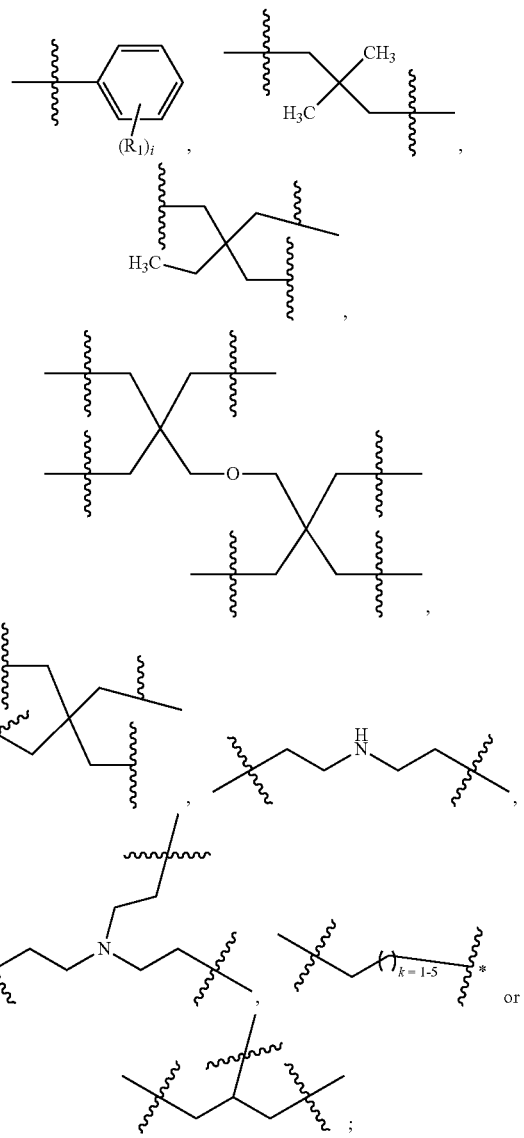

Each $R_1$ is H, independently an optionally substituted $C_1$-$C_{20}$ alkyl group, an optionally substituted $C_1$-$C_{10}$ alkyl group, a tertiary carbon group, a methyl group, a methoxy group, an optionally substituted aryl group, and optionally substituted alkoxy group, an optionally substituted carbonyl group, an optionally substituted alkoxycarbonyl group, an optionally-CH(R''') (R'''COOH) wherein each R''' independently $C_1$-$C_{10}$ linear or branched alkyl chain, —OH, —SH or —NH$_2$ or an optionally substituted carbocyclic or heterocyclic non-aromatic ring;

i=0, 1, 2, 3;

j=0 or 1;

n is an integer from 1 to 1000, or an integer from 1 to 100, or an integer from 1 to 50, or an integer from 1 to 25, or an integer from 1 to 15, or preferably an integer from 1 to 10;

when n=1, then j=0;

when n>1 then j=1;

each $R_2$ and $R_3$ is independently H, a C1-C8 linear or branched or cyclic alkyl chain, an optionally substituted $C_1$-$C_{20}$ alkyl group, an optionally substituted $C_1$-$C_{10}$ alkyl group, a tertiary carbon group, a methyl group, a methoxy group, an optionally substituted aryl group, and optionally substituted alkoxy group, an optionally substituted carbonyl group, an optionally substituted alkoxycarbonyl group, or —CH(R''')(R'''COOH);

R is a $C_1$-$C_{24}$ linear or branched alkyl chain, alkenyl chain, or an isomerized structure or a mixture of isomerized (A) and (B):

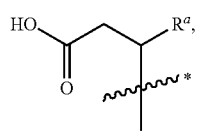

(A)

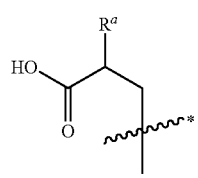

(B)

wherein $R^a$ is a $C_1$-$C_{24}$ alkenyl linear or branched chain.

In another embodiment, the present invention addresses that relate to a compound of Structure I wherein n=1;

j=0;

R is a mixture of isomerized structures of

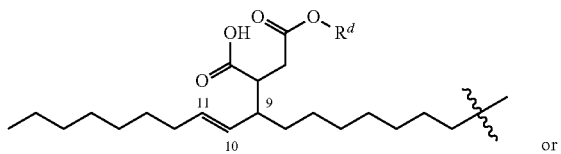

or

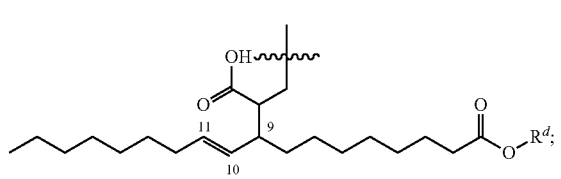

and $R^d$ is a $C_1$-$C_{24}$ linear or branched alkyl chain

In another embodiment, the present invention addresses that relate to a compound represented by structural formula II derived from Structural Formula I Structual Formula II

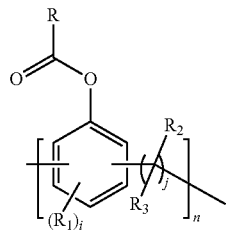

Each $R_1$ is H, independently an optionally substituted $C_1$-$C_{20}$ linear or branched alkyl group, a tertiary carbon group, a methyl group, a methoxy group, an optionally substituted aryl group, and an optionally substituted $C_1$-$C_{20}$ linear or branched alkoxy group, an optionally substituted carbonyl group, an optionally substituted $C_1$-$C_{20}$ linear or branched alkoxycarbonyl group, an optionally-CH(R''')(R'''COOH) wherein each R''' independently is $C_1$-$C_{10}$ linear or branched alkyl chain, —OH, —SH or —NH$_2$ or an optionally substituted carbocyclic or heterocyclic $C_1$-$C_{12}$ non-aromatic ring.

i=0 or 1 or 2 or 3;

j=0 or 1;

n is an integer from 1 to 1000 or 0 to 100, 0 to 50 or 0 to 25, 0 to 15, or preferably 0 to 10, when n=1, then j is always 0;

when n>1 then j is 1;

Each $R_2$, $R_3$, $R_4$ independently is H, methyl, or a $C_1$-$C_{24}$ linear or branched or cyclic alkyl chain.

Each $R_2$, $R_3$, $R_4$ is H, independently an optionally substituted $C_1$-$C_{24}$ alkyl group, an optionally substituted $C_1$-$C_{10}$ alkyl group, a tertiary carbon group, a methyl group, a methoxy group, an optionally substituted aryl group, and optionally substituted $C_1$-$C_{20}$ alkoxy group, an optionally substituted $C_1$-$C_{20}$ carbonyl group, an optionally substituted $C_1$-$C_{20}$ alkoxycarbonyl group, an optionally-CH(R''')(R'''COOH) wherein each R''' independently $C_1$-$C_{10}$ linear or branched alkyl chain, —OH, —SH or —NH$_2$ or an optionally substituted carbocyclic or heterocyclic $C_1$-$C_{12}$ non-aromatic ring.

R is a $C_1$-$C_{24}$ linear or branched alkyl chain, $C_1$-$C_{24}$ alkenyl chain or

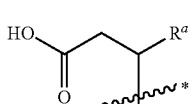 or 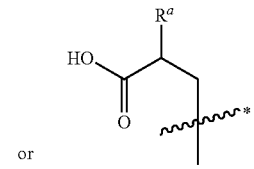

wherein $R^a$ is a $C_1$-$C_{24}$ alkenyl linear or branched chain.

In yet another embodiment of the present invention is a compound of Structure II wherein each $R_2$, $R_3$ is independently an optionally a methyl group or H; independently an optionally a $C_1$-$C_8$ linear, branched, a cyclic alkyl group or H.

In another embodiment of the present invention is a compound represented by the Structural Formula III:

Structural Formula III

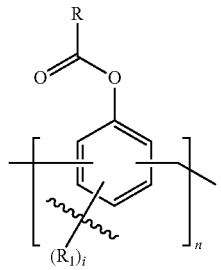

wherein, R is a linear or branched $C_1$-$C_{26}$ alkyl chain,

Each $R_1$ is H, independently an optionally substituted $C_1$-$C_{20}$ linear or branched alkyl group, a tertiary carbon group, a methyl group, a methoxy group, an optionally substituted aryl group, and an optionally substituted $C_1$-$C_{20}$ linear or branched alkoxy group, an optionally substituted carbonyl group, an optionally substituted $C_1$-$C_{20}$ linear or branched alkoxycarbonyl group, an optionally-CH(R''')(R'''COOH) wherein each R''' independently is $C_1$-$C_{10}$ linear or branched alkyl chain, —OH, —SH or —NH$_2$ or an optionally substituted carbocyclic or heterocyclic $C_1$-$C_{12}$ non-aromatic ring, and
i is 0, 1, 2 or 3,
n is an integer from 1 to 1000 or 0 to 100, 0 to 50 or 0 to 25, 0 to 15, or preferably 0 to 10

In another embodiment of the present invention is a compound of structural formula (III) where R is a saturated fatty acid derived from natural resources like plants, vegetable oils or animal fats.

In another embodiment of the present invention is a compound of structural formula (III) where R is a saturated fatty acid, caprylic acid (8:0), capric acid (10:0), lauric acid (12:0), myristic acid (14:0), palmitic acid (16:0), stearic acid (18:0), arachidic acid (20:0), behenic acid (22:0), lignoceric acid (24:0), or cerotic acid(26:0).

In another embodiment of the present invention is a compound of structural formula (III) where R is a mixture of saturated alkyl chains of saturated fatty acids derived natural resources like plants, vegetable oils or animal fat.

In another embodiment, the present invention is a compound of structural formula (III) where $R_1$ independently for each occurrence is selected from the group consisting of

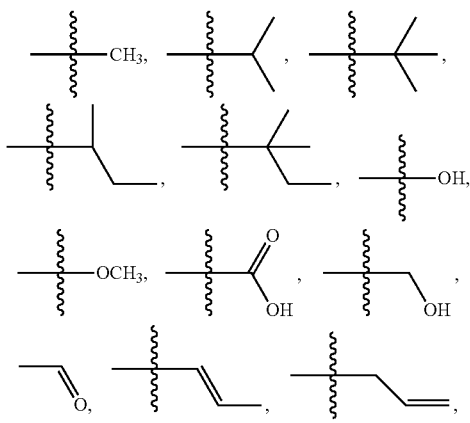

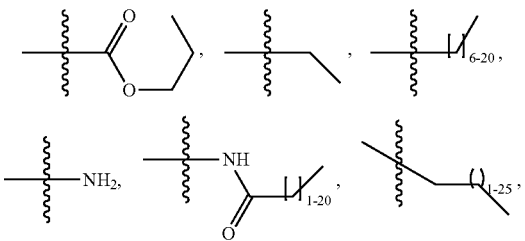

In another embodiment, the present invention is a compound of structural formula (III) where R is represented by (a)

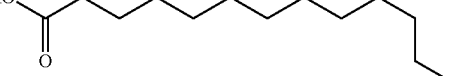

(b)

or a mixture of structural isomers.

In another embodiment the present invention is a compound of structural formula (III) where R is a $C_1$-$C_{26}$ linear or branched alkyl chain or a mixture of $C_8$-$C_{24}$ linear or branched alkyl chains, i is an integer from 0 to 3, and $R_1$ independently for each occurrence is selected from the group consisting of

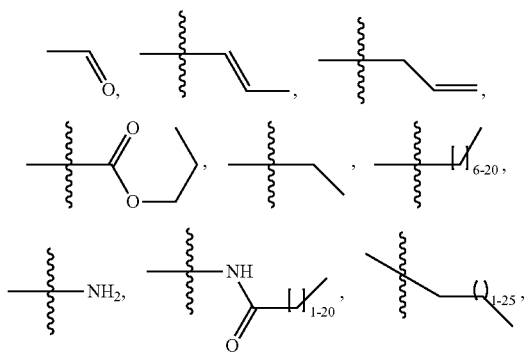
In certain embodiments of the present invention the compounds are represented by the following structural formulas:
Structural Formulas IV
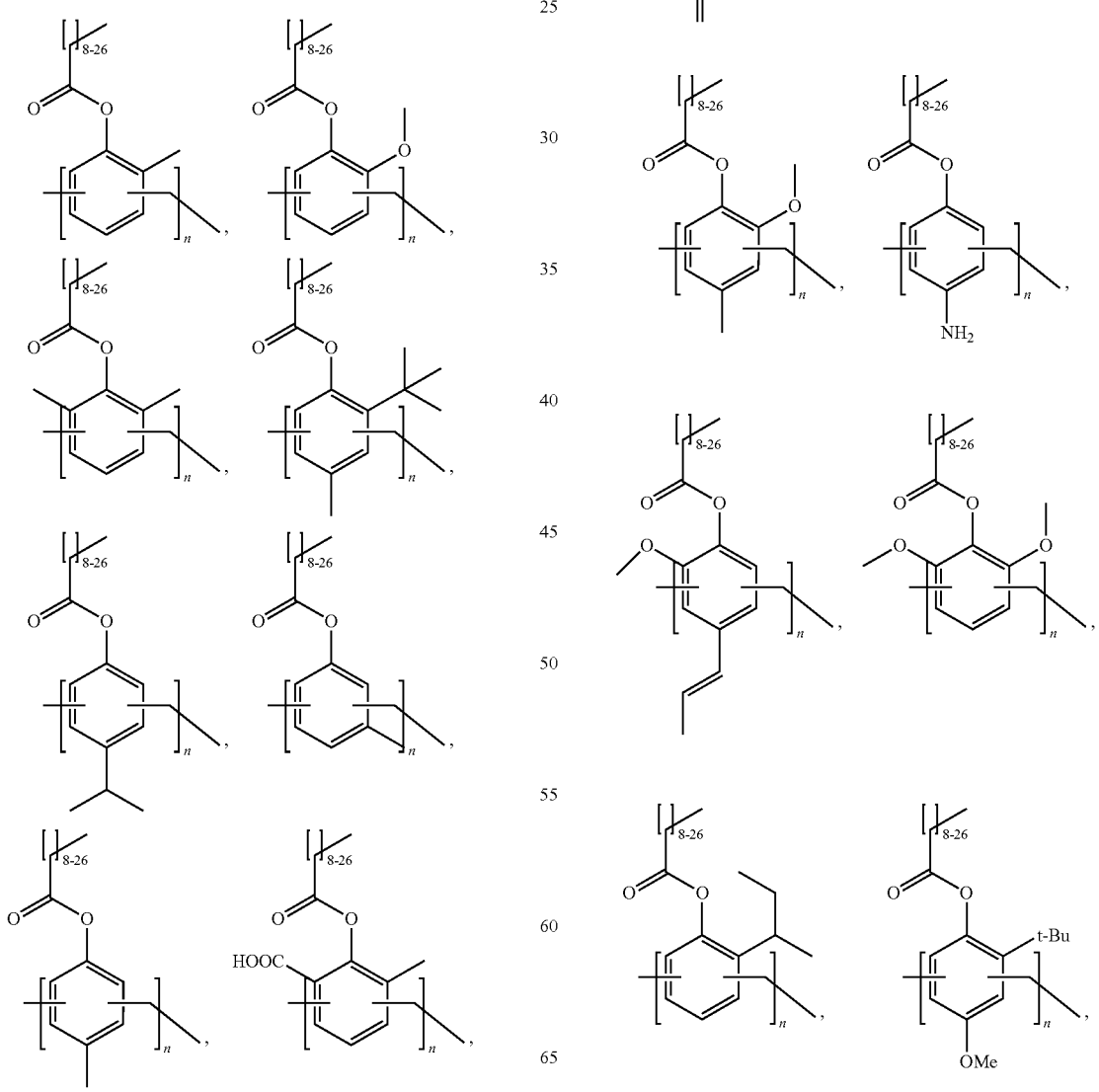
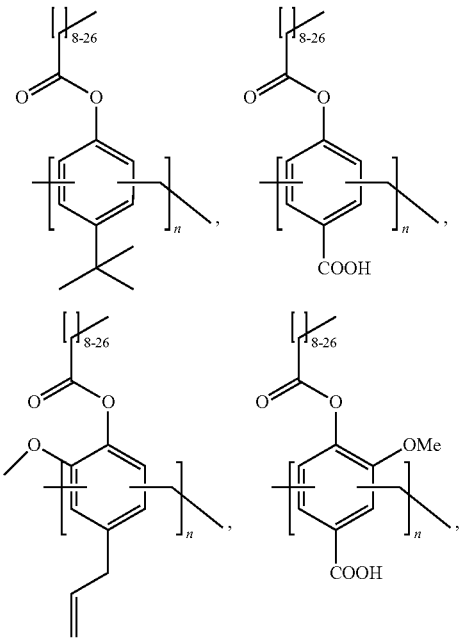

-continued

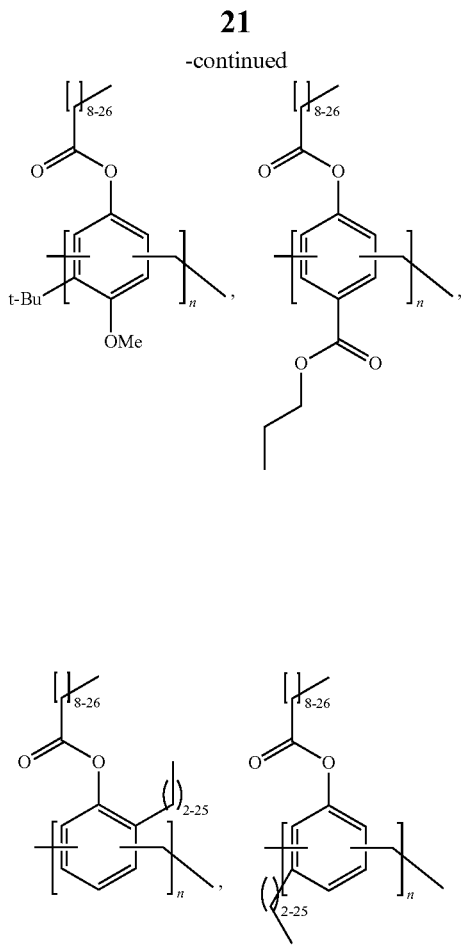

wherein n is an integer from 0 to 100 or 0 to 50 or 0 to 25, 0 to 15, or preferably 0 to 10

In another embodiment of the present invention is a compound of structural formula (IV-a):

Structural Formula VI-a

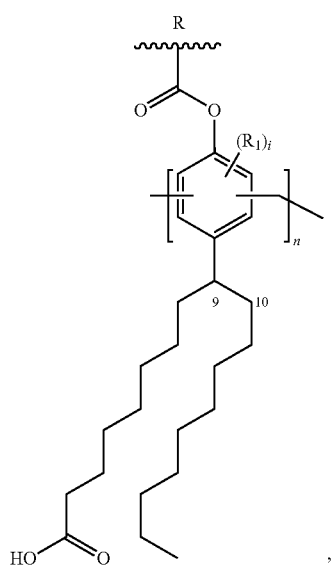

(a)

-continued

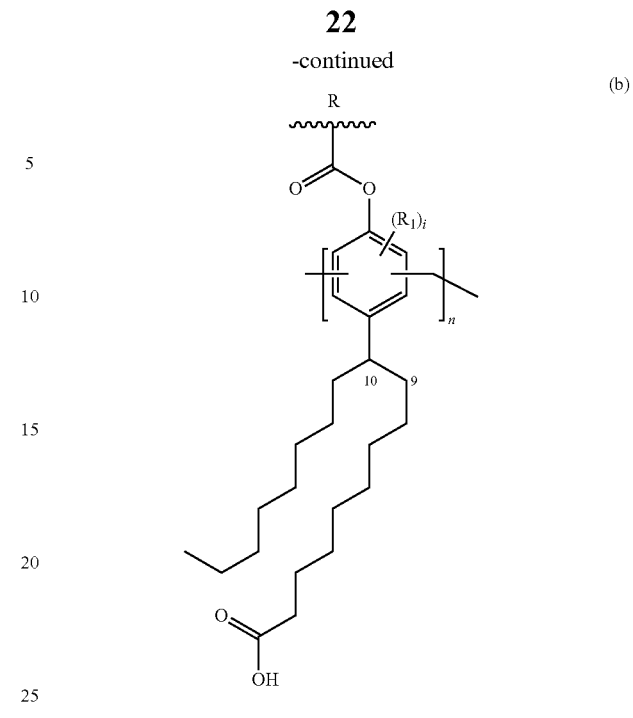

(b)

or a mixture of structural isomers.

wherein R is a $C_1$-$C_{26}$ linear or branched alkyl chain or an alkyl chain of saturated fatty acids 590 derived from renewable resources like plant oils like Jatropha, vegetable oils like canola oil, palm oil, vegetable oils like canola, rapeseed oil, soy oil, palms oil, and alike, and animal fats like tallow oil. The saturated fatty acids are, caprylic acid (8:0), capric acid (10:0), lauric acid (12:0), myristic acid (14:0), palmitic acid (16:0), stearic acid (18:0), arachidic acid (20:0), behenic acid (22:0), lignoceric acid (24:0), or cerotic acid (26:0), Each $R_1$ is H, independently an optionally substituted $C_1$-$C_{20}$ linear or branched alkyl group, a tertiary carbon group, a methyl group, a methoxy group, an optionally substituted aryl group, and an optionally substituted $C_1$-$C_{20}$ linear or branched alkoxy group, an optionally substituted carbonyl group, an optionally substituted $C_1$-$C_{20}$ linear or branched alkoxycarbonyl group, an optionally-CH(R''')(R'''COOH) wherein each R''' independently is $C_1$-$C_{10}$ linear or branched alkyl chain, —OH, —SH or —NH$_2$ or an optionally substituted carbocyclic or heterocyclic $C_1$-$C_{12}$ non-aromatic ring.

i=0 or 1, n is an integer from 0 to 100 or 0 to 50 or 0 to 25, 0 to 15, or preferably 0 to 10.

In yet another embodiment, the present invention is a compound or a mixture of compounds represented by Structural formula III, IV or IVa wherein the compound is the composition of that are the reaction products of a substituted phenol and an aldehyde which are esterified further with a linear or branched alkyl alcohol containing a $C_1$-$C_{50}$ linear or branched alkyl chain or a mixture of $C_1$-$C_{50}$ linear or branched alkyl chains or preferably linear $C_1$-$C_{26}$ linear or branched alkyl chain or a mixture of linear or branched $C_1$-$C_{26}$ alkyl chains or more preferably $C_{12}$-$C_{18}$ lineal alkyl chain or a mixture of $C_{12}$-$C_{18}$ alkyl chains.

In another embodiment of the present invention is a compound of structural formula V:

Structural Formula V

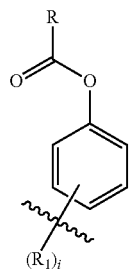

wherein R is a $C_1$-$C_{26}$ linear or branched alkyl chain or a mixture of $C_8$-$C_{24}$ alkyl chains, i is an integer from >1 but ≤3, and each $R_1$ independently is selected from the group consisting of

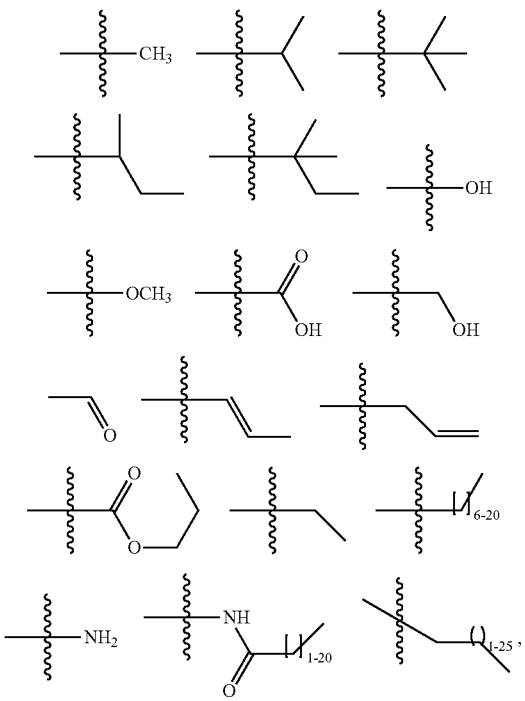

(a)

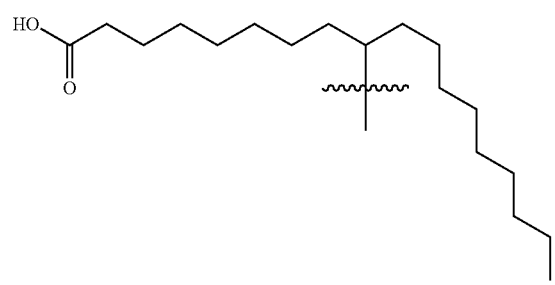

or (b)

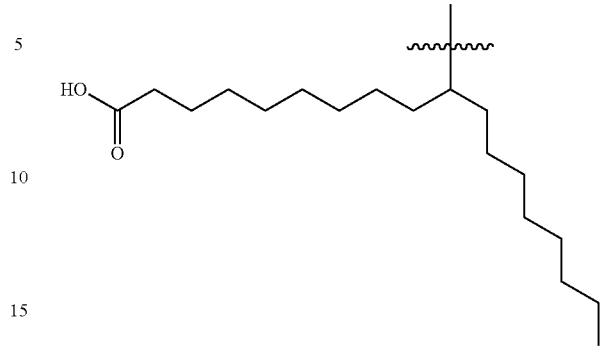

In yet another embodiment, the present invention is a compound or a mixture of 630 compounds represented by structural formulas VI:

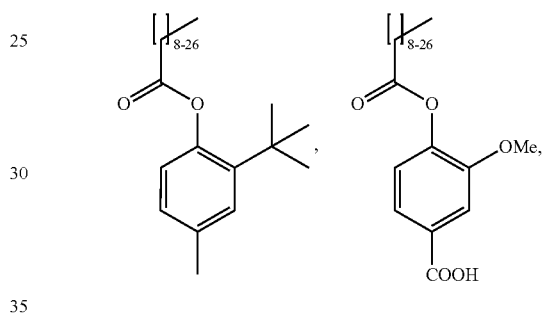

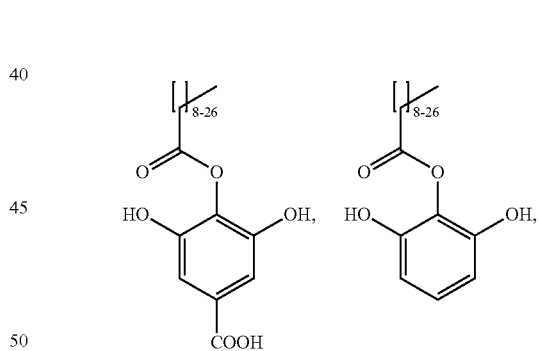

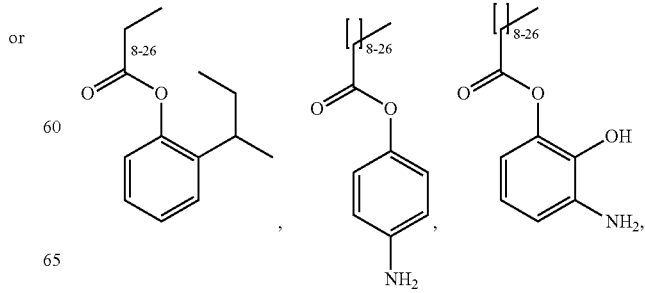

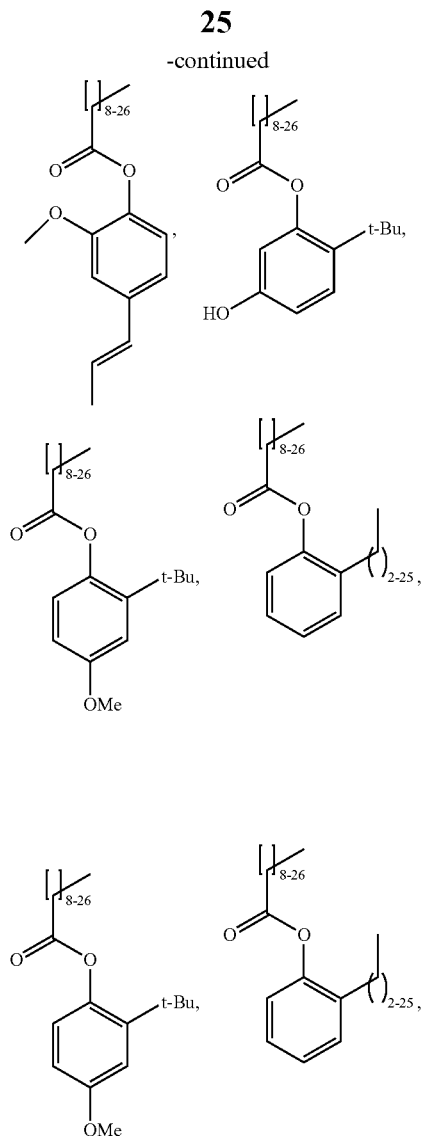

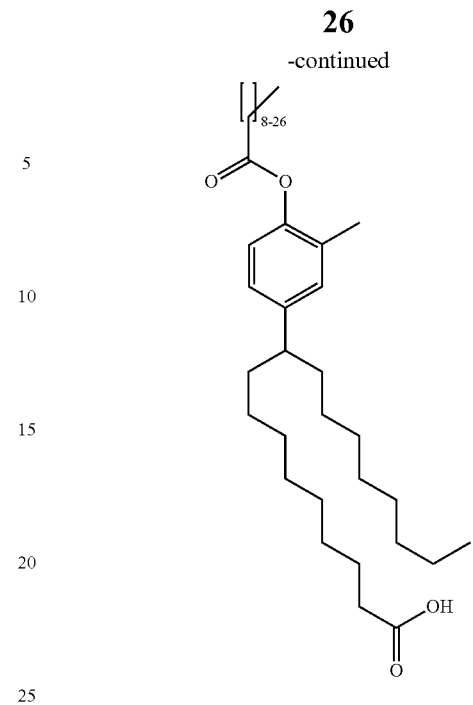

In another embodiment of the present invention represented by structural formulas IV-V where in R is a $C_1$-$C_{26}$ linear or branched alkyl chain or a saturated fatty acid or mixture of saturated fatty acids derived from renewable resources like plant oils like Jatropha, vegetable oils like canola oil, palm oil, vegetable oils like canola, rapeseed oil, soy oil, palms oil, and alike, and animal fats like tallow oil. The saturated fatty acids are, caprylic acid (8:0), capric acid (10:0), 640 lauric acid (12:0), myristic acid (14:0), palmitic acid (16:0), stearic acid (18:0), arachidic acid (20:0), behenic acid (22:0), lignoceric acid (24:0), or cerotic acid (26:0).

In another embodiment of the present invention is represented by an isomerized structural formula (VI-a):

Structural Formula VI-a

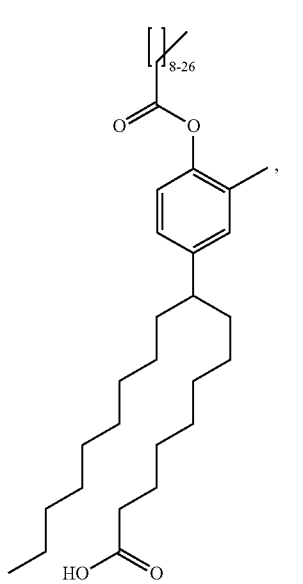

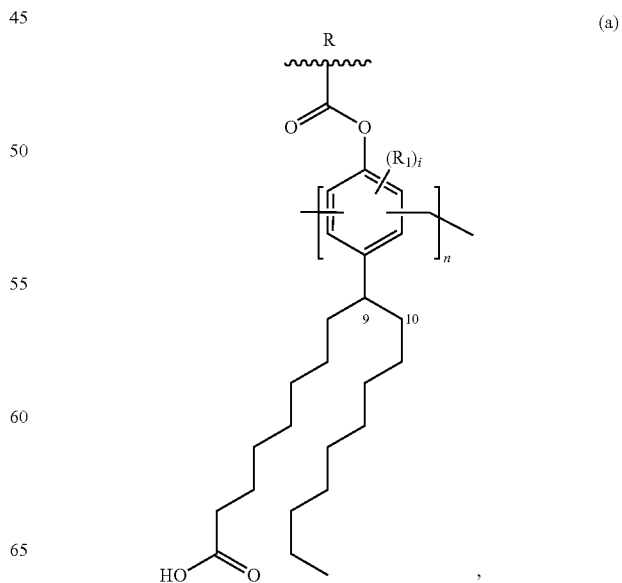

27
-continued

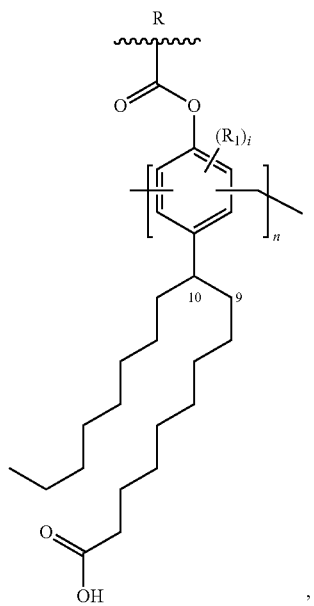

, or a mixture of structural isomers.

wherein R is a $C_1$-$C_{26}$ linear or branched alkyl chain or a saturated fatty acid or saturated fatty acids derived from renewable resources like plant oils like Jatropha, vegetable oils like canola oil, palm oil, vegetable oils like canola, rapeseed oil, soy oil, palms oil, and alike, and animal fats like tallow oil. The saturated fatty acids are, caprylic acid (8:0), capric acid (10:0), lauric acid (12:0), myristic acid (14:0), palmitic acid (16:0), stearic acid (18:0), arachidic acid (20:0), behenic acid (22:0), lignoceric acid (24:0), or cerotic acid(26:0), and the remaining variables are 655 as described in the immediately preceding paragraph or for structural formula (I), (II) or (III).

In another embodiment, the present invention addresses to a compound represented by structural formula VII Structural Formula VII

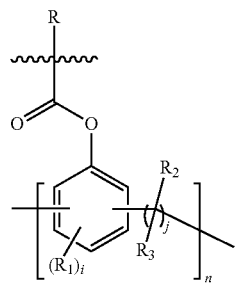

28 wherein
(b) R is an alkenyl isomer represented by

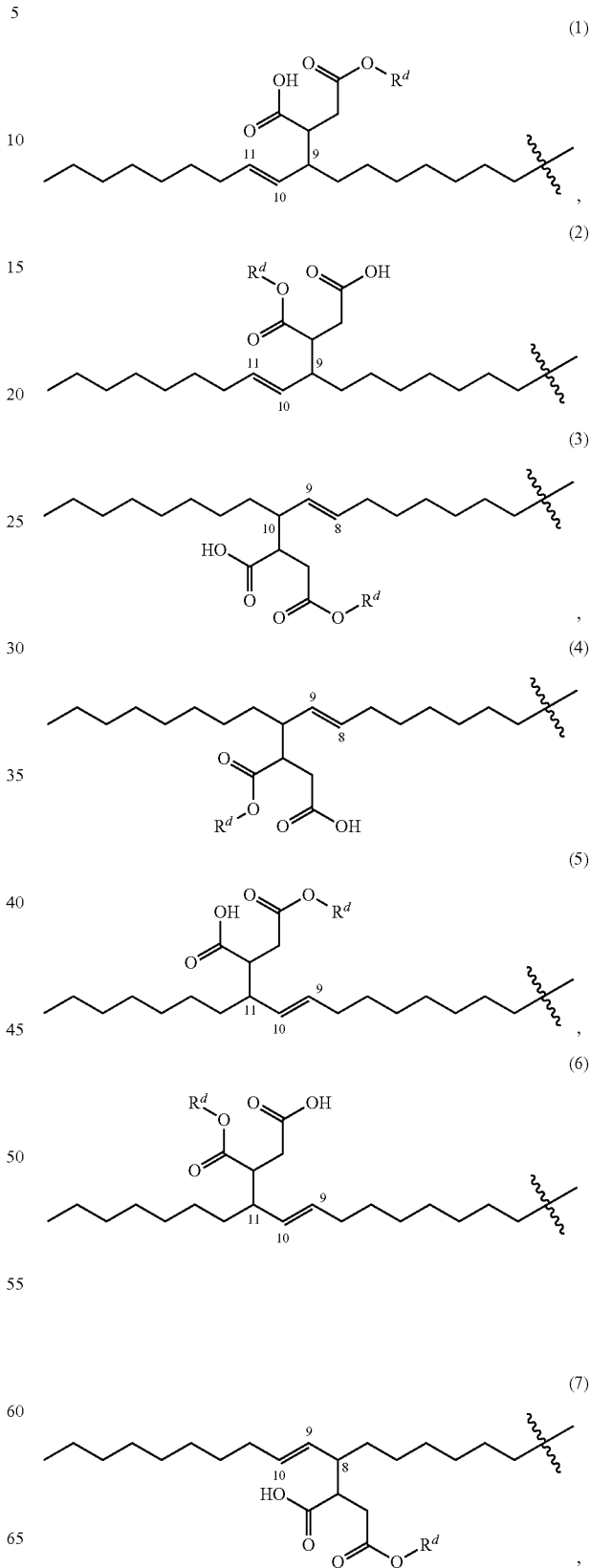

or a mixture of structural isomers.

(8)

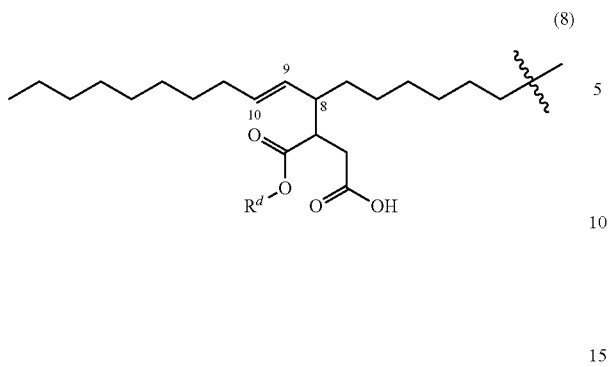

(b)

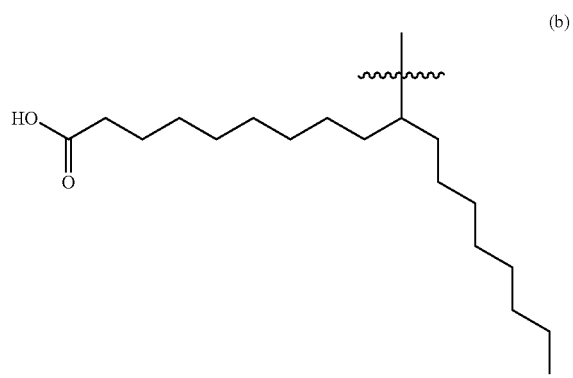

or a mixture of structural isomers, $R^d$ is H or a $C_1$-$C_{18}$ linear or branched alkyl chain, —[$CH_2$]$_p$—$CH_3$ with p being an integer from 0 to 30. In some instances p is from 3 to 25, in some instances p is 7 to 17, in some instances p is from 11 to 17, in some instances p from 13-15, in some instances p is from 15 to 17, in some 670 instances p is 0, 7, 9, 11, 13, 15, or 17 or a mixture thereof, Each $R_1$ is H, independently an optionally substituted $C_1$-$C_{20}$ linear or branched alkyl group, a tertiary carbon group, a methyl group, a methoxy group, an optionally substituted aryl group, and an optionally substituted $C_1$-$C_{20}$ linear or branched alkoxy group, an optionally substituted carbonyl group, an optionally substituted $C_1$-$C_{20}$ linear or branched alkoxycarbonyl group, an optionally-CH(R''') (R'''COOH) wherein each R''' independently is $C_1$-$C_{10}$ linear or branched alkyl chain, —OH, —SH or —NH$_2$ or an optionally substituted carbocyclic or heterocyclic $C_1$-$C_{12}$ non-aromatic ring.

i=0 or 1, j=0 or 1;

n is an integer from 0 to 100 or 0 to 50 or 0 to 25, 0 to 15, or preferably 0 to 10;

when n=1, then j is always 0;

when n>1 then j=1;

each $R_2$, $R_3$, independently is H, methyl, or a $C_1$-$C_8$ linear or branched or cyclic alkyl chain.

In another embodiment, the present invention is a compound of structural formula (VII) where $R_1$ is an isomerized structure represented by

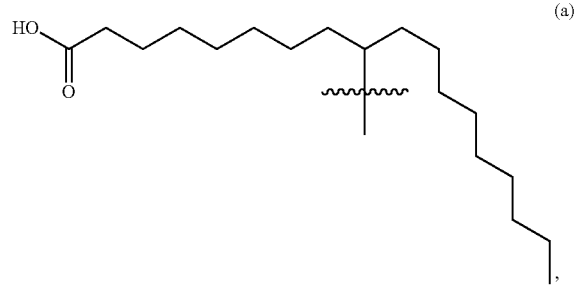

(a)

or a mixture of isomers.

In another embodiment, the present invention addresses to a compound represented by structural formula VIII:

Structural Formula VIII

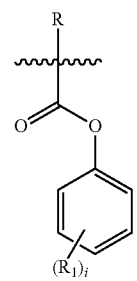

wherein,

R is an alkenyl isomer represented by

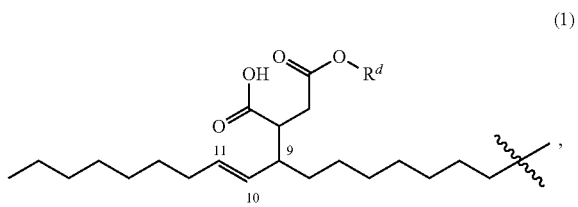

(1)

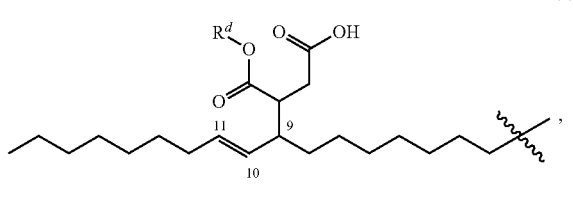

(2)

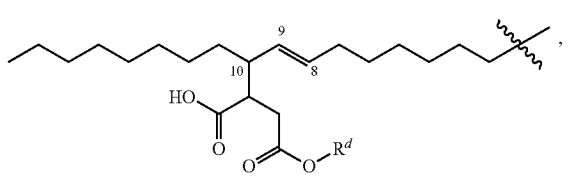

(3)

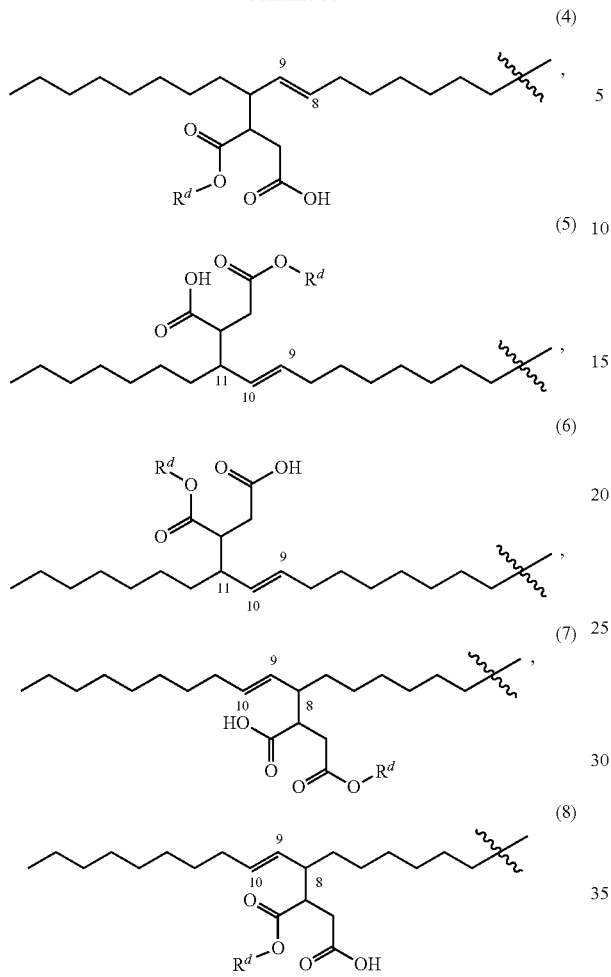

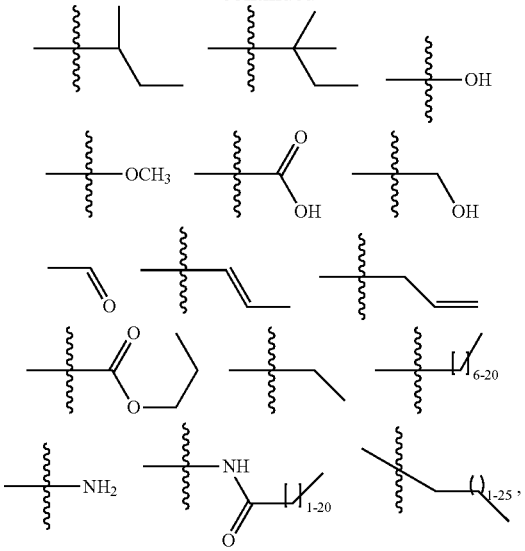

or a mixture of isomerized structures;

$R^d$ is H or $C_1$-$C_{18}$ linear or branched alkyl chains, —[$CH_2$]$_p$$CH_3$ with p being an integer from 0 to 30. In some instances p is from 3 to 25, in some instances p is 7 to 17, in some instances p is from 11 to 17, in some instances p from 13-15, in some instances p is from 15 to 17, in some instances p is 0, 7, 9, 11, 13, 15, or 17 or a mixture thereof;

Each $R_1$ is H, independently an optionally substituted $C_1$-$C_{20}$ alkyl group, a tertiary carbon group, a methyl group, a methoxy group, an optionally substituted aryl group, and optionally substituted $C_1$-$C_{20}$ alkoxy group, an optionally substituted carbonyl group, an optionally substituted $C_1$-$C_{20}$ alkoxycarbonyl group, an optionally -CH(R''')(R'''COOH) wherein each R''' independently is $C_1$-$C_{10}$ linear or branched alkyl chain, —OH, —SH or —$NH_2$ or an optionally substituted carbocyclic or heterocyclic $C_1$-$C_{12}$ non-aromatic ring;

i=0 or 1 or 2 or 3;

In another embodiment, the present invention is a compound of structural formula VIII where $R_1$ is selected from the group consisting of

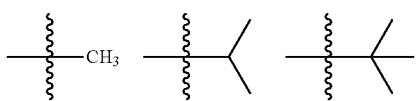

and, in proviso substituted phenol is not a phenol, 2,4-dimethylphenol or resorcinol if R is arising from DDSA (dodecenyl succinic anhydride), ODSA (octadecenyl succinic anhydride), OSA (octenyl succinic anhydride), or PIBSA (polyisobutylene succinic anhydride).

In another embodiment, the present invention is a compound of structural formula (VIII) where $R_1$ is an isomerized structure represented by

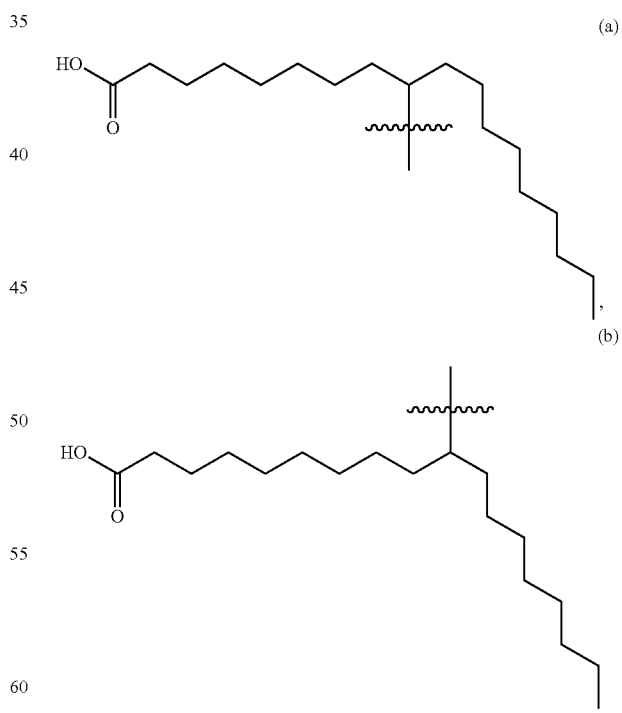

or a mixture of isomers.

In yet another embodiment of the present invention is a compound or a mixture of compounds represented by structural formulas VIII where is R is an alkenyl portion of [monosaturated fatty acid succinic anhydride] isomers when their anhydride rings are opened by a saturated fatty alcohol selected from the chain lengths ranging from $C_8$ to $C_{26}$. The preferred monosaturated fatty acid-succinic anhydride is an oleic acid-succinic anhydride (OASA). The isomer structures of an OASA are consisting of

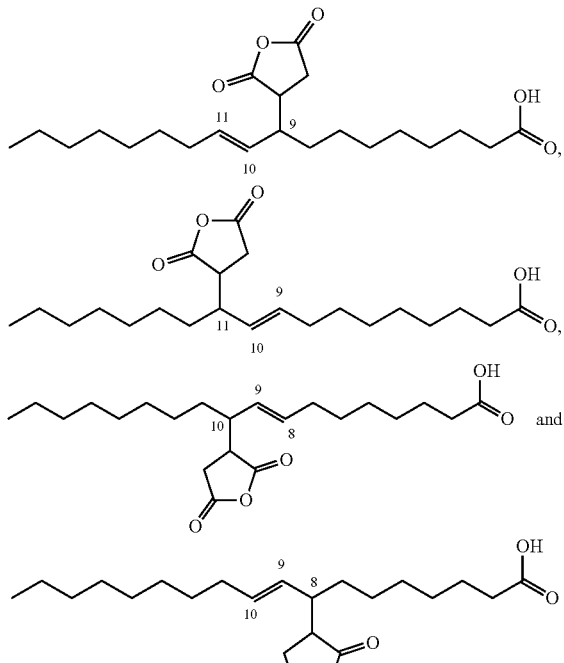

Isomer Structures of OASA

In yet another embodiment of the present invention is a compound or a mixture of compounds represented by structural formulas VIII where is R is an alkenyl portion of [monosaturated fatty acid-succinic anhydride] isomers when their anhydride rings are opened by a fatty alcohol selected from the chain lengths ranging from $C_8$ to $C_{26}$. The preferred monosaturated fatty acid-succinic anhydride compound is oleic acid-succinic anhydride (OASA) and the fatty acid alcohol is stearyl alcohol ($CH_3(CH_2)_{17}OH$). The isomer structures of OASA after reacting with a fatty alcohol, $R^d$—OH are:

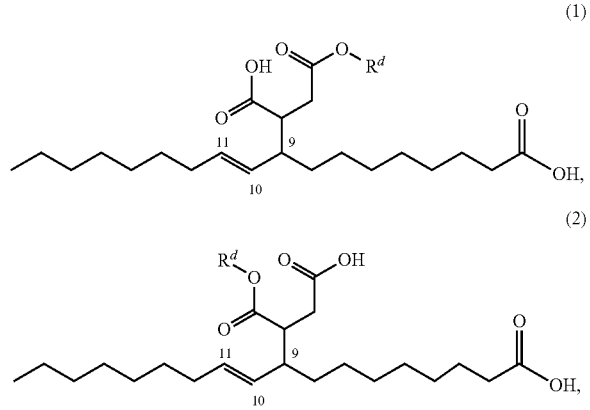

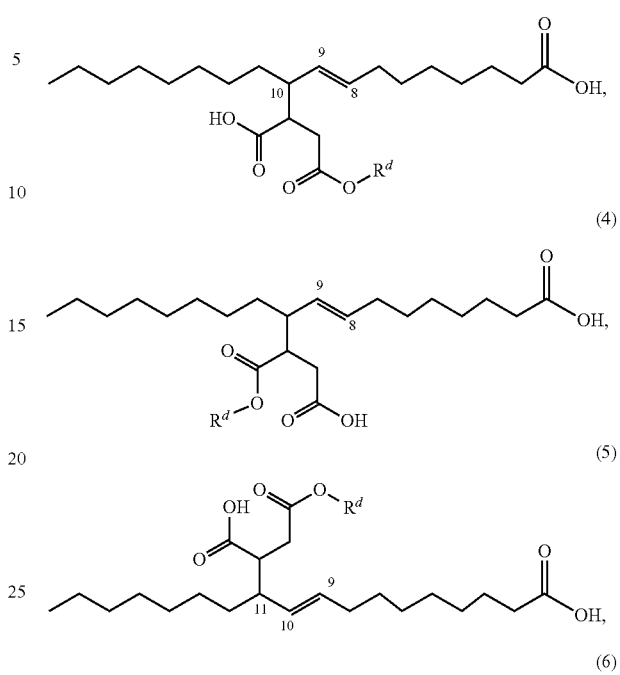

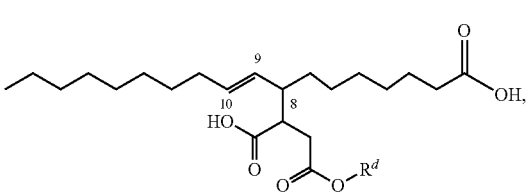

wherein, $R^d$ is H or $C_1$-$C_{18}$ linear or branched alkyl chains, —$[CH_2]_p CH_3$ with p being an integer from 0 to 30. In some instances p is from 3 to 25, in some instances p is 7 to 17, in some instances p is from 11 to 17, in some instances p from 13-15, in some instances p is from 15 to 17, in some instances p is 0, 7, 9, 11, 13, 15, or 17 or a mixture thereof.

In yet another embodiment, the present invention is a compound or a mixture of compounds represented by structural formulas IX:
Structual Formulas IX
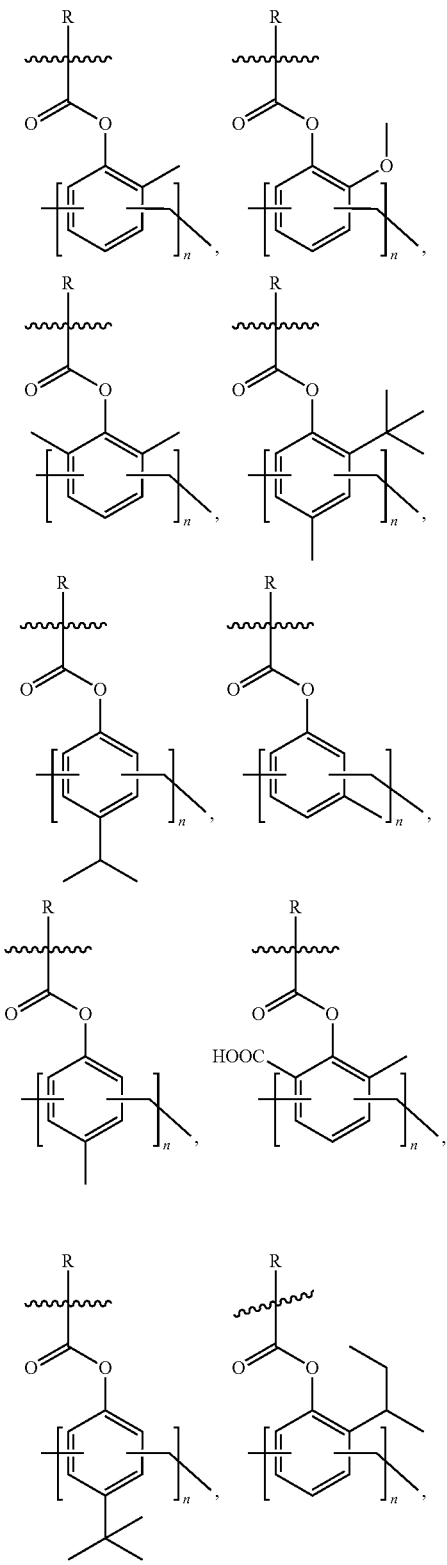
-continued
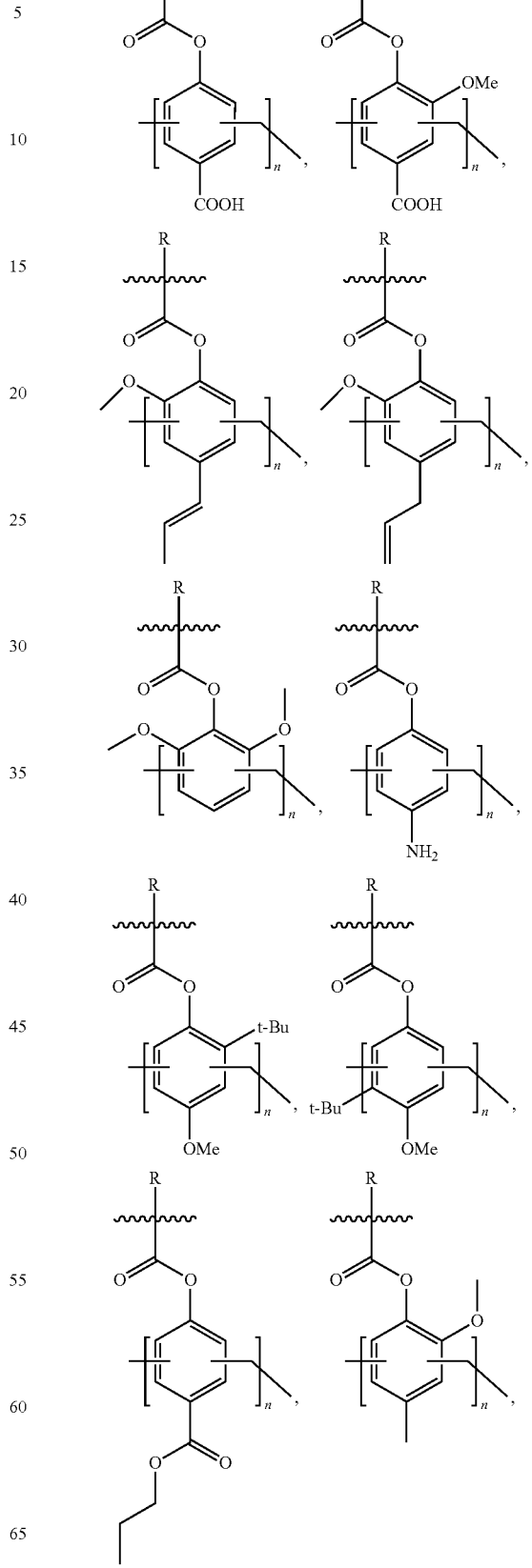

-continued

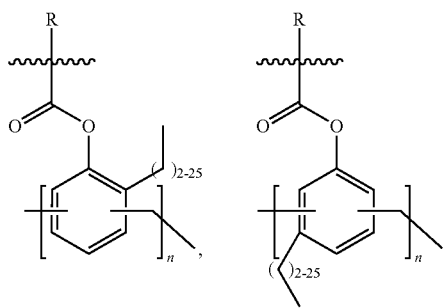

wherein R is an alkenyl structural isomer represented by

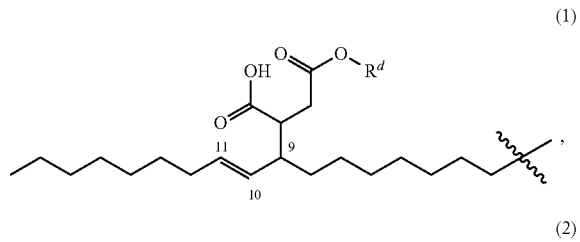  (1)

(2)

(3)

(4)

(5)

(6)

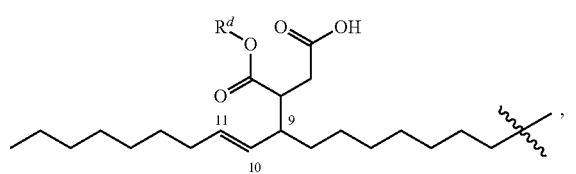

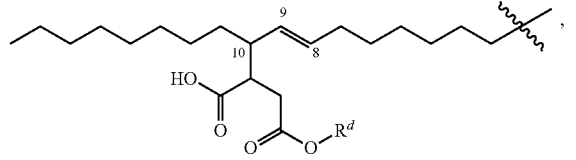

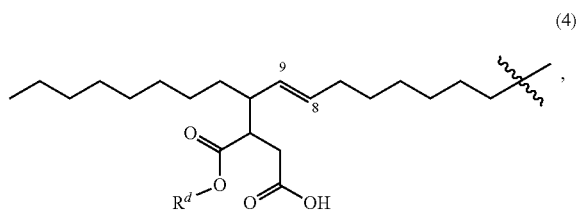

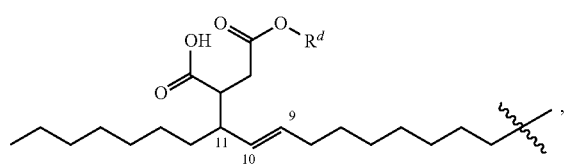

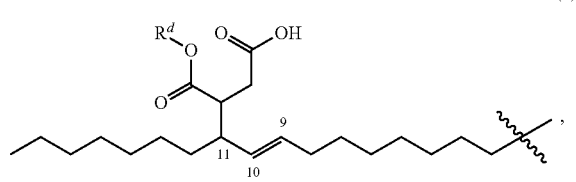

-continued (7)

(8)

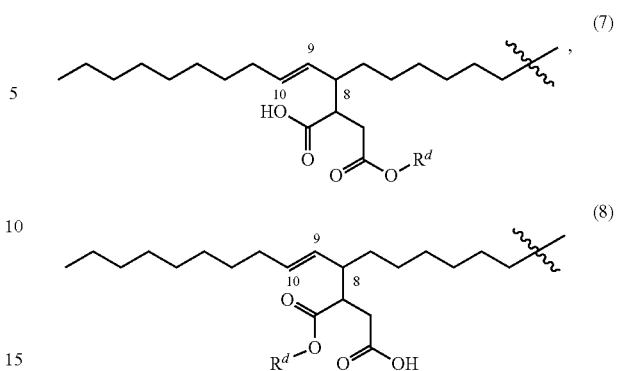

or a mixture of isomers;

$R_d$ is H or $C_1$-$C_{18}$ linear or branched alkyl chains, —[$CH_2$]$_p$$CH_3$ with p being an integer from 0 to 30. In some instances p is from 3 to 25, in some instances p is 7 to 17, in some instances p is from 11 to 17, in some instances p from 13-15, in some instances p is from 15 to 17, in some instances p is 0, 7, 9, 11, 13, 15, or 17 or a mixture thereof.

In yet another embodiment, the present invention is a compound or a mixture of compounds represented by structural formulas X:

Structural Formulas X

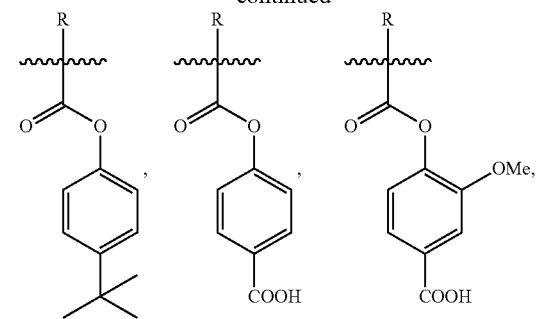
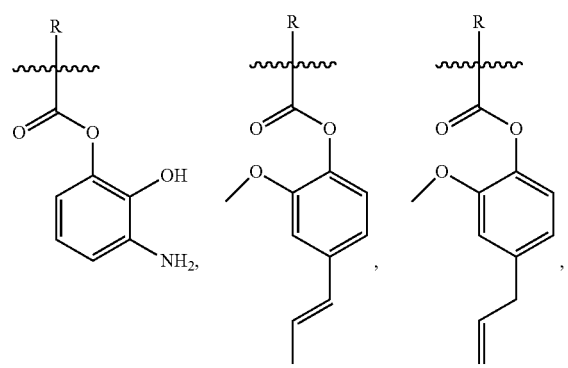
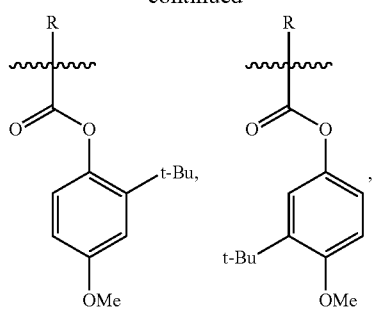
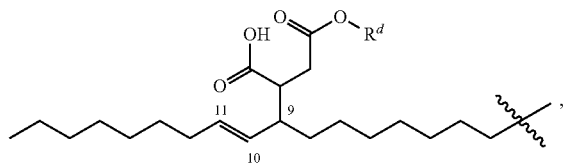
wherein R is an alkenyl structural isomer represented by
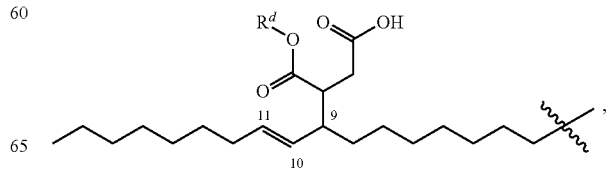

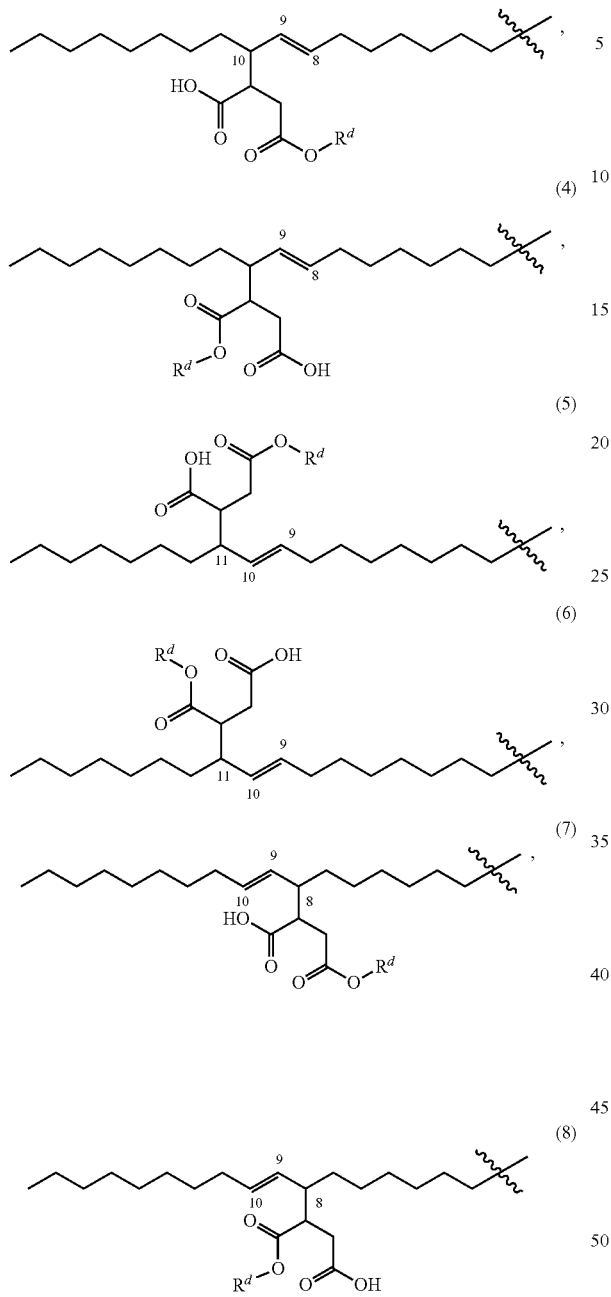

or a mixture isomer structures, wherein $R^d$ is H or $C_1$-$C_{18}$ linear or branched alkyl chains, —[CH$_2$]$_p$CH$_3$ with p being an integer from 0 to 30. In some instances p is from 3 to 25, in some instances p is 7 to 17, in some instances p is from 11 to 17, in some instances p from 13-15, in some instances p is from 15 to 17, in some instances p is 0, 7, 9, 11, 13, 15, or 17 or a mixture thereof.

In certain embodiments, the present invention relates to a compound represented by structural formula XI (a mixture of structural isomers):

Structural Formula XI

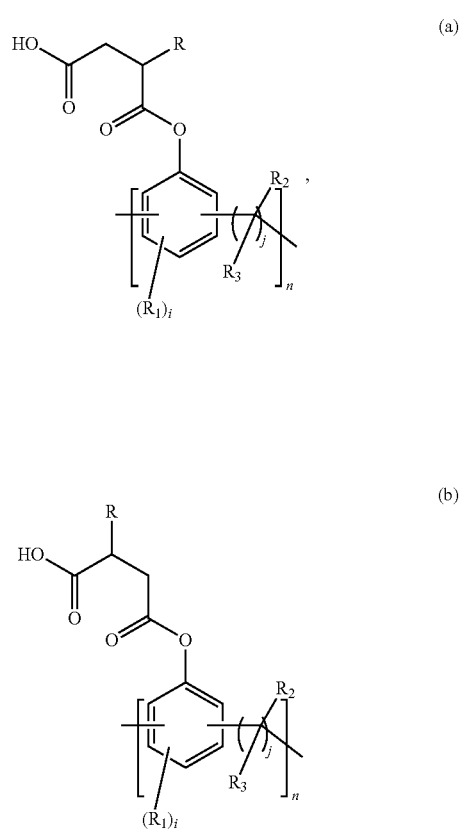

or a mixture of isomers,
wherein,

R is a $C_1$-$C_{18}$ linear or branched alkyl chain, or an alkenyl chain of PIBSA, OSA, DDSA, and ODSA, and the remaining variables are as described for structural formula (I), (II) or (III).

In yet another embodiment, the present invention is a compound or a mixture of compounds represented by Structural formula XI wherein the polymers that are the reaction products of a substituted phenol and an aldehyde which is further esterified with PIBSA, DDSA, ODSA, or OSA.

In another embodiment, the present invention is a compound of isomerized structural formula (XI) where $R_1$ is represented by

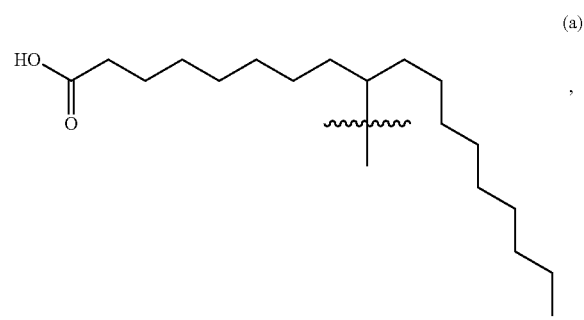

-continued

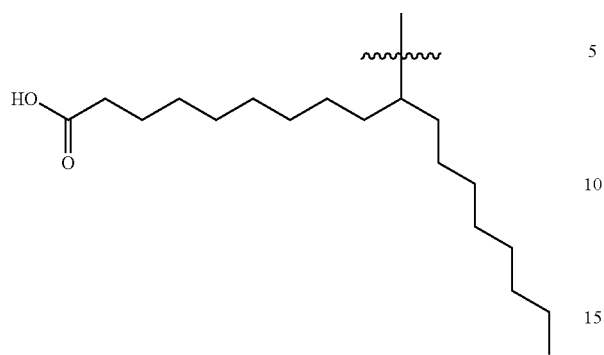

or a mixture of isomers.

In yet another embodiment, the present invention is a compound represented by structural formulas XII with optionally their corresponding structural isomer or mixture of structural isomers:

Structural Formula XII

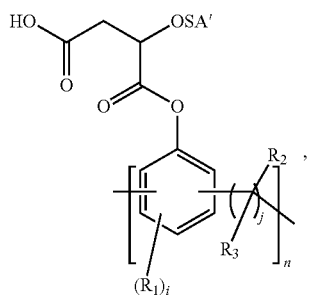

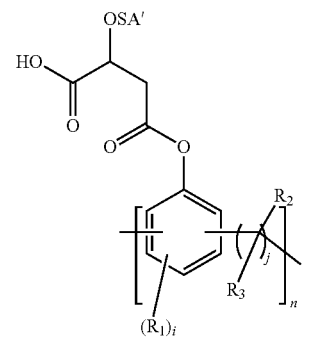

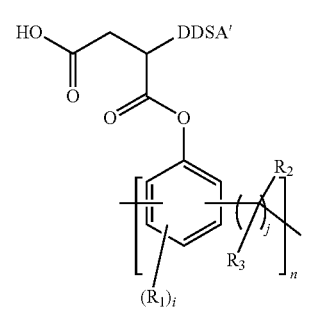

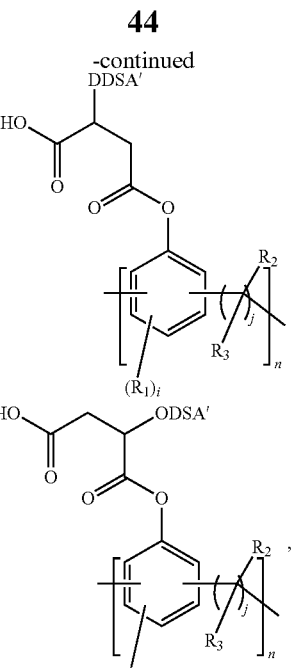

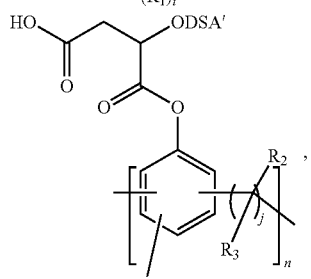

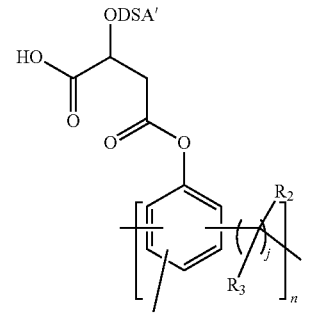

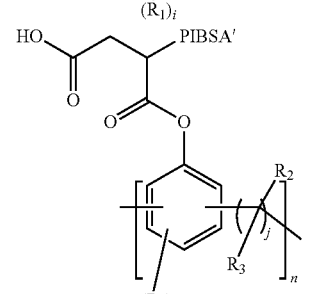

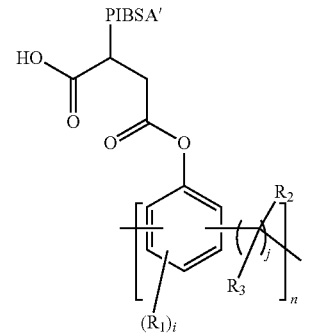

wherein,

OSA', DDSA', ODSA', PIBSA' are alkenyl chain portion of OSA, octenyl succinic anhydride; DDSA, dodecenyl succinic anhydride; ODSA, octadecenyl succinic anhydride;

PIBSA, polyisobutylene succinic anhydride (low molecular weight, 300-1500 molecular weight), respectively;

each $R_2$, $R_3$ is independently an optionally a methyl group or H; independently an optionally a $C_1$-$C_8$ linear, branched, a cyclic alkyl group, the remaining variables are as described for structural formula (I), (II) or (III).

In another embodiment, the present invention is a compound of structural formula (XII) where $R_1$ is represented by (a)
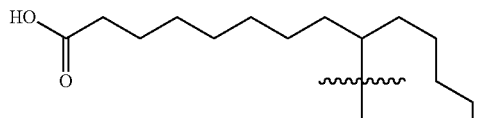

(b)
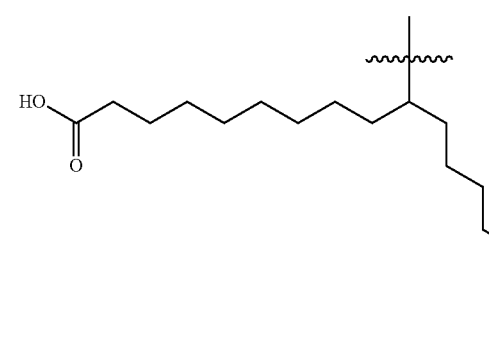

or a mixture of structural isomers.

In yet another embodiment, the present invention is a compound represented by structural formula I where n is 1, j is 0, Structural Formula XIII

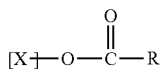

wherein [X] is

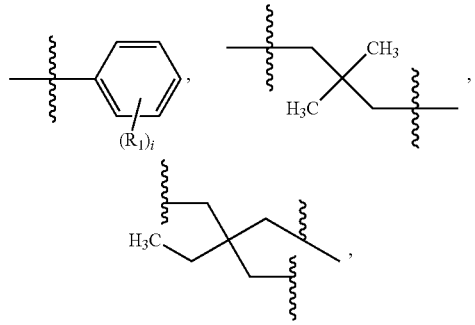

-continued

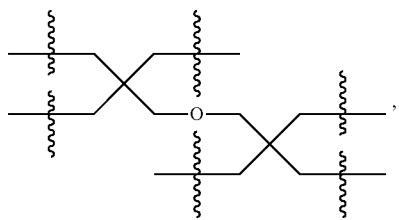

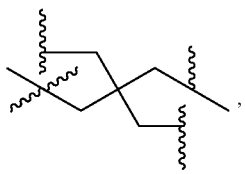 , 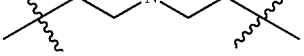 ,

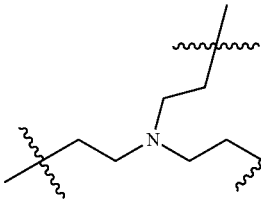

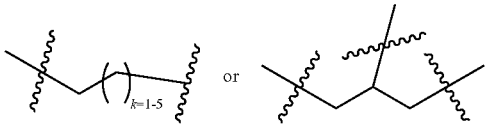

R is an isomerized alkenyl chain represented by (1)
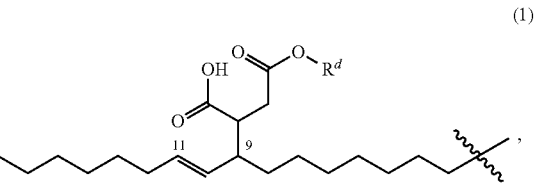

(2)
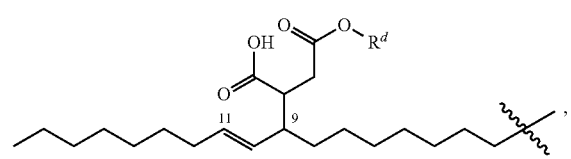

(3)
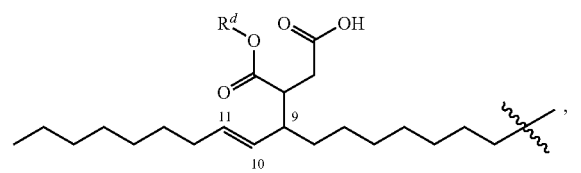

(4)
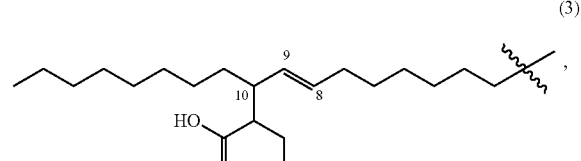

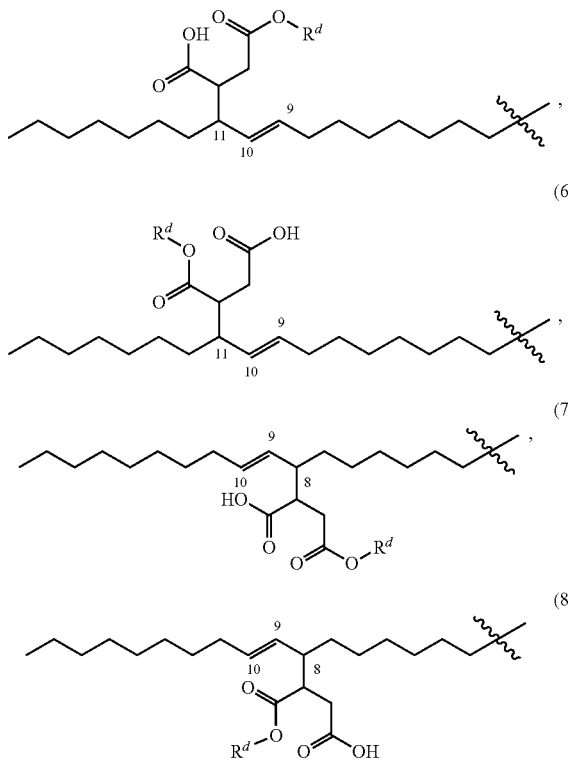

or a mixture of isomers; and each $R^d$ is a $C_1$-$C_{24}$ alkyl chain.

In another embodiment of the present invention is an isomeric compound represented by structural formula XIII wherein, R is an isomerized alkenyl chain represented by

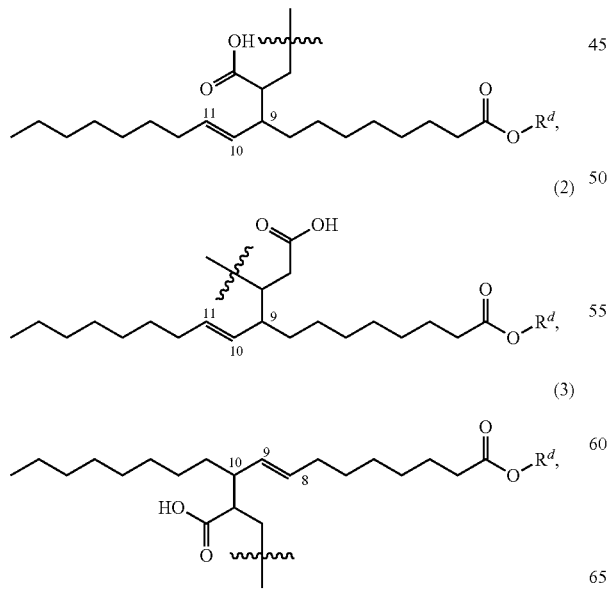

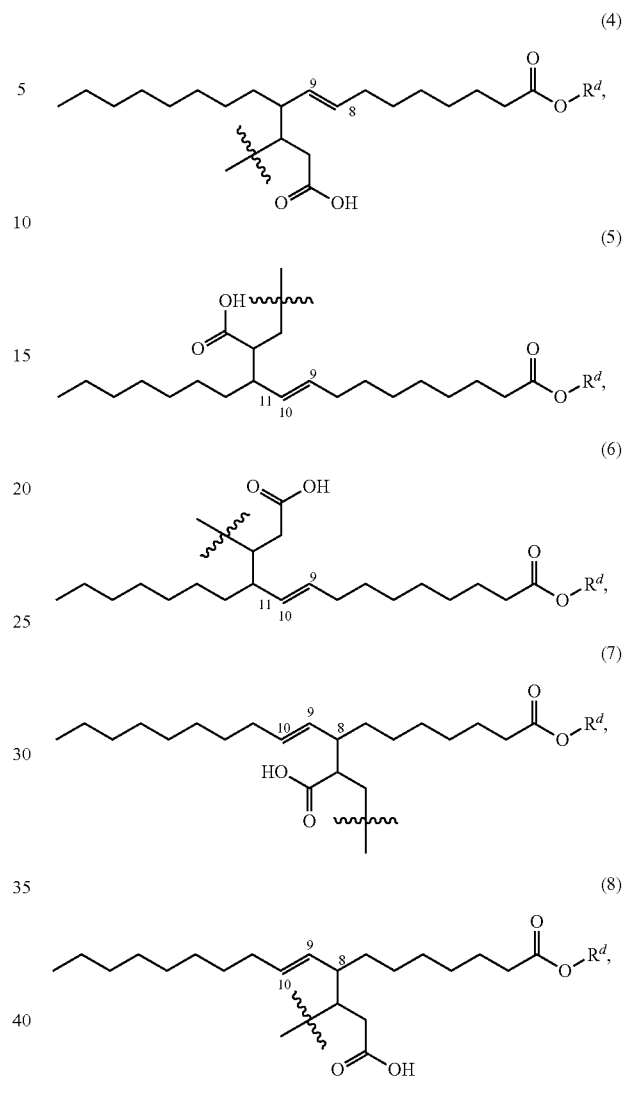

or their isomer mixtures (1)-(8); and each $R^d$ is a $C_1$-$C_{24}$ alkyl chain.

In another embodiment of the present invention is an isomeric compound represented by structural formula XIII-A:

Structural Formula XIII-A

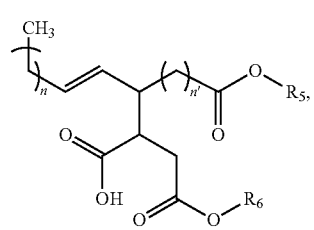

-continued (b)
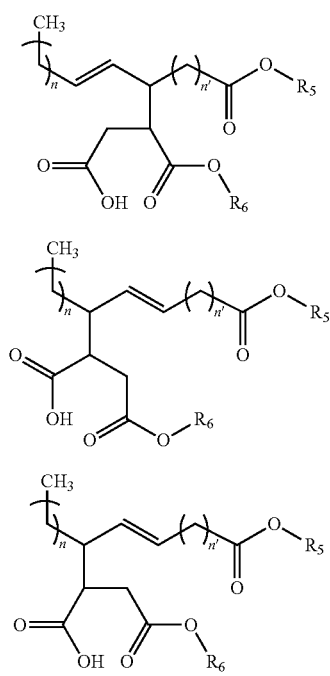

(c)

(d)

or a mixture of structural isomers
wherein

Each $R_5$, $R_6$ independently is H, methyl, or a $C_1$-$C_{24}$ linear or branched or cyclic alkyl chain, Each n, n' independently is 1 to 15, preferably 4 to 10.

In another embodiment of the present invention, a method of producing a compound having Structural Formula I:

Structural Formula I

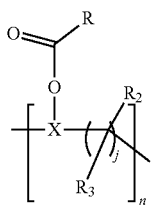

wherein
X is

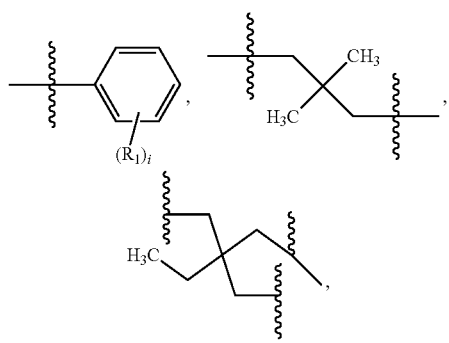

-continued

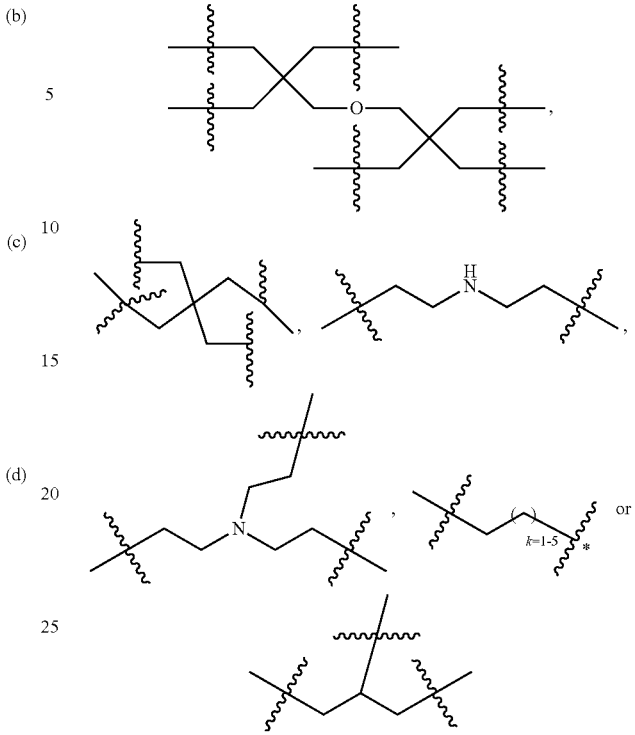

each $R_1$ is H, independently an optionally substituted $C_1$-$C_{20}$ alkyl group, an optionally substituted $C_1$-$C_{10}$ alkyl group, a tertiary carbon group, a methyl group, a methoxy group, an optionally substituted aryl group, and optionally substituted alkoxy group, an optionally substituted carbonyl group, an optionally substituted alkoxycarbonyl group, an optionally-CH(R''')(R'''COOH) wherein each R''' independently $C_1$-$C_{10}$ linear or branched alkyl chain, —OH, —SH or —NH$_2$ or an optionally substituted carbocyclic or heterocyclic non-aromatic ring.

I=0, 1, 2, 3;
j=0 or 1;
n is an integer from 1 to 1000 or 1 to 100, 1 to 50 or 1 to 25, 1 to 15, or 865 preferably 1 to 10,
when n=1, then j=0;
when n>1 then j=1;
each $R_2$ and $R_3$ is independently H, a C1-C8 linear or branched or cyclic alkyl chain, an optionally substituted $C_1$-$C_{20}$ alkyl group, an optionally substituted $C_1$-$C_{10}$ alkyl group, a tertiary carbon group, a methyl group, a methoxy group, an optionally substituted aryl group, and optionally substituted alkoxy group, an optionally substituted carbonyl group, an optionally substituted alkoxycarbonyl group, or —CH(R''')(R'''COOH)

R is a $C_1$-$C_{24}$ linear or branched alkyl chain, alkenyl chain, or an isomerized structure or a mixture of isomerized (A) and (B):

(A)
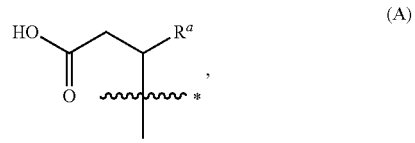

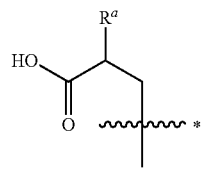
(B)

wherein $R^a$ is a $C_1$-$C_{24}$ alkenyl linear or branched chain, the method comprising:
(a) reacting X in a solvent with an aldehyde selected from the group of formaldehyde, acetaldehyde, valeraldehyde, butyraldehyde, isovalrealdehyde, 2-methyl butanal, benzaldehyde, cyclohexanecarbaldehyde, 3-methylcyclohexanecrabaldehyde, glyceraldehyde, glucose aldehyde,
(b) Reacting the product in (a) with an alkyl acyl chloride, an oleoyl chloride, or alkenyl succinic anhydride selected from the group of octenyl succinic anhydride (OSA), dodecenyl succinic anhydride (DDSA); octadecenyl succinic anhydride (ODSA); polyisobutylene succinic anhydride (PIBSA) having a molecular weight from 300 to 1500;
(c) Reacting the product of (b) with maleic anhydride if the reactant used in (b) is an oleoyl chloride, and then finally,
(d) Reacting the The succinic anhydride group of product in (c) is reacting with a $C_1$-$C_{24}$ linear or branched or cyclic alcohol.

If the reactant used in (b) is not oleoyl chloride, then (c) can include reacting the product of (b) with oleic acid.

In certain embodiments the methods of present invention, a polymer that is a reaction product of starting materials comprising a substituted phenol and an aldehyde that is further esterified with an alkyl acid through the use of oxalyl chloride or thionyl chloride.

In certain embodiments the alklyl acid used in the methods of the present invention is selected from the group consisting of an alkyl with at least about 4 carbon atoms, preferably $C_5$ to $C_{26}$ acid such as saturated straight chain fatty acid including caprylic acid (8:0), capric acid 905 (10:0), lauric acid (12:0), myristic acid (14:0), palmitic acid (16:0), stearic acid (18:0), arachidic acid (20:0), behenic acid (22:0), lignoceric acid (24:0), or cerotic acid(26:0).

In certain embodiments the substituted phenol used in the methods of the present invention is selected from the group consisting the structural formulas XIV shown below:

Structural Formula XIV

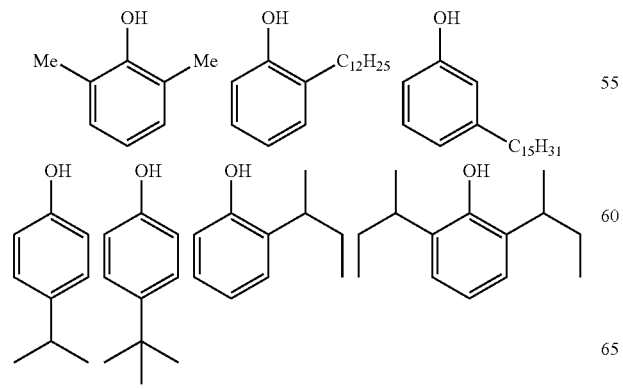

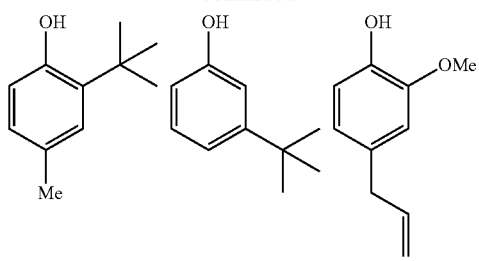
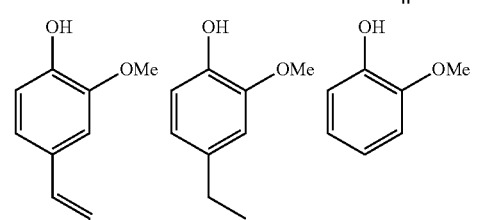
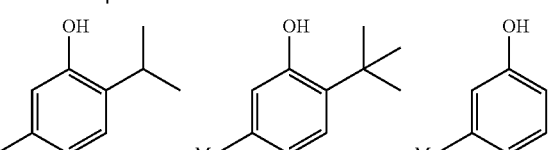
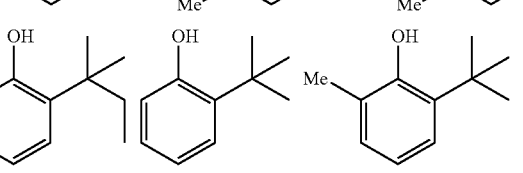
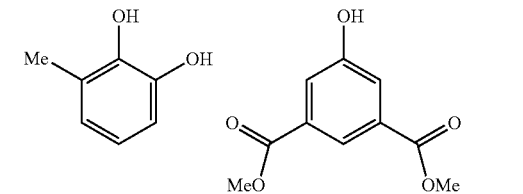
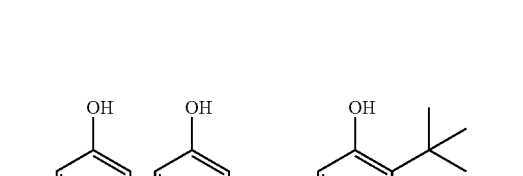
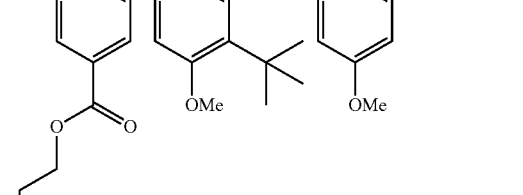
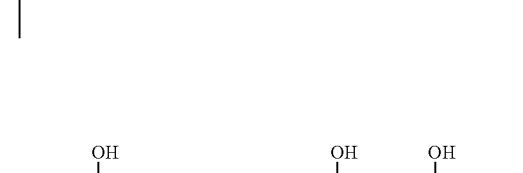
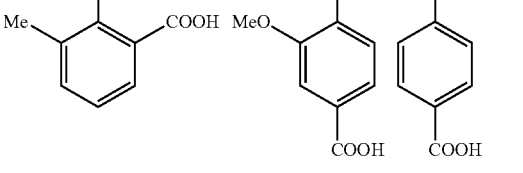

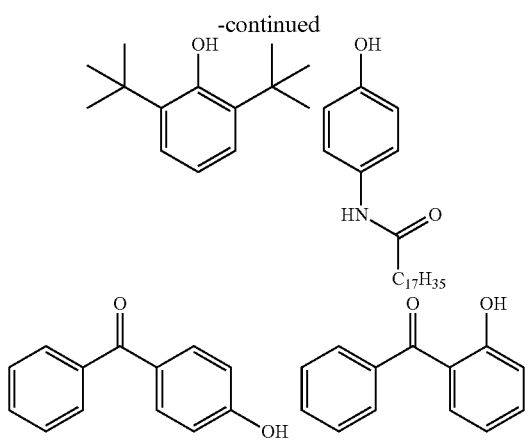

In certain embodiments, the aldehyde used in the methods of the present invention is selected from the group consisting of formaldehyde, acetaldehyde, valeraldehyde, butyraldehyde, isovalrealdehyde, 2-methyl butanal, benzaldehyde, cyclohexanecarbaldehyde, 3-methylcyclohexanecrabaldehyde, glyceraldehyde, glucose aldehyde.

In certain embodiments, the methods of the present invention are the product above referred as a substituted phenol-aldehyde polymer. The following scheme (Scheme I-A) illustrate the particular embodiments of this method Scheme I-A

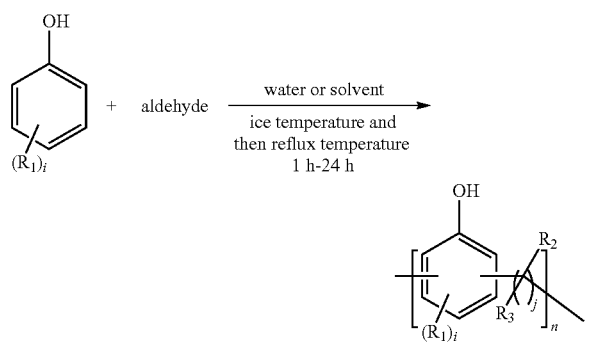

wherein, a substituted phenol is selected from Structural formula XIV, aldehyde is selected from formaldehyde, acetaldehyde, valeraldehyde, butyraldehyde, isovalrealdehyde, 2-methyl butanal, benzaldehyde, cyclohexanecarbaldehyde, 3-methylcyclohexanecrabaldehyde, glyceraldehyde, glucose aldehyde; all of the remaining 925 variables are as described above or Structural formula III, n is an integer from 1 to 1000 or 0 to 100, 0 to 50 or 0 to 25, 0 to 15, or preferably 0 to 10, all of the remaining variables are as described above or Structural formula II.

It is understood the use of phrase 'substituted phenol-aldehyde polymer' refers to the product in Scheme IA.

In yet another embodiment, the method involves adding concentrated sulfuric acid to the reaction mixture of a substituted phenol and an aldehyde in distilled water and keep at the ice-bath temperature.

In yet another embodiment, in the reaction of a substituted phenol and an aldehyde, the ratio of a substituted phenol to a suitable solvent is 1:1-10, 1:1-5, 1:1-3, 1:2 or 1:1 by volume.

In another embodiment, in the method above involves refluxing the reaction mixture under inert atmosphere between 1-48 hours, between 3 and 9 hours, between 6 and 12 hours, or between 12 and 36 hours.

In another embodiment, in the above method involves cooling the reaction mixture to room temperature and separating the product and washing with water.

In yet another embodiment, the reaction solvent for the mixture of a substituted phenol and an aldehyde is selected from toluene, xylene, 1,2-dichloroethane, tetrachloroethylene, dioxane or methylethyl ketone at reflux temperature under inert atmosphere.

In another embodiment, in the above method, an acid added to the reaction mixture of a substituted phenol and an aldehyde in above solvents is selected from hydrochloric acid, p-toluenesulfonic acid, or oxalic acid, solid based acids, phosphoric acid and acetic acid.

In yet another embodiment, in the above method involves reacting alkyl chloride to the above (substituted phenol-aldehyde) product in a suitable solvent first at ice bath temperature and then bring it to the room temperature while stirring the reaction mixtures for 1 to 48 hours, 3 to 12 hours, or 6 to 24 hours.

In yet another embodiment, in the above method involves adding triethyl amine to the reaction mixture.

In yet another embodiment, in the above method involves, the alkyl acid chloride with carbons in the alkyl chain ranging from $C_1$ to $C_{26}$. Preferred alkyl acid chlorides are, $C_8$, $C_{12}$, $C_{14}$, $C_{16}$, or $C_{18}$ linear or branched carbon alkyl acid chlorides.

In other embodiments, the methods of the present invention, when the solvent is used it can be recycled by separating the solvents from the reaction mixture using distillation.

The following schemes illustrate particular embodiments of this method:

Scheme I

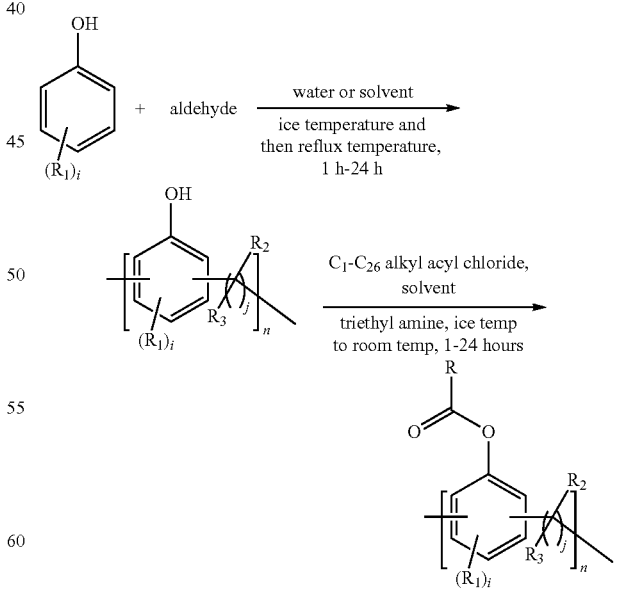

wherein, substituted phenols selected from Structural formula XIV, aldehyde is selected from formaldehyde, acetaldehyde, valeraldehyde, butyraldehyde, isovalrealdehyde, 2-methyl butanal, benzaldehyde, cyclohexanecarbaldehyde, 3-methylcyclohexanecrabaldehyde, glyceraldehyde, glucose aldehyde; all of the remaining variables are as described above or Structural formula III; n is an integer from 1 to 1000 or 0 to 100, 0 to 50 or 0 to 25, 0 to 15, or preferably 0 to 10.

In yet another embodiment the present invention is a method of producing a compound in Scheme I Scheme II

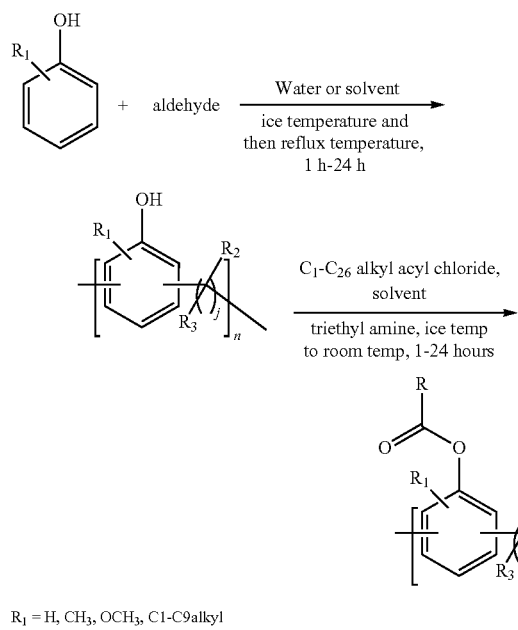

$R_1$ = H, $CH_3$, $OCH_3$, C1-C9alkyl wherein, R is a linear or branched alkyl $C_1$-$C_{26}$ chain, an alkyl $C_{12}$ or an alkyl $C_{16}$ or an alkyl $C_{18}$ or a mixture of alkyl $C_{12}$, $C_{14}$, $C_{16}$ and $C_{18}$ chains; n is an integer from 1 to 1000 or 0 to 100, 0 to 50 or 0 to 25, 0 to 15, or preferably 0 to 10, all of the remaining variables are as described above or Structural formula II.

In yet another embodiment the present invention is a method of producing a compound in Scheme II:

Scheme III

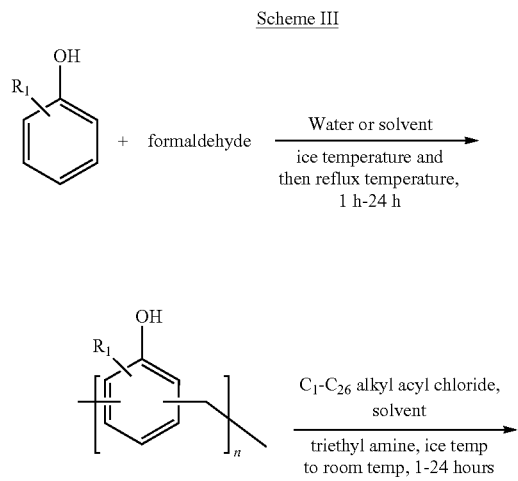

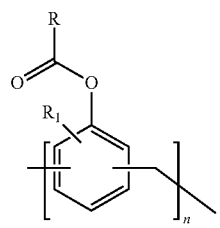

$R_1$ = H, $CH_3$, $OCH_3$, C1-C9alkyl wherein an aldehyde is selected from a group of formaldehyde, acetaldehyde, valeraldehyde, butyraldehyde, isovalraldehyde, or 2-methyl butanal, benzaldehyde; preferably formaldehyde or acetaldehyde; wherein, R is a linear or branched alkyl $C_1$-$C_{26}$ chain, an alkyl $C_{12}$ or an alkyl $C_{16}$ or an alkyl $C_{18}$ or a mixture of alkyl $C_{12}$, $C_{14}$, $C_{16}$ and $C_{18}$ chains; n is an integer from 1 to 1000 or 0 to 100, 0 to 50 or 0 to 25, 0 to 15, or preferably 0 to 10.

In yet another embodiment the present invention is a method of producing a compound in Scheme III:

Scheme IV

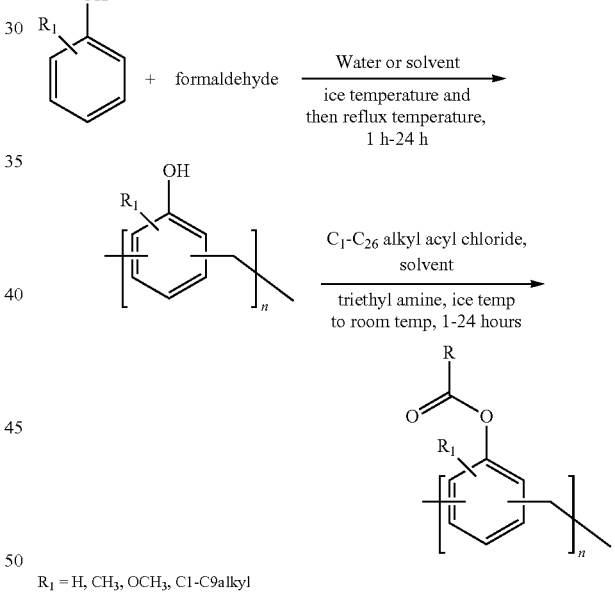

$R_1$ = H, $CH_3$, $OCH_3$, C1-C9alkyl wherein, R is a linear or branched alkyl $C_1$-$C_{26}$ chain, an alkyl $C_{12}$ or an alkyl $C_{16}$ or an alkyl $C_{18}$ or a mixture of alkyl $C_{12}$, $C_{14}$, $C_{16}$ and $C_{18}$ chains; n is an integer from 1 to 1000 or 0 to 100, 0 to 50 or 0 to 25, 0 to 15, or preferably 0 to 10, all of the remaining variables are as described above or Structural formula II.

In yet another embodiment the present invention is a method of producing a compound in Scheme IV where in a substituted phenol is selected from Structural formula XIV.

In another embodiment, the present invention is a method of producing a compound in Scheme IV wherein a substituted phenol is selected from Structural formula XIV.

Scheme V

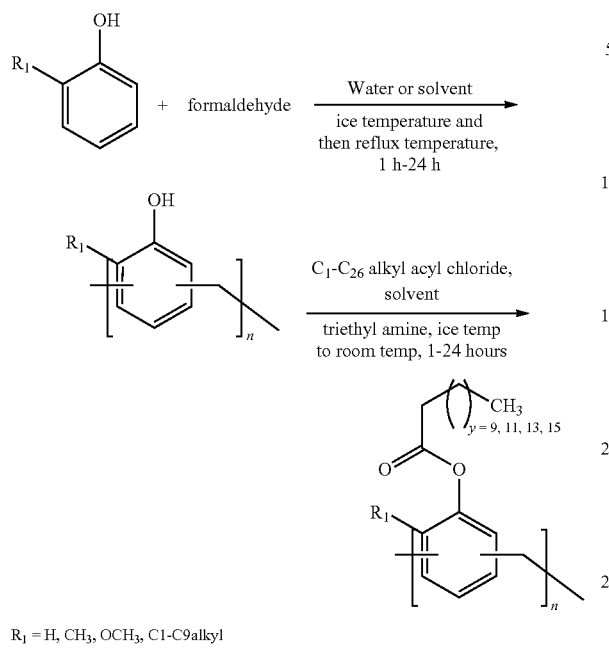

$R_1 = H, CH_3, OCH_3, C1-C9\text{alkyl}$

In another embodiment the present invention is a method of producing a compound in Scheme V wherein a substituted phenol is a phenol, ortho-cresol or a mixture of ortho, meta, para-cresols, or o-methoxyphenol, and R is a linear alkyl C12 or a C16 or C18 or a mixture of alkyl $C_{12}$, $C_{14}$, $C_{16}$ and $C_{18}$ chains, and n is an integer from 1 to 1000 or 0 to 100, 0 to 50 or 0 to 25, 0 to 15, or preferably 0 to 10.

In another embodiment the present invention is a process of producing a compound in Structural Formulas IV:

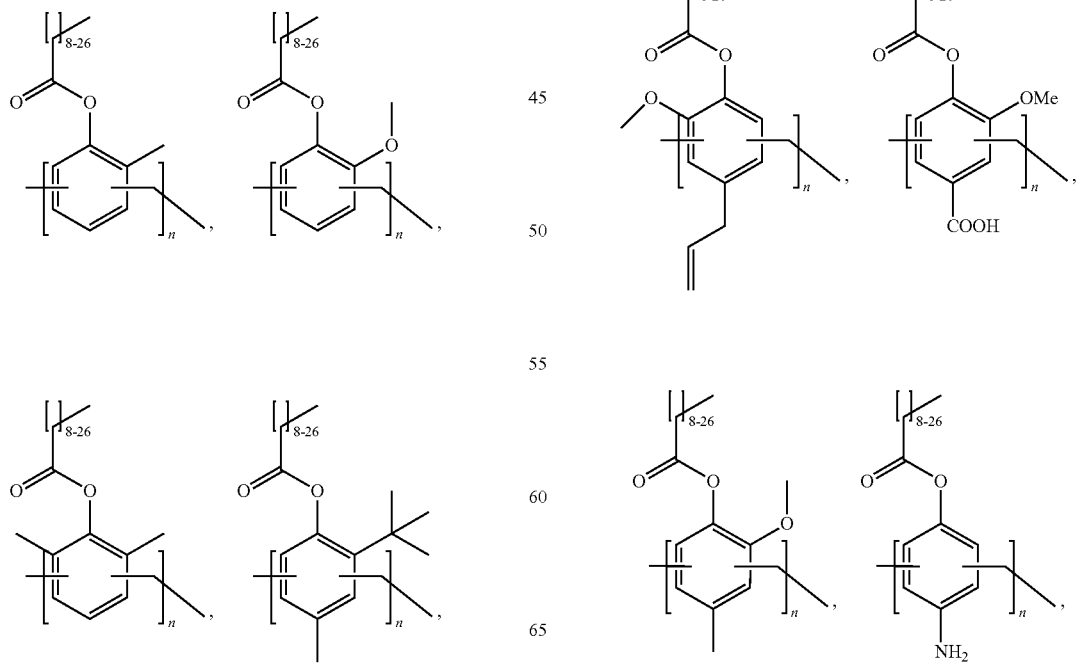

-continued

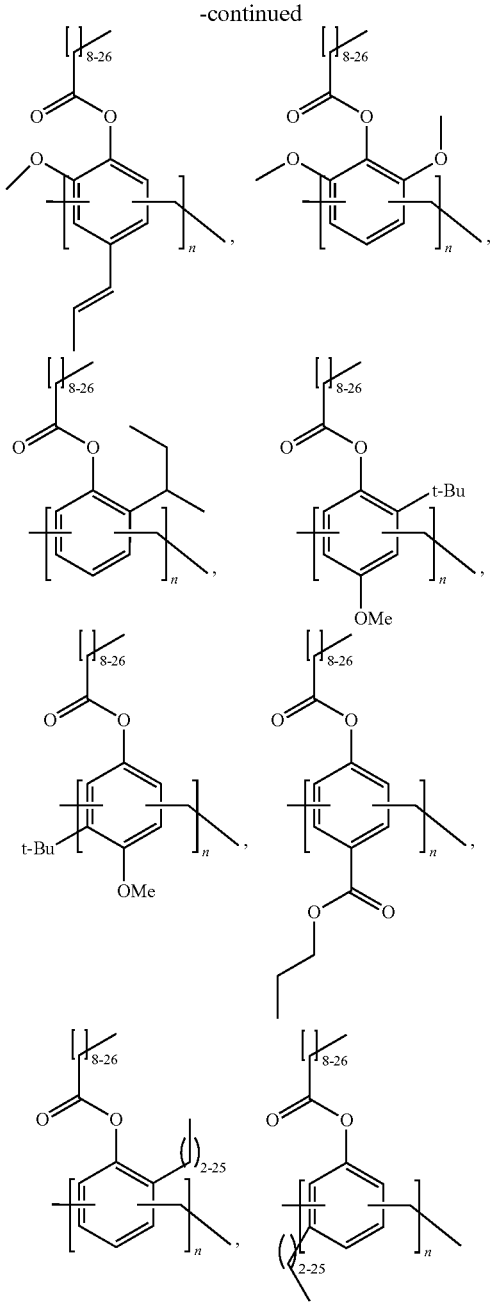

wherein n is an integer from 0 to 100 or 0 to 50 or 0 to 25, 0 to 15, or preferably 0 to 10

In certain embodiments of this invention relates to a macromolecular corrosion inhibitor that is a polymer which is the reaction product of the starting materials comprising a substituted phenol and an aldehyde and is further reacted with an alkenyl succinic anhydride to form an isomerized half ester product having a free carboxylic acid group in the repeating unit.

In another embodiment, the substituted phenol is selected from the Structural formulas XIV and an aldehyde is selected from formaldehyde, acetaldehyde, valeraldehyde, butyraldehyde, isovalrealdehyde, 2-methyl butanal, benzaldehyde, cyclohexanecarbaldehyde, 3-methylcyclohexanecrabaldehyde, glyceraldehyde, glucose aldehyde.

In one embodiment, an alkenyl succinic anhydride is selected from the group consisting of DDSA, ODSA, OSA, PIBSA form an isomerized half ester product having free carboxylic acid groups in the alkenyl chain of the repeating group.

In yet another embodiment the present invention is a method of producing an isomerized compound in Scheme VI:

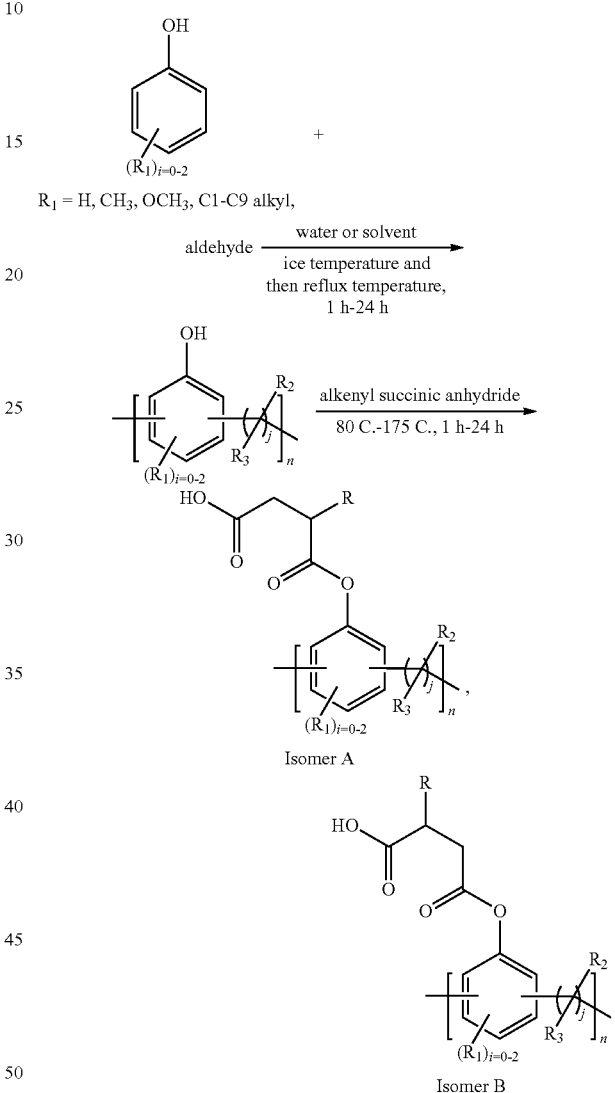

wherein an alkenyl succinic anhydride is selected from the group consisting of DDSA, ODSA, OSA, PIBSA to form an isomerized half ester product having free carboxylic acid groups in the alkenyl chain of the repeating group, and n is an integer from 1 to 1000 or 0 to 100, 0 to 50 or 0 to 25, 0 to 15, or preferably 0 to 10 and all of the remaining variable are as described above or Structural formula XI and remaining variables are as described for structural formula II.

In yet another embodiment the present invention is a method of producing a compound with a mixture of isomers (A) and (B) in Scheme VI.

In yet another embodiment the present invention is a method of producing a compound with mixture of isomerized (A) and (B) in Structural formulas XII Structural Formulas XII

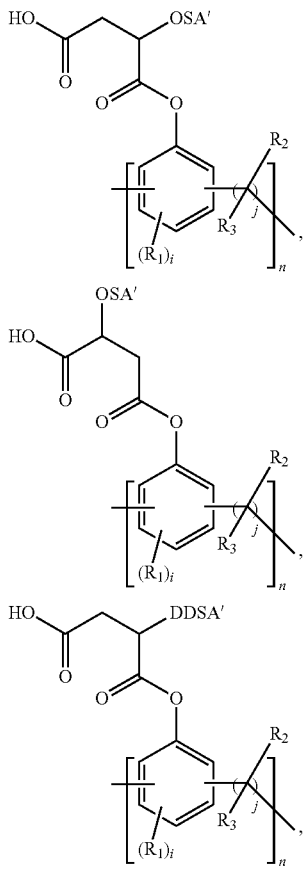

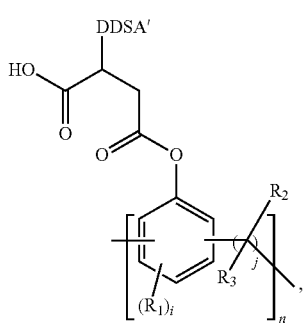

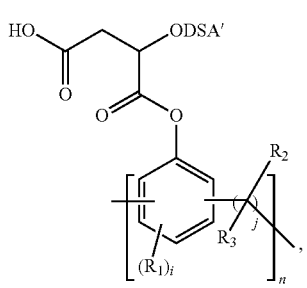

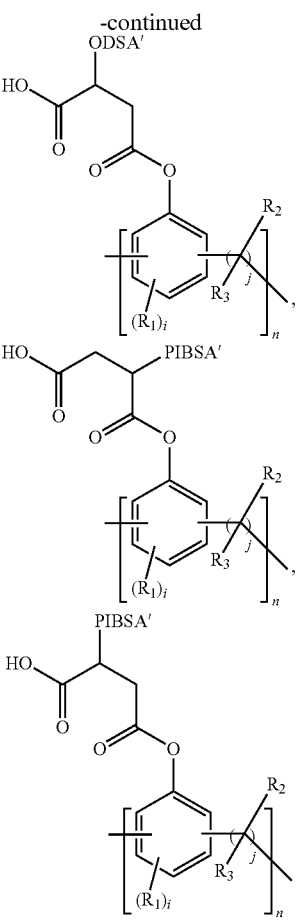

wherein OSA', DDSA', ODSA', PIBSA' are alkenyl chain portion of OSA, octenyl succinic anhydride; DDSA, dodecenyl succinic anhydride; ODSA, octadecenyl succinic anhydride; PIBSA, polyisobutylene succinic anhydride (low molecular weight, 300-1500 molecular weight), respectively; and n is an integer from 1 to 1000 or 0 to 100, 0 to 50 or 0 to 25, 0 to 15, or preferably 0 to 10, and all of the remaining variables are as described above or Structural formula II.

In another embodiment the present invention is a method of producing a compound with mixture of isomers (A) and (B) in Structural formulas XII wherein the mixture of a substituted phenol-aldehyde polymer reacted with an alkenyl succinic anhydride selected from the group consisting of DDSA, dodecenyl succinic anhydride; ODSA, octadecenyl succinic anhydride; PIBSA, polyisobutylene succinic anhydride (low molecular weight, 300-1500 molecular weight) reaction temperatures between 80° C. to 175° C. between 1 and 24 hours, between 3 to 12 hours, or between 6-24 hours.

In yet another embodiment the present invention is a method of producing a compound with mixture of isomers (A) and (B) in Structural formulas XII wherein a substituted phenols is selected from Structural formulas XIV and an aldehyde is selected from an aldehyde is selected from formaldehyde, acetaldehyde, valeraldehyde, butyraldehyde, isovalrealdehyde, 2-methyl butanal, benzaldehyde, cyclohexanecarbaldehyde, 3-methylcyclohexanecrabaldehyde, glyceraldehyde, glucose aldehyde.

In yet another embodiment the present invention is a method of producing a compound with a mixture of isomers (A) and (B) in Structural formulas XII wherein an aldehyde is formaldehyde or acetaldehyde.

In yet another embodiment the present invention is a method of producing a compound with a mixture of isomerized structures in Structural formulas XII.

In yet another embodiment of this invention relates to a macromolecular corrosion inhibitor that is a polymer which is the reaction product of the starting materials comprising a substituted phenol and an aldehyde are further reacted with an alkylene oxide (e.g. propylene oxide) to form a phenol-derived alcohol in the repeating unit and is further reacted with an alkyl acid. Generally, Fischer esterification of a phenol with an alkyl acid is not an efficient one. However, the reaction is efficient if the phenolic-OH is converted to an alkyl alcohol and is further reacted with a linear or branched $C_1$-$C_{26}$ alkyl acid. The substituted phenol is selected from the structural formulas (XIV) and an aldehyde is selected from formaldehyde, acetaldehyde, valeraldehyde, butyraldehyde, isovalrealdehyde, 2-methyl butanal, benzaldehyde, cyclohexanecarbaldehyde, 3-methylcyclohexanecrabaldehyde, glyceraldehyde, glucose aldehyde.

In certain embodiments, the methods of the present invention to produce a compound that includes the esterification of a substituted phenol-aldehyde polymer (Schemes I-A, VII-A) by reacting with an oleoyl chloride followed by reacting with maleic anhydride and finally reacted with an alkyl alcohol to form an isomerized alkenyl chain containing half acid ester groups (Scheme VII-I).

In one embodiment of the method of producing a compound with substituted phenol group consisting of a substituted phenol is selected from Structural formula XIV; and an aldehyde is selected from formaldehyde, acetaldehyde, valeraldehyde, butyraldehyde, isovalrealdehyde, 2-methyl butanal, benzaldehyde, cyclohexanecarbaldehyde, 3-methylcyclohexanecrabaldehyde, glyceraldehyde, glucose aldehyde; all of the remaining variables are as described above or Structural formula III.

In certain embodiments of the present invention is a method of producing an isomerized compound is represented by Structural Formula III wherein, R is a $C_1$-$C_{24}$ linear or branched alkyl chain, an isomerized alkenyl chain or a mixture of isomerized alkenyl chains represented by

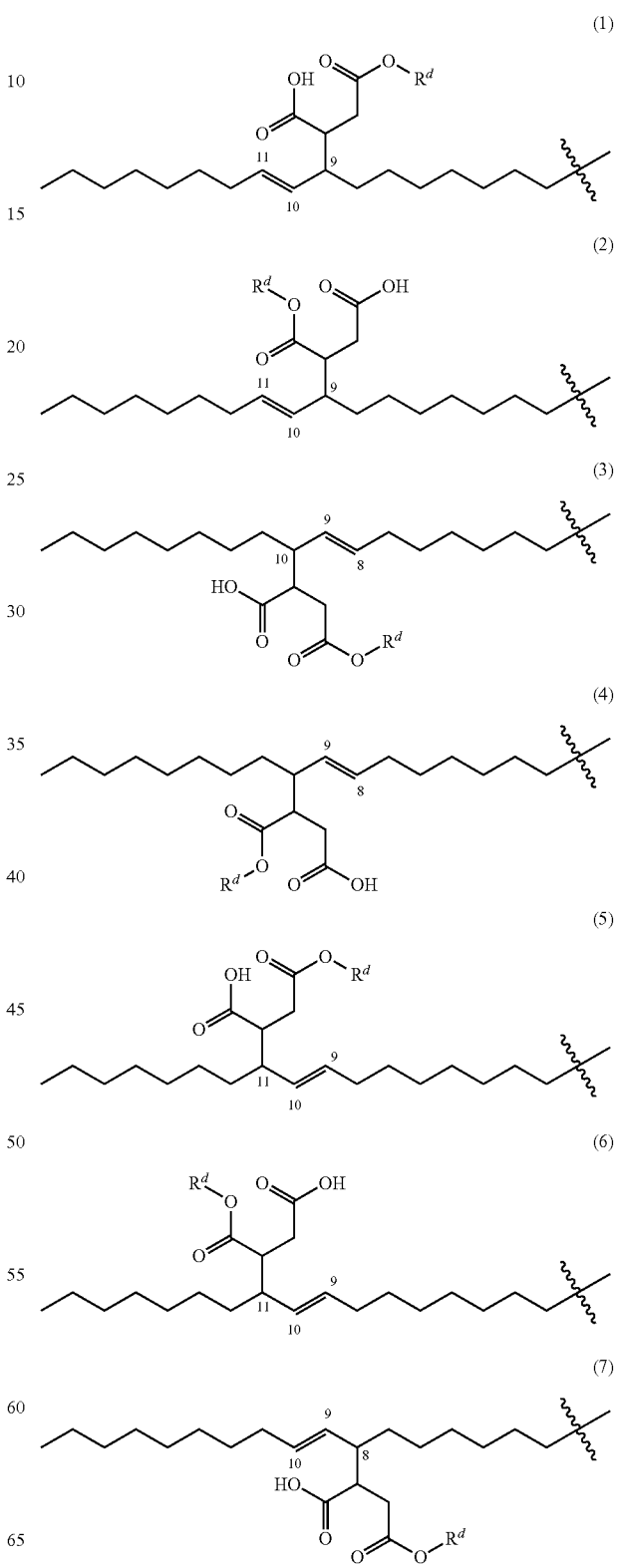

65
-continued

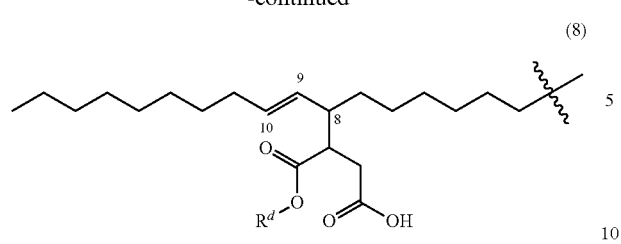

wherein $R^d$ is a linear or branched $C_1$-$C_{24}$ alkyl chain; or an isomerized structure or a mixture of isomerized (A) and (B)

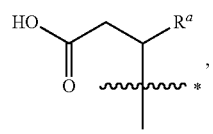

(A)

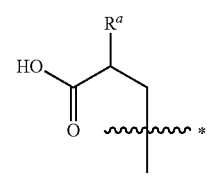

(B)

wherein $R^a$ is a $C_1$-$C_{24}$ linear or branched alkenyl chain, an alkenyl chain portion of OSA, octenyl succinic anhydride; DDSA, dodecenyl succinic anhydride; ODSA, octadecenyl succinic anhydride; PIBSA, polyisobutylene succinic anhydride (low molecular weight, 300-1500 molecular weight, and $R_1$ is selected from the group consisting of

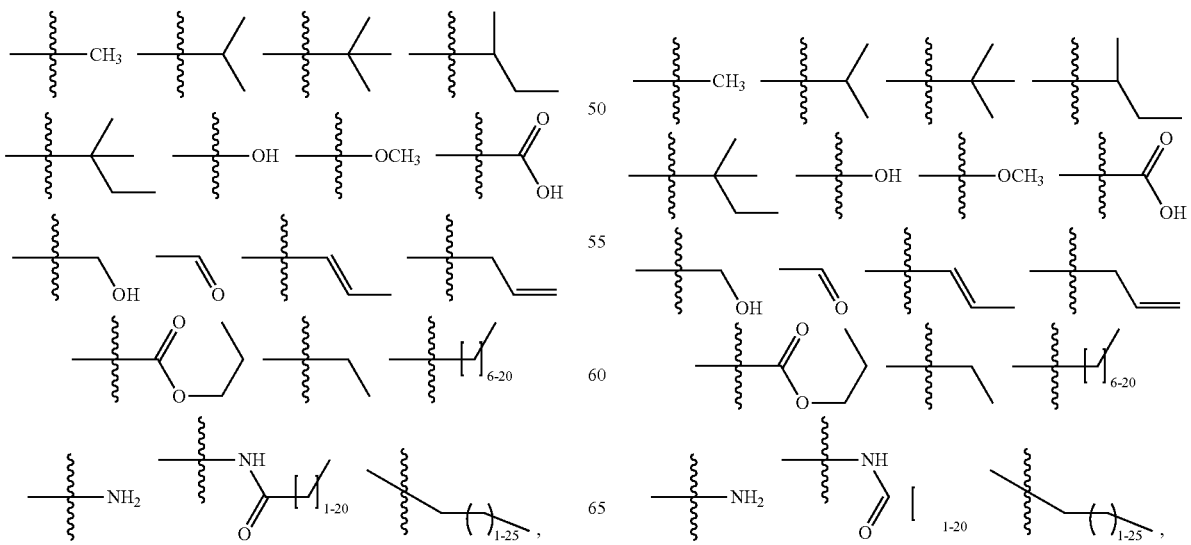

66
-continued

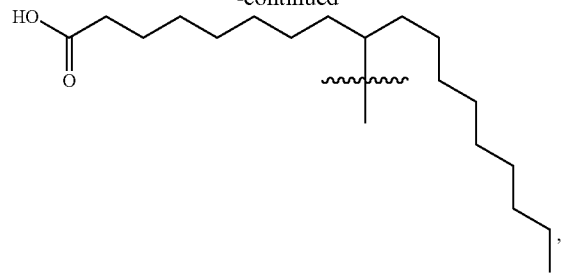

n is an integer from 1 to 1000 or 1 to 100, 1 to 50 or 1 to 25, 1 to 15, or preferably 1 to 10, a method comprising:

(a) Reacting in a solvent at reflux a phenol having the following formula:

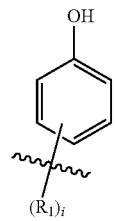

wherein $R_1$ is selected from the group consisting of an isomerized alkyl acid chain or a mixture of isomerized alkyl acid chains as shown below

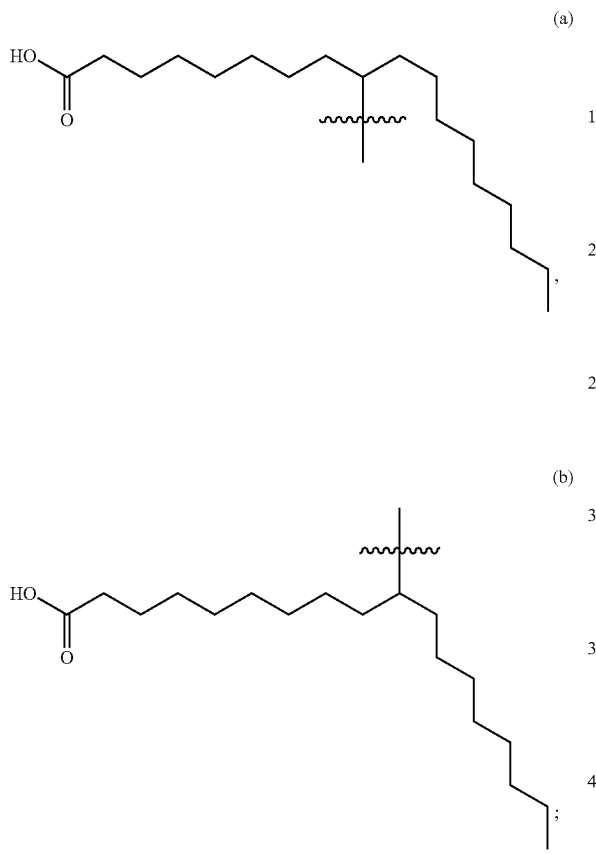

with formaldehyde, (b) The product in (a) is reacting with an oleoyl chloride or alkyl acyl chloride at ice temperature to room temperature for 1 hour to 24 hours, or an alkenyl succinic anhydride is selected from the group of OSA, octenyl succinic anhydride; DDSA, dodecenyl succinic anhydride; ODSA, octadecenyl succinic anhydride; PIBSA, polyisobutylene succinic anhydride (low molecular weight, 300-1500 molecular weight) at 80° C. to 150° C. for 1 to 24 hours, (c) The product in (b) is reacting with maleic anhydride at 170° C.-210° C. for 1 hour to 24 hours if the reactant used in (b) is an oleoyl chloride, and then finally (d) The succinic anhydride group of product in (c) is reacting with a $C_1$-$C_{24}$ linear or branched or cyclic alcohol at 80° C. to 150° C., if the reactant used in (b) is an oleoyl chloride.

In yet another embodiment the present invention is a method of producing an isomerized compound in Scheme VII:

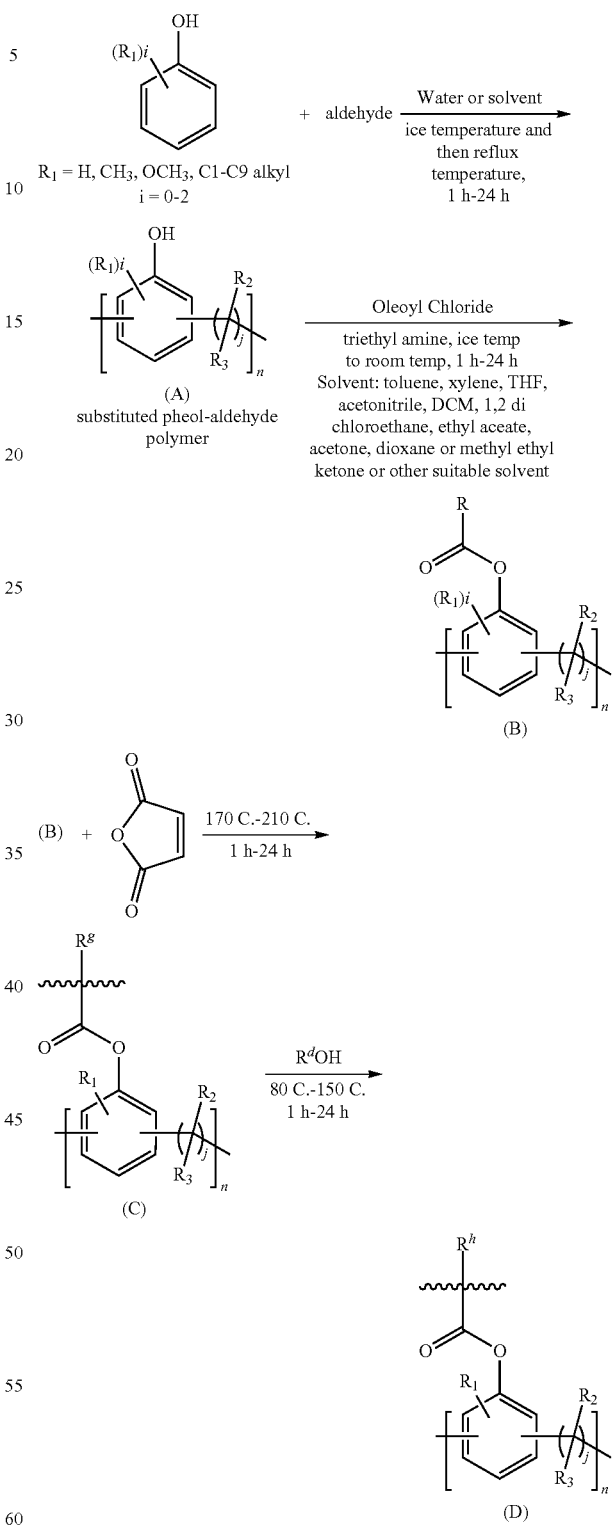

wherein variables are described for structural formula III, and $R^d$ is an isomerized alkenyl chain, and n is an integer from 1 to 1000 or 0 to 100, 0 to 50 or 0 to 25, 0 to 15, or preferably 0 to 10, (1)

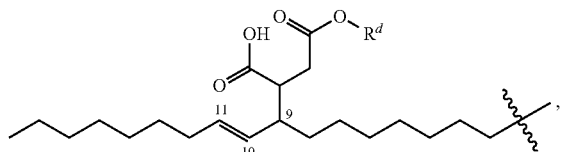

(2)

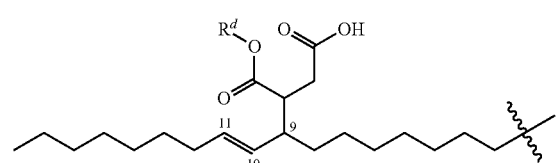

(3)

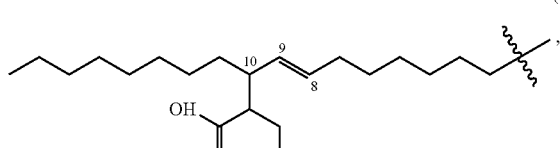

(4)

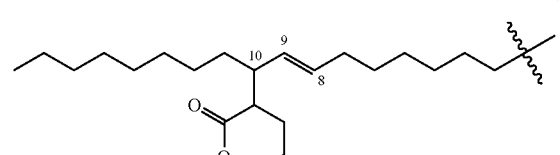

(5)

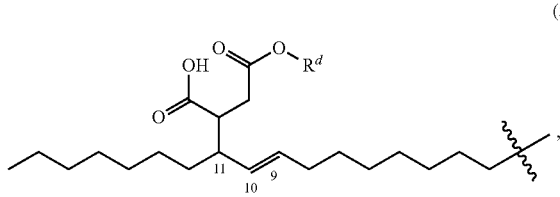

(6)

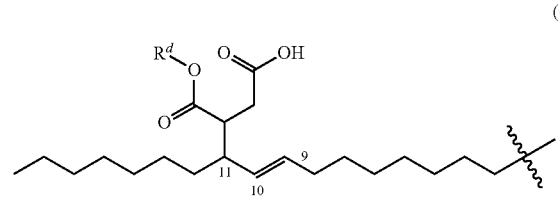

(7)

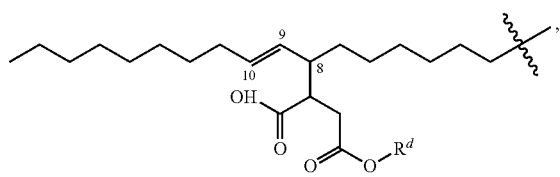

-continued (8)

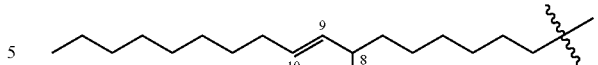

wherein $R^d$ is an isomerized alkenyl chain wherein $R^g$ is an isomerized oleate succinic anhydride chain (Scheme VII-I), $R^d$ is an isomerized oleate half-acid ester chain.

In yet another embodiment the present invention is a method of producing an isomerized compound in Scheme VIII:

Scheme VIII

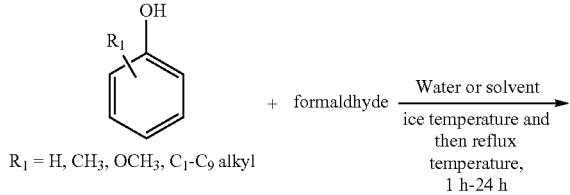

$R_1$ = H, CH$_3$, OCH$_3$, C$_1$-C$_9$ alkyl (A) substituted pheol-aldehyde polymer Oleoyl Chloride
triethyl amine, ice temp
to room temp, 1 h-24 h
Solvent: toluene, xylene, THF,
acetonitrile, DCM, 1,2 di
chloroethane, ethyl aceate,
acetone, dioxane or methyl ethyl
ketone or other suitable solvent

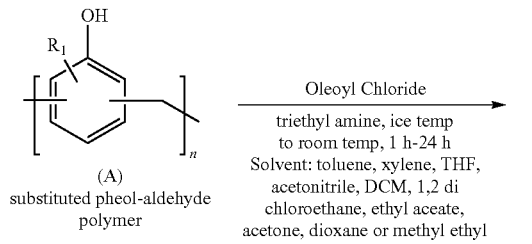

(B)

(B) + 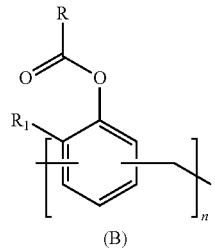 $\xrightarrow{\text{170 C.-210 C.}}{\text{1 h-24 h}}$ (C)

$\xrightarrow{R^dOH}{\text{80 C.-150 C.}\atop\text{1 h-24 h}}$

-continued

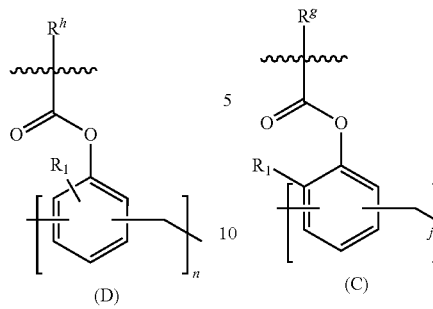

(D)

wherein R$^g$ is an isomerized oleate succinic anhydride chain (Scheme VII-I),

R$^d$ is an isomerized oleate half-acid ester, and n is an integer from 1 to 1000 or 0 to 100, 0 to 50 or 0 to 25, 0 to 15, or preferably 0 to 10.

In yet another embodiment the present invention is a method of producing an isomerized compound in Scheme IX:

Scheme IX

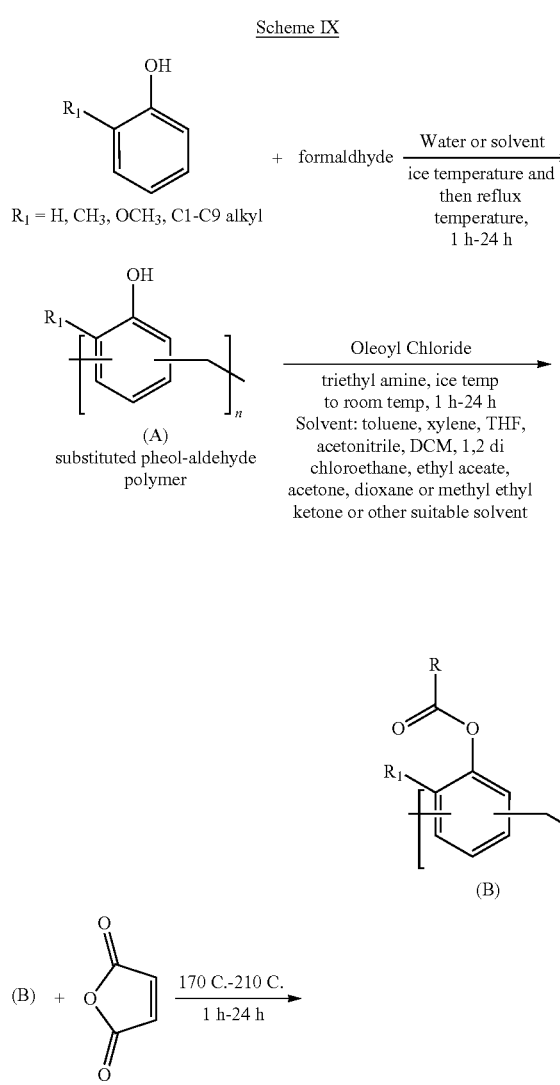

-continued

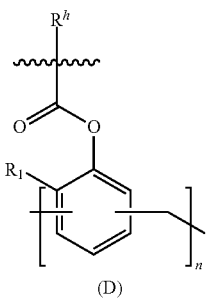

(D)

wherein R$^g$ is an isomerized oleate succinic anhydride chain (Scheme VII-I),

R$^d$ is an isomerized oleate half-acid ester chain; n is an integer from 1 to 1000 or 0 to 100, 0 to 50 or 0 to 25, 0 to 15, or preferably 0 to 10.

In one embodiment of the present invention is directed to forming a polymer by reacting a substituted phenol with a formaldehyde followed by post esterification of the reaction with oleoyl chloride is further reacted with maleic anhydride at reaction temperatures between 170° C. and 210° C. between 1 and 24 hours, between 3 to 12 hours, or between 6-24 hours.

In yet another embodiment, in the above method, the molar ratio of the reaction product (of a substituted phenol with formaldehyde followed by post esterification of the reaction with oleoyl chloride) and maleic anhydride is 1:0.8, 1:0.9, 1:1.0, or 1:2.

In yet another embodiment, in the above method, a suitable solvent is selected from the group consisting of toluene, xylene, chlorobenzene, dimethyl formamide, dimethyl sulfoxide, 1,2-dichlorobenzene, dimethylsuccinate, diisobutyl adipate and diisobutyl glutarate.

In yet another embodiment, in the above method, the weight ratio of a solvent and the reaction product (a substituted phenols reacted with formaldehyde followed by post esterification of the reaction with oleoyl chloride further reacted with maleic anhydride) is 0.1 to 1.0:1.0

In yet another embodiment, in the above method involves distilling the solvent from the reaction mixture.

In one embodiment of the present invention is directed to forming a polymer by reacting the 1165 reaction product (a substituted phenols reacted with formaldehyde followed by post esterification of the reaction with oleoyl chloride further reacted with maleic anhydride) is further reacted with an alkyl alcohol to form half acid ester selected from the group consisting of linear or branched C$_1$-C$_{24}$ chain at reaction temperatures between 80° C. and 150° C. between 1 and 24 hours, between 3 to 12 hours, or between 6-24 hours.

In another embodiment of the present invention is a method of producing a mixture of isomerized compounds in Scheme X:

Scheme X
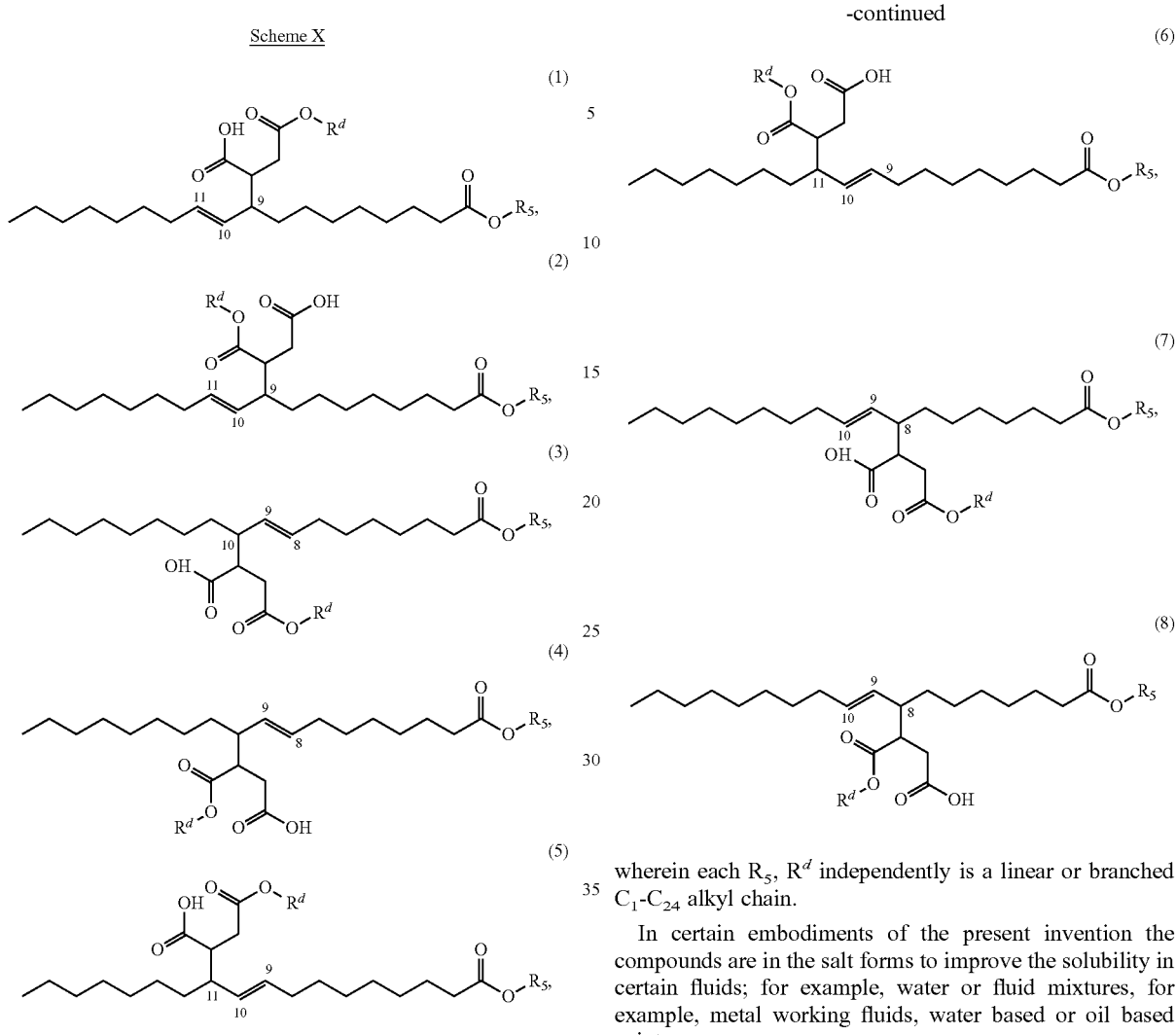
wherein each $R_5$, $R^d$ independently is a linear or branched $C_1$-$C_{24}$ alkyl chain.
In certain embodiments of the present invention the compounds are in the salt forms to improve the solubility in certain fluids; for example, water or fluid mixtures, for example, metal working fluids, water based or oil based paints.
Scheme XI
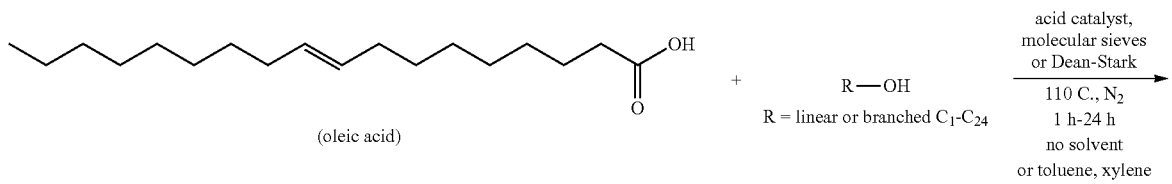
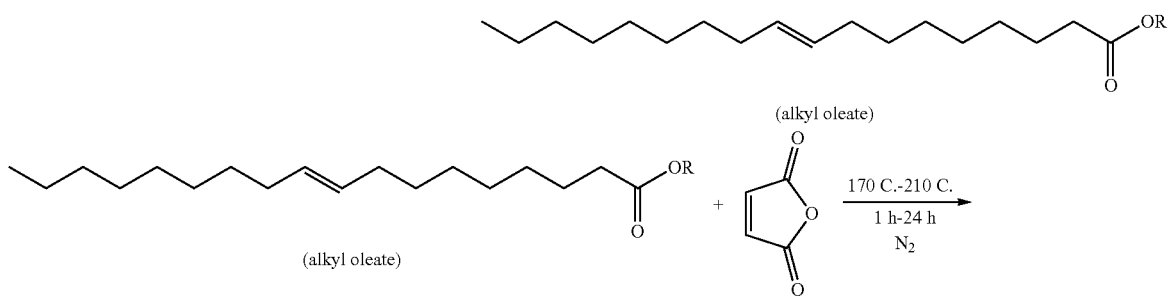

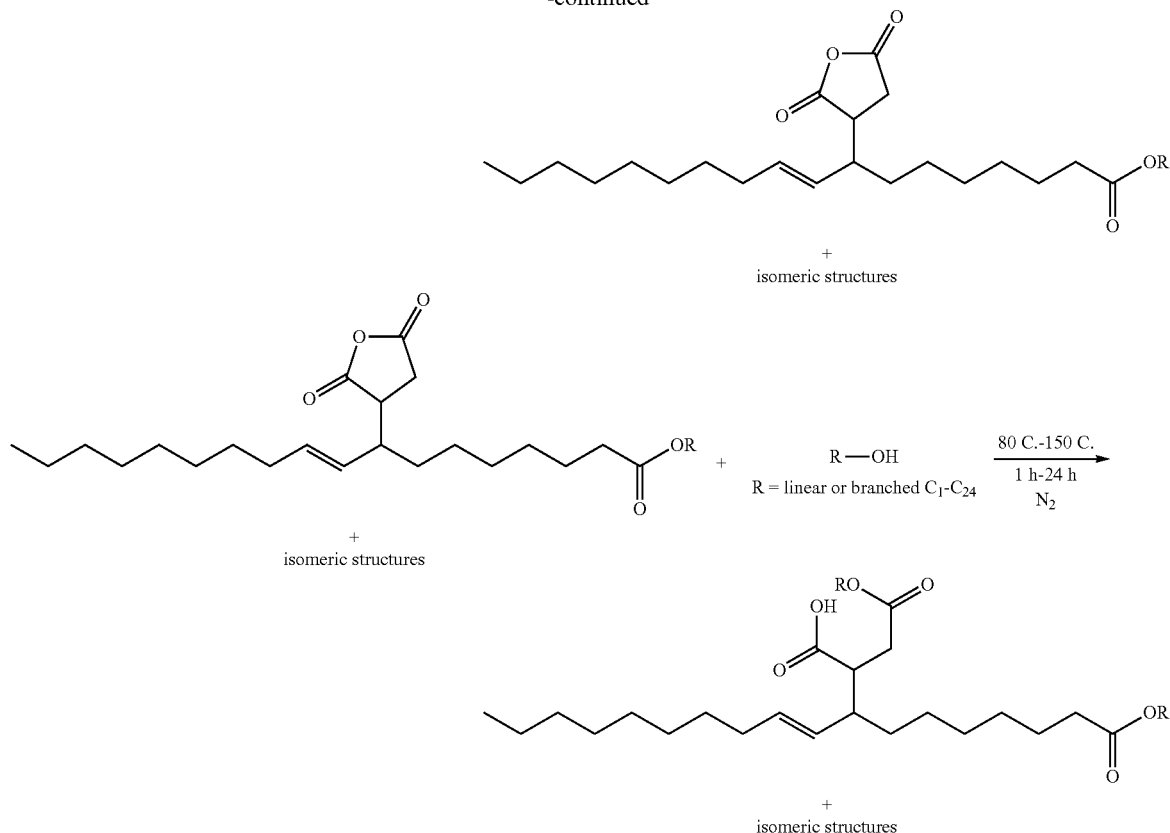
In another embodiment the present invention is a method of producing a mixture of the isomerized compounds in Scheme XII:
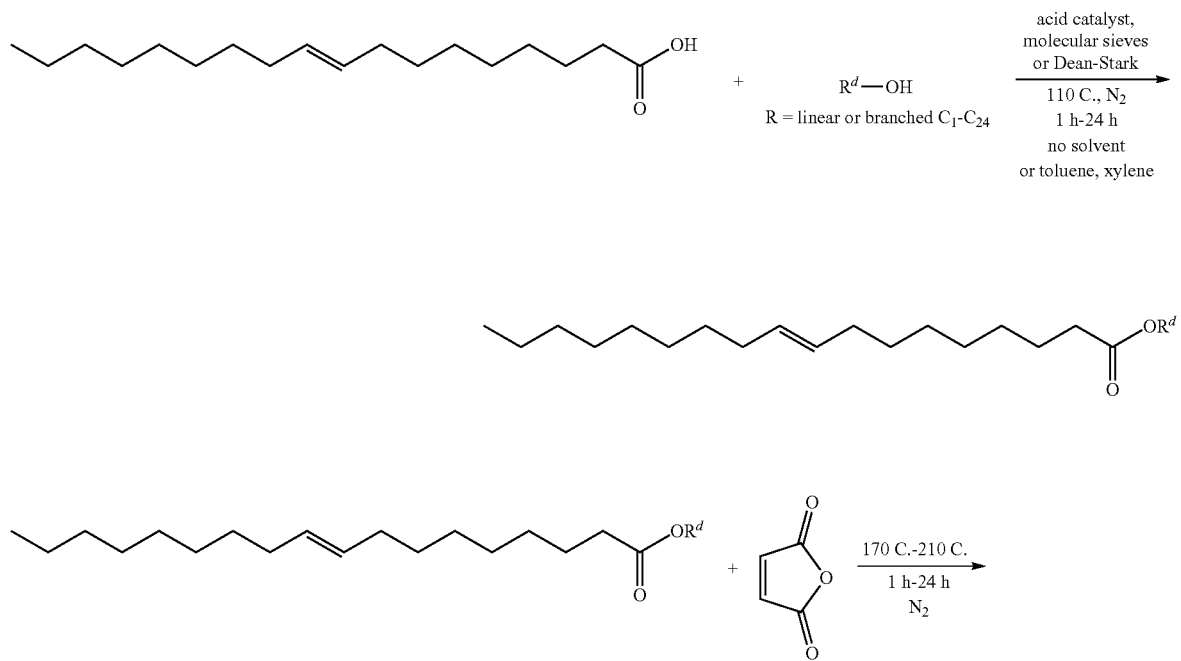

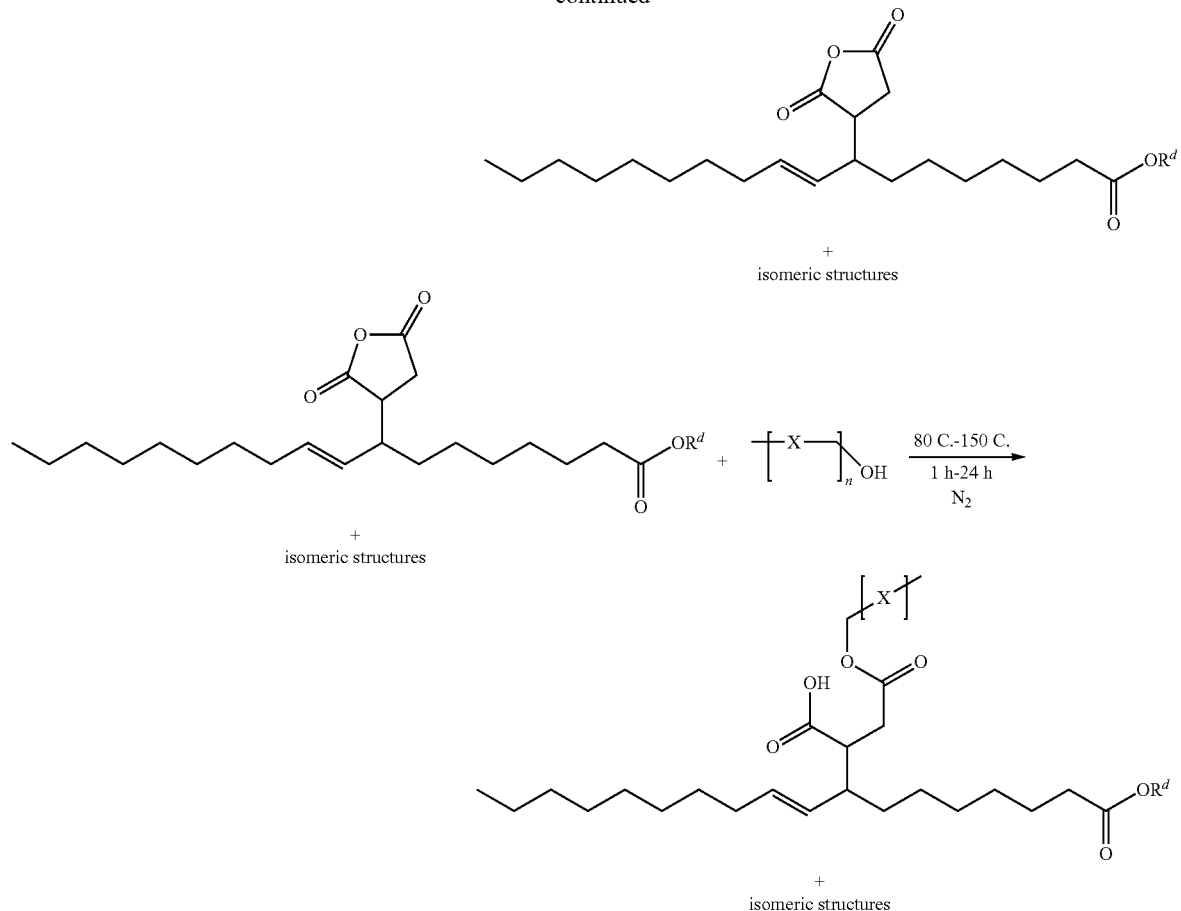
wherein $R^d$ is an $C_1$-$C_{24}$ alcohol.
In another embodiment of the present invention is a method of making a compound having the following structure with a mixture of isomeric structures:
wherein [X] is
R is an isomerized alkenyl chain represented by
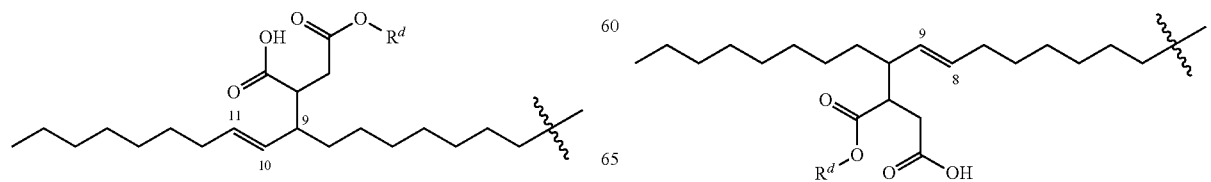

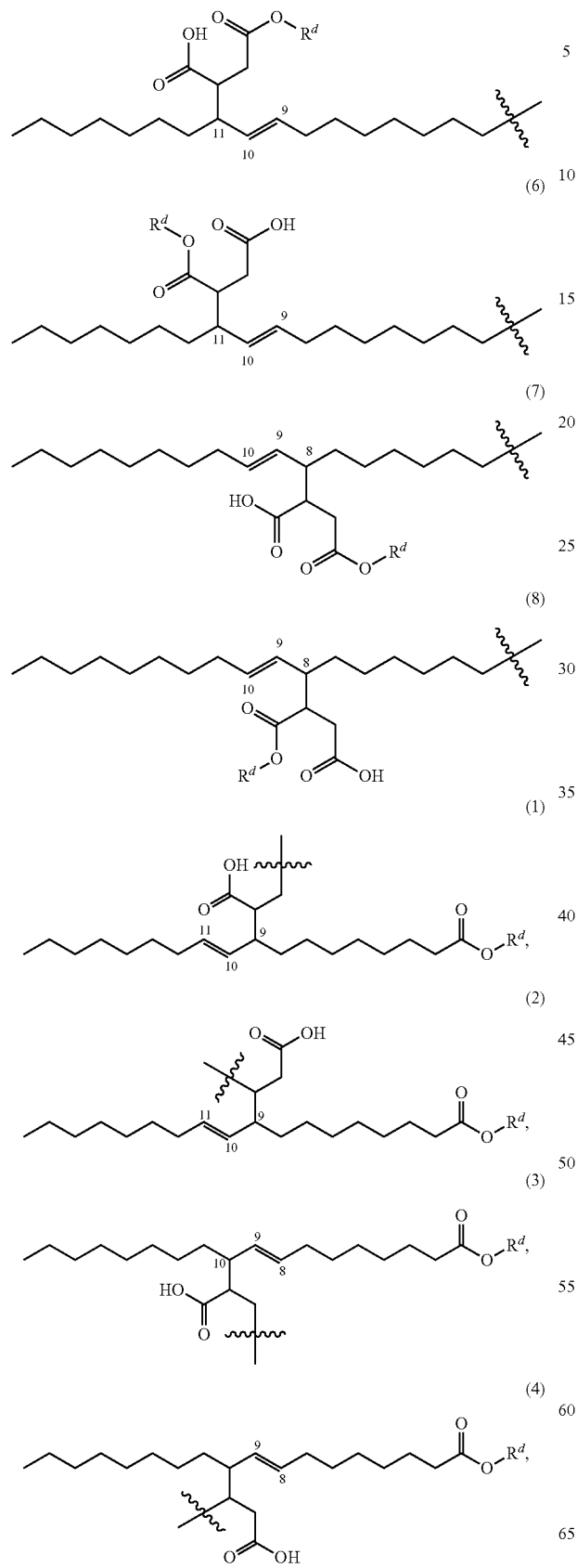

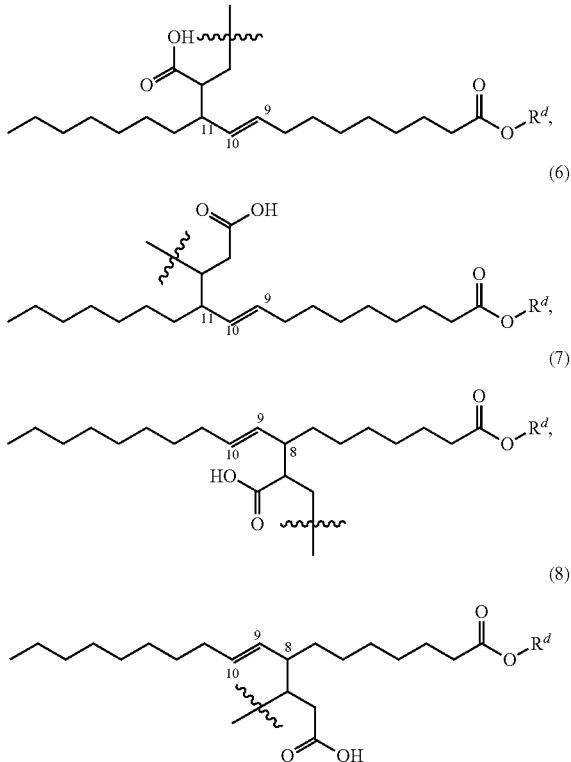

wherein $R^d$ independently is a linear or branched $C_1$-$C_{24}$ alkyl chain, the method comprising:
a. reacting in a solvent or in bulk an oleic acid with a $C_1$-$C_{24}$ linear or branched or cyclic alcohol,
b. the product in (a) is reacting with a maleic anhydride at 170° C.-210° C. for 1 hour to 24 hours, and finally
c. the succinic anhydride group of product in (b) is reacting with an X at 80° C. to 150° C.

As used here, the terms "lubricants" and "lubricant oils" can be used interchangeably. Examples of lubricants suitable for use in the compositions and methods of the present invention 1210 include, but are not limited to: i) petroleum based oils (Group I, II and III), ii) synthetic oils (Group IV, V) and iii) biolubricant oils (vegetable oils such as canola, soybean, high oleic canola, high oleic soybean oil, corn oil, castor oil, jatropha, etc.). Group I oils, as defined herein are solvent refined base oils. Group II oils, as defined herein are modern conventional base oils made by hydrocracking and early wax isomerization, or hydroisomerization technologies and have significantly lower levels of impurities than Group I oils. Group III oils, as defined herein are unconventional base oils. Groups I-III differ in impurities, and viscosity index as is shown in Kramer et al. "The Evolution of Base Oil Technology" *Turbine Lubrication in the 21$^{st}$ Century* ASTM STP #1407 W. R. Herguth and T. M. Wayne, Eds., American Society for Testing and Materials, West Conshohocken, Pa., 2001 the entire contents of which are incorporated herein by reference. Group IV oils as defined herein are "synthetic" lubricant oils, including, for example, poly-alpha olefins (PAOs). Biolubricants, as defined herein, are lubricants which contain at least 51% biomaterial (see Scott Fields, Environmental Health Perspectives, volume 111, number 12, September 2003, the entire contents of which are incorporated herein by reference). Other examples of lubricant oils can be found in Melvyn F. Askew "Biolubricants-Market Data Sheet" IENICA, August 2004 (as part of the IENICA work stream of the IENICA-INFORRM project); Taylor et al. "Engine lubricant Trends Since 1990" paper accepted for publication in the Proceedings I. Mech. E. Part J, Journal of Engineering Tribology, 2005 (Vol. 219 p 1-16); and Desplanches et al. "Formulating Tomorrow's Lubricants" page 49-52 of The Paths to Sustainable Development, part of special report published in October 2003 by Total; the entire contents of each of which are incorporated herein by reference. Biolubricants are often but not necessarily, based on vegetable oils. Vegetable derived, for example, from rapeseed, sunflower, palm, and coconut can be used as biolubricants. They can also be synthetic esters which may be partly derived from renewable resources. They can be made from a wider variety of natural sources including solid fats and low grade or waste materials such as tallows. Biolubricants in general offer rapid biodegradability and low environmental toxicity.

As used herein, Group I, II and III oils are petroleum base stock oil. The petroleum industry differentiates their oil based on viscosity index and groups them as Group I, II and III. The synthetic oils are Group IV and Group V. Synthetic oils include hydrocarbon oil. Hydrocarbon oils include oils such as polymerized and interpolymerized olefins (polybutylenes, polypropylenes, propylene isobutylene copolymers, ethylene-olefin copolymers, and ethylene-alpha olefin copolymers, for example). Poly alpha olefin (PAO) oil base stocks are commonly used synthetic hydrocarbon oil. By way of example, PAOs derived from $C_8$, $C_{10}$, $C_{12}$, $C_{14}$ olefins or mixtures thereof may be utilized. In certain embodiments, PAO is a bio-based oil. In certain embodiments, synthetic oils are polyolesters for example diesters, polyolesters such as neopentyl glycols (NPGs), trimethylolpropanes (TMPs), penterythritols (PEs), and dipentaerythritols (DiPEs). In other embodiments, synthetic oils include monoesters and trimellitates. In other embodiments, synthetic oils include polyalkylene glycols (PAGs). In general, synthetic esters described herein are obtained by reacting one or more polyhydric alcohols with alkyl acids. Polyhydric alcohols preferably include the hindered polyols (such as the neopentyl polyols, e.g., neopentyl glycol, trimethylol ethane, 2-methyl-2-propyl-1,3-propanediol, trimethylol propane, pentaerythritol, and dipentaerythritol) and alkyl acids include least about 4 carbon atoms, preferably $C_5$ to $C_{26}$ acids such as saturated straight chain fatty acids including caprylic acid, capric acid, lauric acid, myristic acid, palmitic acid, stearic acid, arachic acid, and behenic acid, or the corresponding branched chain fatty acids or unsaturated fatty acids such as oleic acid, or mixtures of any of these materials.

In certain embodiments of the present invention, mixtures of synthetic (Groups IV and V) and bio-oils or petroleum based oils (Groups I, II, III) and biooils, or petroleum based oils and synthetic oils, or mixtures of bio-oils, synthetic oils and petroleum base oils may be used.

In certain embodiments of the present invention, 0.001% to 10% by weight of the corrosion inhibitors of the present invention is added to lubricant oils. In certain other embodiments of the present invention, 10% to 5% by weight of the corrosion inhibitors of the present invention are added to lubricant oils. In certain other embodiments of the present invention, 0.001% to 2% by weight of the corrosion inhibitors of the present invention is added to lubricant oils. In certain other embodiments of the present invention, 0.001% to 0.5% by 1265 weight of the corrosion inhibitors of the present invention is added to lubricant oils. This percentage varies depending upon their end application and type of the base oil.

In certain embodiments of the present invention, the corrosion inhibitors of the present invention are usually added to lubricant oils with stirring at between 0 and 100° C., between 20 and 80° C. or between 40-60° C. 1270 In certain embodiments of the present invention, the corrosion inhibitors of the present invention are usually added to lubricant and fuel oils (based on petroleum, synthetic, and/or bio-based oils) (examples, gasoline, diesel, biodiesel (B10, B20, up to B100 where numbers after letter B corresponds to percentage of fatty acid methyl esters (FAME) content in diesel) used in automotives, and industrial applications such as but not limited to transmission fluid, engine oil, break oil, metal working fluids, greases, gear oils, hydraulic fluids, transformer oils, elevator oils wire and rope oils, drilling oils, turbine oils used for hydro-power turbines, aviation turbines, wind turbines, metal working fluids, etc.

In certain embodiments, the mixture of corrosion inhibitors of the present invention is preferred due to improved solubility characteristics as compared to a single component corrosion 1280 inhibitor.

In yet other embodiments of the present invention of corrosion inhibitors have significantly improved solubility characteristics in petroleum (Group I-V oils), bio-based oils and bio-oils. This is mainly attributed to the design of the molecules of the current invention containing alkyl chains to increase the solubility.

In certain embodiments of the present invention of corrosion inhibitors, The key innovative aspects of products include:
1. Macromolecular product design, which improves efficiency by forming more effective molecular barrier films on metal surfaces. These barriers are responsible for inhibiting corrosion, thereby, maintaining superior performance with intelligent molecular design.
2. Free from all inorganic species. No species such as Zn, Pb, Sn, P, Cr, Si, B, S, As, etc.
3. Environmentally friendly. Low aquatic toxicity, better biodegradability, and low/no bioaccumulation.
4. Produced with bio-based, renewable raw materials to the maximum extent possible (~85.0%)

In certain embodiments of the present invention of corrosion inhibitors is preferred due to multifunctional characteristics to protect against rust corrosion, copper, aluminum and alloy corrosion and also water separability from oil (as a demulsifier). In general three independent additives each one proving desired rust inhibition, copper protection, and demulsifiers are used in the formulation. The present invention provides all three protections by a single compound. This significantly reduces the number of additives required in the lubricant formulation at least from three additives to one single additive providing rust inhibition, copper protection against corrosion and performs as a demulsifier to separate water from oil. It is economically attractive by reducing three additives to one for the lubricant formulation.

In certain embodiments of the present invention are the most suitable for environmentally acceptable lubricants because of their low aqua toxicity to fish, *daphnia*, and algae.

In certain embodiments of the present invention of corrosion inhibitors is preferred in aftermarket automotive lubricant products.

In certain embodiments of the present invention of corrosion inhibitors have excellent solubility in bio-oils, bio-based oils, synthetic oils, petroleum based oils.

In yet other embodiments of the present invention, the corrosion inhibitors of the present invention are usually added to lubricant and fuel oils along with other additional lubricant additives including but not limited to antioxidants, anti-foaming, a viscosity modifier, pour point depressants, and other phenolic and aminic antioxidants.

In one embodiment, the present invention is a composition comprising present invention corrosion inhibitors, and at least one additive selected from the group consisting of i) a surface additive; ii) a performance enhancing additive, and iii) a lubricant protective additive.

In another embodiments the present invention is a lubricant composition comprising: a lubricant or a mixture of lubricants, a present invention corrosion inhibitor and at least one additive selected from the group consisting of i) a surface additive; ii) a performance enhancing additive, and iii) a lubricant protective additive.

In yet another embodiment the present invention is a method of improving a composition comprising combining the composition with present invention corrosion inhibitor, and at least one additive selected from the group consisting of i) a surface additive; ii) a performance enhancing additive, and iii) a lubricant protective additive.

In yet another embodiment the present invention is a method of improving a lubricant or a mixture of lubricants comprising combining the lubricant or mixture of lubricants with present invention corrosion inhibitor, and at least one additive selected from the group consisting of i) a surface additive; ii) a performance enhancing additive; and iii) a lubricant protective additive.

The compositions and methods of the present invention generally provide increased shelf life, increased oxidative resistance, enhanced performance and/or improved quality to materials, such as, for example, lubricants and lubricant oils and fuels. Other examples include biolubricants and biolubricant oils and biofuel such as biodiesel. In general, it is believed that because of the synergy of the corrosion inhibitors with the additives, the compositions described herein have superior corrosion resistance. The additives exhibit several key functions such as corrosion inhibition, detergency, viscosity modification, and antiwear performance, dispersant properties, cleaning and suspending ability. The disclosed compositions, in general, provide superior performance of lubricants in high temperatures applications due to the presence of high performance additives which are thermally stable at high temperatures with enhanced oxidation resistance.

In yet another embodiment the present invention of corrosion inhibitors is suitable for other corrodible materials including but not limited to fuels, biofuel, diesel, biodiesel, aviation fuels, kerosene, etc.

In certain embodiments, the present invention of corrosion inhibitors is suitable for additive packages for lubricants and fuels. These packages are for aftermarket products to enhance the performance of lubricants and fuel. Other additive packages designed for formulating lubricants and fuel by adding to base stock oils; petroleum based (Group I-V oils), bio-based, bio-oils, and gasoline, diesel, and biodiesel.

In one embodiment, the present invention is an additive package composition comprising present invention corrosion inhibitors, and at least one additive selected from the group consisting of i) a surface additive; ii) a performance enhancing additive, and iii) a lubricant protective additive.

In another embodiments the present invention is an additive package composition comprising: a lubricant or a mixture of lubricants, a present invention corrosion inhibitor and at least one additive selected from the group consisting of i) a surface additive; ii) a performance enhancing additive, and iii) a lubricant protective additive.

In yet another embodiment the present invention is a method of improving an additive package composition comprising combining the composition with present invention corrosion inhibitor; and at least one additive selected from the group consisting of i) a surface additive; ii) a performance enhancing additive, and iii) a lubricant protective additive.

In yet another embodiment the present invention is a method of improving an additive package composition comprising combining the composition with present invention corrosion inhibitor comprising additives one or more of an antioxidant, a metal deactivator, rust inhibitor, copper corrosion inhibitor, viscosity index modifier, pour point depressant, dispersing agent, detergent, an extreme-pressure, a dye, seal swell agents, a demulsifiers, and an anti-foaming additive; each additive present in the range 0.005%-5% and a carrier oil. A suitable carrier from petroleum, biobased, bio-oil is the one that dissolves all additives and easy to pour into a lubricant or a fuel. The ratio between additives and carrier oil may range from 1:99 to 99:1 by weight %, 5:95 by weight %, 10:90 by weight %, 20:90 by weight %, 30:70 by weight %, 40:60 by weight %, 50:50 by weight %, 60:40 by weight %, 70:30 by weight %, 80:20 by weight %, 90:10 by weight %, 95:5 by weight %.

In yet another embodiment the present invention of corrosion inhibitors may typically apply to coatings and paints including multi-package systems which are usually mixed prior to use, the pigments, catalysts and other additives can be added.

In yet another embodiment the present invention applications include base coat and clear coat formulations especially in the automotive, aviation, and marine industry.

Stabilized Lubricant Oil Compositions

Lubricants, lubricant oils, mixtures thereof and compositions comprising lubricants and lubricant oils can be improved by the methods of the present invention, by contacting the lubricant, lubricant oil, mixtures thereof or composition comprising the lubricant or lubricant oil or mixtures thereof with corrosion inhibitors, additives and mixtures thereof as described herein.

As used here, the terms "lubricants" and "lubricant oils" can be used interchangeably. Examples of lubricants suitable for use in the compositions and methods of the present invention include, but are not limited to: i) petroleum based oils (Group I, II and III), ii) synthetic oils (Group IV and V)) and iii) biolubricant oils (vegetable oils such as canola, soybean, corn oil etc.), and bio-based oils like polyol esters, biobased esters like estolides, bio-poly alpha olefins, bio alkylene glycols, bio poly alkylene glycols. Group I oils, as defined herein are solvent refined base oils. Group II oils, as defined herein are modern conventional base oils made by hydrocracking and early wax isomerization, or hydroisomerization technologies and have significantly lower levels of impurities than Group I oils. Group III oils, as defined herein are unconventional base oils. Groups I-III differ in impurities, and viscosity index as is shown in Kramer et al. "The Evolution of Base Oil Technology" *Turbine Lubrication in the 21st Century* ASTM STP #1407 W. R. Herguth and T. M. Wayne, Eds., American Society for Testing and Materials, West Conshohocken, Pa., 2001 the entire contents of which are incorporated herein by reference. Group IV oils as defined herein are "synthetic" lubricant oils, including, for example, poly-alpha olefins (PAOs). Biolubricants, as defined herein, are lubricants which contain at least 51% biomaterial (see Scott Fields, Environmental Health Perspectives, volume 111, number 12, September 2003, the entire contents of which are incorporated herein by reference). Other examples of lubricant oils can be found in Melvyn F. Askew "Biolubricants-Market Data Sheet" IENICA, August 2004 (as part of the IENICA work stream of the IENICA-INFORRM project); Taylor et al. "Engine lubricant Trends Since 1990" paper accepted for publication in the Proceedings I. Mech. E. Part J, Journal of Engineering Tribology, 2005 (Vol. 219 p 1-16); and Desplanches et al. "Formulating Tomorrow's Lubricants" page 49-52 of The Paths to Sustainable Development, part of special report published in October 2003 by Total; the entire contents of each of which are incorporated herein by reference. Biolubricants are often but not necessarily, based on vegetable oils. Vegetable derived, for example, from rapeseed, sunflower, palm, and coconut can be used as biolubricants. They can also be synthetic esters which may be partly derived from renewable resources. They can be made from a wider variety of natural sources including solid fats and low grade or waste materials such as tallows. Biolubricants in general offer rapid biodegradability and low environmental toxicity.

Additives

Examples of first additives suitable for use in the compositions and methods of the present invention include but are not limited to, surface additives, performance enhancing additives and lubricant protective additives.

Surface additives: In certain embodiments of the present invention, surface additives can protect the surfaces that are lubricated from wear, corrosion, rust, and frictions. Examples of these surface additives suitable for use in the compositions and methods of the present invention include, but are not limited to: (a) rust inhibitors, (b) corrosion inhibitors, (c) extreme pressure agents, (d) tackiness agents, (e) antiwear agents, (f) detergents and dispersants, (g) compounded oil (like fat or vegetable oil to reduce the coefficient of friction without affecting the viscosity), (h) antimisting, (i) seal swelling agents and (j) biocides.

Performance Enhancing Additives: In certain embodiments of the present invention, performance enhancing additives improve the performance of lubricants. Examples of these performance enhancing additives suitable for use in the Compositions and methods of the present invention include, but are not limited to: (a) pour-point depressants, (b) viscosity index modifiers (c) emulsifiers, and (d) demulsifiers.

Lubricant Protective Additives: In certain embodiments of the present invention, lubricant protective additives maintain the quality of oil from oxidation and other thermal degradation processes. Examples of these lubricant protective additives suitable for use in the compositions and methods of the present invention include, but are not limited to: (a) oxidation inhibitors and (b) foam inhibitors.

Other Lubricant Additives

In certain embodiments, a second additive can be used in the compositions and methods of the present invention in combination with the first antioxidant and the first additive as described above. Examples of second additives suitable for use in the compositions and methods of the present invention include, include but are not limited to, for example, dispersants, detergents, corrosion inhibitors, rust inhibitors, metal deactivators, antiwear and extreme pressure agents, antifoam agents, friction modifiers, seal swell agents, demulsifiers, viscosity index improvers, pour point depressants, and the like. See, for example, U.S. Pat. No. 5,498,809 for a description of useful lubricating oil composition additives, the disclosure of which is incorporated herein by reference in its entirety.

Dispersants: Examples of dispersants suitable for use in the compositions and methods of the present invention include, but are not limited to polybutenylsuccinic acid-amides, -imides, or -esters, polybutenylphosphonic acid derivatives, Mannich Base ashless dispersants, and the like.

Detergents: Examples of detergents suitable for use in the compositions and methods of the present invention include, but are not limited to metallic phenolates, metallic sulfonates, metallic salicylates, metallic phosphonates, metallic thiophosphonates, metallic thiopyrophosphonates, and the like.

Corrosion Inhibitors: Examples of corrosion inhibitors suitable for use in the compositions and methods of the present invention include, but are not limited to: phosphosulfurized hydrocarbons and their reaction products with an alkaline earth metal oxide or hydroxide, hydrocarbyl-thio-substituted derivatives of 1,3,4-thiadiazole, thiadiazole polysulphides and their derivatives and polymers thereof, thio and polythio sulphenamides of thiadiazoles such as those described in U.K. Patent Specification 1,560,830, and the like.

Rust Inhibitors: Examples of rust inhibitors suitable for use in the compositions and methods of the present invention include, but are not limited to: nonionic surfactants such as polyoxyalkylene polyols and esters thereof, anionic surfactants such as salts of alkyl sulfonic acids, and other compounds such as alkoxylated fatty amines, amides, alcohols and the like, including alkoxylated fatty acid derivatives treated with C9 to C16 alkyl-substituted phenols (such as the mono- and di-heptyl, octyl, nonyl, decyl, undecyl, dodecyl and tridecyl phenols).

Metal Deactivators: Metal deactivators as used herein, are the additives which form an inactive film on metal surfaces by complexing with metallic ions and reducing, for example, the catalytic effect on metal gum formation and other oxidation. Examples of metal deactivators suitable for use in the compositions and methods of the present invention include, but are not limited to N,N-disubstituted aminomethyl-1,2,4-triazoles, N,N-disubstituted aminomethyl-benzotriazoles, mixtures thereof, and the like.

Antiwear and Extreme Pressure Additives: Antiwear and extreme pressure additives, as used herein, react with metal surfaces to form a layer with lower shear strength then metal, thereby preventing metal to metal contact and reducing friction and wear. Examples of antiwear additives suitable for use in the compositions and methods of the present invention include, but are not limited to: sulfurized olefins, sulfurized esters, sulfurized animal and vegetable oils, phosphate esters, organophosphites, dialkyl alkylphosphonates, acid phosphates, zinc dialkyldithiophosphates, zinc diaryldithiophosphates, organic dithiophosphates, organic phosphorothiolates, organic thiophosphates, organic dithiocarbamates, dimercaptothiadiazole derivatives, mercaptobenzothiazole derivatives, amine phosphates, amine thiophosphates, amine dithiophosphates, organic borates, chlorinated paraffins, and the like.

Antifoam Agents: Examples of antifoam agents suitable for use in the compositions and methods of the present invention include, but are not limited to: polysiloxanes and the like.

Friction Modifiers: Examples of friction modifiers suitable for use in the compositions and methods of the present invention include, but are not limited to: fatty acid esters and amides, organic molybdenum compounds, molybdenum dialkylthiocarbamates, molybdenum dialkyl dithiophosphates, molybdenum dithiolates, copper oleate, copper salicylate, copper dialkyldithiophosphates, molybdenum disulfide, graphite, polytetrafluoroethylene, and the like.

Seal Swell Agents: Seal swell agents, as used herein, react chemically with elastomers to cause slight swell thus improving low temperature performance especially in, for example, aircraft hydraulic oil. Examples of seal swell agents suitable for use in the compositions and methods of the present invention include, but are not limited to: dioctyl sebacate, dioctyl adipate, dialkyl phthalates, and the like.

Demulsifiers: Demulsifiers, as used herein promote separation of oil and water in lubricants exposed to water. Examples of demulsifiers suitable for use in the compositions and methods of the present invention include, but are not limited to: the esters described in U.S. Pat. Nos. 3,098,827 and 2,674,619 incorporated herein by reference.

Viscosity Index Improvers: Examples of viscosity index improvers suitable for use in the compositions and methods of the present invention include, but are not limited to olefin copolymers, dispersant olefin copolymers, polymethacrylates, vinylpyrrolidone/methacrylate-copolymers, polyvinylpyrrolidones, polybutanes, styrene/-acrylate-copolymers, polyethers, and the like.

Pour Point Depressants: Pour point depressants as used herein reduce the size and cohesiveness of crystal structure resulting in low pour point and increased flow at low-temperatures. Examples of pour point depressants suitable for use in the compositions and methods of the present invention include, but are not limited to: polymethacrylates, alkylated naphthalene derivatives, and the like.

Other Antioxidants and Stabilizers

In certain embodiments, a second antioxidant or a stabilizer can be used in the compositions and methods of the present invention in combination with the first antioxidant and the first additive and optionally the second additive as described above. Examples of second antioxidants suitable for use in the compositions and methods of the present invention include, include but are not limited to:

1. Amine Antioxidants
1.1. Alkylated Diphenylamines, for example octylated diphenylamine; styrenated diphenylamine; mixtures of mono- and dialkylated tert-butyl-tert-octyldiphenylamines; and 4,4'-dicumyldiphenylamine.
1.2. Phenyl Naphthylamines, for example N-phenyl-1-naphthylamine; N-phenyl-2-naphthylamine; tert-octylated N-phenyl-1-naphthylamine.
1.3. Derivatives of para-Phenylenediamine, for example N,N'-diisopropyl-p-phenylenediamine; N,N'-di-sec-butyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N,N'-diphenyl-p-phenylenediamine; N,N'-di-(naphthyl-2)-p-phenylenediamine; N-isopropyl-N'-phenyl-p-phenylenediamine; N-(1,3-dimethylbutyl)-N'-phenyl-p-phenylenediamine; N-(1-methylheptyl)-N'-phenyl-p-phenylenediamine; N-cyclohexyl-N'-phenyl-p-phenylenediamine; N,N'-dimethyl-N,N'-di-sec-butyl-p-phenylenediamine.
1.4. Phenothiazines, for example phenothiazine; 2-methylphenothiazine; 3-octylphenothiazine; 2,8-dimethylphenothiazine; 3,7-dimethylphenothiazine; 3,7-diethylphenothiazine; 3,7-dibutylphenothiazine; 3,7-dioctylphenothiazine; 2,8-dioctylphenothiazine.
1.5. Dihydroquinolines, for example 2,2,4-trimethyl-1,2-dihydroquinoline or a polymer thereof.

2. Phenolic Antioxidants
2.1. Alkylated monophenols, for example 2,6-di-tert-butyl-4-methylphenol; 2,6-di-tert-butylphenol; 2-tert-butyl-4,6-dimethylphenol; 2,6-di-tert-butyl-4-ethylphenol; 2,6-di-tert-butyl-4-n-butylphenol; 2,6-di-tert-butyl-4-isobutylphenol; 2,6-di-tert-butyl-4-sec-butylphenol; 2,6-di-tert-butyl-4-octadecylphenol; 2,6-di-tert-butyl-4-nonylphenol; 2,6-dicyclopentyl-4-methylphenol; 2-(β-methylcyclohexyl)-4,6-dimethylphenol; 2,6-dioctadecyl-4-methylphenol; 2,4,6-tricyclohexylphenol; 2,6-di-tert-butyl-4-methoxymethylphenol; 2,6-di-tert-butyl-4-dimethylaminomethylphenol; o-tert-butylphenol.
2.2. Alkylated hydroquinones, for example 2,6-di-tert-butyl-4-methoxyphenol; 2,5-di-tert-butylhydroquinone; 2,5-di-tert-amylhydroquinone; 2,6-di-phenyl-4-octadecyloxyphenol.
2.3. Hydroxylated thiodiphenyl ethers, for example 2,2'-thiobis(6-tert-butyl-4-methyl-phenol); 2,2'-thiobis(4-octylphenol); 4,4'-thiobis(6-tert-butyl-3-methylphenol); 4,4'-thiobis(6-tert-butyl-2-methylphenol).
2.4. Alkylidenebisphenols, for example 2,2'-methylenebis(6-tert-butyl-4-methylphenol); 2,2'-methylenebis(6-tert-butyl-4-ethylphenol); 2,2'-methylenebis(4-methyl-6-(α-methylcyclohexyl)phenol); 2,2'-methylenebis(4-methyl-6-cyclohexylphenol); 2,2'-methylenebis(6-nonyl-4-methylphenol); 2,2'-methylenebis(4,6-di-tert-butylphenol); 2,2'-ethylidenebis(6-tert-butyl-4-isobutylphenol); 2,2'-methylenebis[6-□-methylbenzyl)-4-nonylphenol]; 2,2'-methylenebis[6-(α,α-dimethylbenzyl)-4-nonylphenol]; 4,4'-methylenebis(2,6-di-tert-butylphenol); 4,4'-methylenebis(6-tert-butyl-2-methylphenol); 1,1-bis(5-tert-butyl-4-hydroxy-2-methylphenyl)butane; 2,6-di(3-tert-butyl-5-methyl-2-hydroxybenzyl)-4-methylphenol; 1,1,3-tris(5-tert-butyl-4-hydroxy-2-methylphenyl)-3-n-dodecylmercaptobutane; ethylene glycol bis[3,3-bis(3'-tert-butyl-4'-hydroxyphenyl)butyrate]; di(3-tert-butyl-4-hydroxy-5-methylphenyl)dicyclopentadiene; di[2-(3'-tert-butyl-2'-hydroxy-5'-methylbenzyl)-6-tert-butyl-4-methylphenyl]terephthalate.
2.5. Benzyl compounds, for example 1,3,5-tris(3,5-di-tert-butyl-4-hydroxybenzyl)-2,4,6-trimethylbenzene; di(3,5-di-tert-butyl-4-hydroxybenzyl)sulfide; 3,5-di-tert-butyl-4-hydroxybenzylmercaptoacetic acid isooctyl ester; bis(4-tert-butyl-3-hydroxy-2,6-dimethyl-benzyl)dithioterephthalate; 1,3,5-tris(3,5-di-tert-butyl-4-hydroxybenzyl)isocyanurate; 1,3,5-tris(4-tert-butyl-3-hydroxy-2,6-dimethylbenzyl)isocyanurate; 3,5-di-tert-butyl-4-hydroxybenzylphosphonic acid dioctadecyl ester; 3,5-di-tert-butyl-4-hydroxybenzylphosphonic acid mono-ethyl ester calcium salt.
2.6. Acylaminophenols, for example 4-hydroxylauric acid anilide; 4-hydroxystearic acid anilide; 2,4-bis-octylmercapto-6-(3,5-di-tert-butyl-4-hydroxyaniline)-s-triazine; N-(3,5-di-tert-butyl-4-hydroxyphenyl)carbamic acid octyl ester.
2.7. Esters of β-(3,5-di-tert-butyl-4-hydroxyphenyl)propionic acid with mono- or polyhydric alcohols, e.g. with methanol; octadecanol; 1,6-hexanediol; neopentyl glycol; thiodiethylene glycol; diethylene glycol; triethylene glycol; pentaerythritol; tris(hydroxyethyl)isocyanurate; and di(hydroxyethyl)oxalic acid diamide.
2.8. Esters of β-(5-tert-butyl-4-hydroxy-3-methylphenyl)propionic acid with mono- or polyhydric alcohols, e.g. with methanol; octadecanol; 1,6-hexanediol; neopentyl glycol; thiodiethylene glycol; diethylene glycol; triethylene glycol; pentaerythritol; tris(hydroxyethyl)isocyanurate; and di(hydroxyethyl)oxalic acid diamide.

2.9. Amides of β-(3,5-di-tert-butyl-4-hydroxyphenyl)propionic acid, e.g., N,N'-di(3,5-di-tert-butyl-4-hydroxyphenyl-propionyl)hexamethylenediamine; N,N'-di(3,5-di-tert-butyl-4-hydroxyphenylpropionyl) trimethylenediamine; N,N'-di-(3,5-di-tert-butyl-4-hydroxyphenylpropionyl)hydrazine.
3. Sulfurized organic compounds, for example aromatic, alkyl, or alkenyl sulfides and polysulfines; sulfurized olefins; sulfurized fatty acid esters; sulfurized ester olefins; sulfurized oils; esters of β-thiodipropionic acid; sulfurized Diels-Alder adducts; sulfurized terpene compounds; and mixtures thereof.
4. Organo-borate compounds, for example alkyl- and aryl- (and mixed alkyl, aryl) substituted borates.
5. Phosphite and phosphate antioxidants, for example alkyl- and aryl- (and mixed alkyl, aryl) substituted phosphites, and alkyl- and aryl- (and mixed alkyl, aryl) substituted dithiophosphates such as O,O,S-trialkyl dithiophosphates, O,O,S-triaryldithiophosphates and dithiophosphates having mixed substitution by alkyl and aryl groups, phosphorothionyl sulfide, phosphorus-containing silane, polyphenylene sulfide, amine salts of phosphinic acid and quinone phosphates.
6. Copper compounds, for example copper dihydrocarbyl thio- or dithiophosphates, copper salts of synthetic or natural carboxylic acids, copper salts of alkenyl carboxylic acids or anhydrides such as succinic acids or anhydrides, copper dithiocarbamates, copper sulphonates, phenates, and acetylacetonates. The copper may be in cuprous (Cu) or cupric ($Cu^{II}$) form.
7. Zinc dithiodiphosphates, for example zinc dialkyldithiophosphates, diphenyldialkyldithiophosphates, and di(alkylphenyl)dithiophosphates.

In one embodiment, the compositions for use in the methods of the present invention, include but are not limited to:
a. a first corrosion inhibitor (in the concentration range, from about 0.0001% to about 50%, from about 0.0005% to about 20%, from about 0.005% to about 10%, from about 0.05% to about 5% or from about 0.01% to about 1%) with a first additive selected from the group comprising an antioxidant, a surface additive, a performance enhancing additive and a lubricant performance additive, for example, in amounts of from about 0.0005% to about 50%, from about 0.0001% to about 20%, from about 0.005% to about 10%, from about 0.05% to about 5% or from about 0.01% to about 1% by weight, based on the weight of lubricant to be stabilized.
b. the first corrosion inhibitor and the first additive as described in a. and a second additive, for example, in concentrations of from about 0.0001% to about 50% by weight, about 0.0005% to about 20% by weight, about 0.001% to about 10% by weight, from about 0.01% to about 5% by weight, from about 0.05% to about 1% by weight from about 0.1% to about 1% by weight based on the overall weight of the lubricant to be stabilized.
c. the first corrosion inhibitor and the first additive as described in a. and optionally the second additive as described in b. and a second corrosion inhibitor, for example, Irgacor® 190, Irgacor® NPA, Cuvan® 303, Cuvan® 484, Cuvan® 826, in the concentration range, from about 0.0001% to about 50%, from about 0.0005% to about 20%, from about 0.005% to about 10%, 1615 from about 0.05% to about 5% or from about 0.01% to about 1%) by weight, based on the weight of lubricant to be stabilized.

In yet another embodiment, the antioxidant compositions for use in the methods of the present invention include but is not limited to: the first antioxidant from the present invention and the second antioxidant from the section.
'Other Antioxidants and Stabilizers'.

The antioxidant composition, where in the weight ratio of the second antioxidant to the first antioxidant of the present invention is from about 1:99 to 99:1, from about 10:90, 20:80, 30:70, 40:60, 50:50, 60:40, 70:30, 80:20, 90:10. The second antioxidant second antioxidant, for example, Irganox® L 57, Irganox® L64, Irganox® 1330, Irganox® 1076, Irganox® 5057 and 1625 Irganox® L 135, Polnox®7030, Polnox® 7070, Polnox® 8020, Polnox®8060, Polnox®8080.

EXAMPLE 1

Octanoyl chloride (1 mL, 5.82 mmol) was added slowly to the mixture of 2-t-butyl-4-methoxyphenol (1 g, 5.82 mmol) and triethylamine (0.81 mL, 5.82 mmol) dissolved in THF in ice-bath under a nitrogen atmosphere. The reaction mixture was stirred overnight at room 1630 temperature under nitrogen atmosphere. The completion of the reaction was confirmed by TLC and FTIR. The mixture was filtered to remove salt and then washed with THF. It was then concentrated under reduced pressure. The crude product was dissolved in EtOAc and extracted with saturated $NaHCO_3$ and brine. The organic phase was dried over anhydrous $Na_2SO_4$. Concentration in vacuo gave the target compounds as a light yellow liquid.

EXAMPLE 2

The same method in Example 1 is used with a linear alkyl chain of $C_{12}$, $C_{16}$ and $C_{18}$ atoms and a branched alkyl chain with $C_8$ atoms.

EXAMPLE 3

The same method in Example 1 is used for the synthesis of phenol and substituted phenols such as 2-methoxyphenol, o-cresol, m-cresol, p-cresol and o,m,p-cresol mixtures, 2-sec-butylphenol, 2-tert-amylphenol, 2-tert-butylphenol, 2-isopropyl-5-methylphenol, eugenol, isoeugenol, 4-ethyl-2-methoxyphenol, 4-t-butylphenol, resorcinol, catechol, and phloroglucinol.

EXAMPLE 4

The same method in Example 1 is used with a linear alkyl chain of $C_{12}$, $C_{16}$ and $C_{18}$ atoms and a branched alkyl chain of $C_8$ atoms for phenol and substituted phenols in Example 3.

EXAMPLE 5

Oxalyl chloride (6 mL, 67.06 mmol) was added slowly to the mixture of o-cresol (5.74 g, 53.12 mmol) and stearic acid (15.11 g, 53.12 mmol) in dichloromethane (15 mL) with a catalytic amount (a couple of drops) of DMF in ice-bath under a nitrogen atmosphere. The reaction mixture was stirred for 30 min at this temperature under nitrogen atmosphere. Then, the reaction mixture was stirred at 60° C. for 6-10 h. The completion of the reaction was confirmed by TLC and FTIR. After cooling, the crude product was extracted with saturated $NaHCO_3$ and brine. The organic phase was dried over anhydrous $Na_2SO_4$. It was then concentrated under reduced pressure. Concentration in vacuo gave the target compound.

EXAMPLE 6

The same method in Example 5 is used with a linear alkyl chain of $C_{12}$, $C_{16}$ and $C_{18}$ atoms and a branched alkyl chain of $C_8$ atoms.

EXAMPLE 7

Example 5 is synthesized using thionyl chloride instead of oxalyl chloride.

EXAMPLE 8

The same method in Example is used with a linear alkyl chain of $C_{12}$, $C_{16}$ and $C_{18}$ atoms and a branched alkyl chain of $C_8$ atoms for phenol and substituted phenols such as 2-methoxyphenol, 2-t-butyl-4-methoxyphenol, m-cresol, p-cresol and o,m,p-cresol mixtures, 2-sec-butylphenol, 2-tert-amylphenol, 2-tert-butylphenol, 2-isopropyl-5-methylphenol, eugenol, isoeugenol, 4-ethyl-2-methoxyphenol, 4-t-butylphenol, resorcinol, catechol and phloroglucinol.

EXAMPLE 9

The same method in Example 7 is used with a linear alkyl chain of $C_{12}$, $C_{16}$ and $C_{18}$ atoms and a branched alkyl chain of $C_8$ atoms for phenol and substituted phenols such as 2-methoxyphenol, 2-t-butyl-4-methoxyphenol, m-cresol, p-cresol and o,m,p-cresol mixtures, 2-sec-butylphenol, 2-tert-amylphenol, 2-tert-butylphenol, 2-isopropyl-5-methylphenol, eugenol, isoeugenol, 4-ethyl-2-methoxyphenol, 4-t-butylphenol, resorcinol, catechol and phloroglucinol.

EXAMPLE 10

Concentrated $H_2SO_4$ (161.2 mL, 3 mol) was added slowly to a reaction mixture of 2-methoxyphenol (150 g, 1.21 mol) and formaldehyde (37% aq) (90.8 mL, 1.21 mol) in distilled 1675 water (600 mL) in ice-bath. Then, the reaction mixture was refluxed under $N_2$ for 6-10 h. The completion of the reaction was confirmed by TLC. After cooling down the reaction mixture, solution phase was decantated and the precipitate was washed with water. The precipitate dried under vacuum gave the target product as light yellow to brown powder. This reaction was done using other solvents such as toluene and 1,2-dichloroethane. This reaction was also done using oxalic acid as a catalyst.

EXAMPLE 11

The same method in Example 10 was used for the synthesis of o-cresol, o,m,p-cresol mixtures, 2-t-butyl-4-methoxyphenol, eugenol, isoeugenol, 4-ethyl-2-methoxyphenol, and 4-t-butylphenol. It is also used others such as m-cresol, p-cresol, 2-sec-butylphenol, 2-tert-amylphenol, 2-tert-butylphenol, 2-isopropyl-5-methylphenol, resorcinol, catechol, and phloroglucinol. This reaction was done using other solvents such as toluene and 1,2-dichloroethane. This reaction was done using oxalic acid as a catalyst.

EXAMPLE 12

Lauroyl chloride (152 mL, 0.639 mol) in 300 mL of THF was added slowly to the mixture of the product from Example 10 (100 g, 0.188 mol) and triethylamine (88.5 mL, 0.639 mol) dissolved in 600 mL of THF in ice-bath under a nitrogen atmosphere. The reaction mixture was stirred overnight at room temperature under nitrogen atmosphere. The completion of the reaction was confirmed by FTIR. The mixture was filtered to remove salt and then washed with THF. It was then concentrated under reduced pressure. The crude product was dissolved in EtOAc, extracted with saturated $NaHCO_3$ and brine. The organic phase was dried over anhydrous $Na_2SO_4$. Concentration in vacuo gave the target compounds as light yellow oil.

EXAMPLE 13

The same method in Example 12 was used with a linear alkyl chain of $C_8$, $C_{12}$, $C_{16}$ and a branched alkyl chain of $C_8$ atoms. It is also used with a linear alkyl chain of $C_{18}$ atoms.

EXAMPLE 14

The same method in Example 5 is used with a linear alkyl chain of $C_8$, $C_{12}$, $C_{16}$ and $C_{18}$ atoms and a branched alkyl chain of $C_8$ atoms for Example 13.

EXAMPLE 15

The same method in Example 5 is used with a linear alkyl chain of $C_8$, $C_{12}$, $C_{16}$ and $C_{18}$ atoms and a branched alkyl chain of $C_8$ atoms for Example 13.

EXAMPLE 16

The same method in Example 12 was used with a linear alkyl chain of $C_8$ for 4-t-butylphenol and 2-t-butyl-4-methoxyphenol used as starting material in Example 11. The same method in Example 5 is used with a linear alkyl chain of $C_8$, $C_{12}$, $C_{16}$ and $C_{18}$ atoms and a branched alkyl chain of $C_8$ atoms for the other compounds obtained in Example 11.

EXAMPLE 17

The same method in Example 5 is used with a linear alkyl group of $C_8$, $C_{12}$, $C_{16}$ and $C_{18}$ atoms and a branched alkyl chain of $C_8$ atoms for Example 11.

EXAMPLE 18

The same method in Example 7 is used with a linear alkyl chain of $C_8$, $C_{12}$, $C_{16}$ and $C_{18}$ atoms and a branched alkyl chain of $C_8$ atoms for Example 11.

EXAMPLE 19

Oxalyl chloride (3.7 mL, 42.56 mmol) was added slowly to the mixture of 2-methoxyphenol (4.49 g, 35.47 mmol) and oleic acid (10.02 g, 35.47 mmol) with a catalytic amount (a couple of drops) of DMF in ice-bath under a nitrogen atmosphere. The reaction mixture was stirred for 30 min at this temperature under nitrogen atmosphere. Then, the reaction mixture was stirred at 60° C. for 6-10 h. The completion of the reaction was confirmed by TLC and FTIR. After cooling, the crude product was extracted with saturated $NaHCO_3$ and brine. The organic phase was dried over anhydrous $Na_2SO_4$. It was then concentrated under reduced pressure. Concentration in vacuo gave the target compound yellow oil. This reaction was done using thionyl chloride.

EXAMPLE 20

The same method in Example 19 was used for phenol, o-cresol, resorcinol and catechol. It is also used others such as 2-t-butyl-4-methoxyphenol, m-cresol, p-cresol, o,m,p-cresol mixtures, 2-sec-butylphenol, 2-tert-amylphenol, 2-tert-butylphenol, 2-isopropyl-5-methylphenol, eugenol, isoeugenol, 4-ethyl-2-methoxyphenol and 4-t-butylphenol, and phloroglucinol. Dichloromethane was used as a solvent of substituted phenols which are solid at reaction temperature 60° C.

EXAMPLE 21

Example 19 was synthesized using thionyl chloride instead of oxalyl chloride.

EXAMPLE 22

Example 20 is synthesized using thionyl chloride instead of oxalyl chloride.

EXAMPLE 23

Oxalyl chloride (3.6 mL, 41.3 mmol) was added slowly to the mixture of the product in Example 10 (5 g, 9.39 mmol) and oleic acid (9 g, 31.9 mmol) in dichloromethane (25 mL) with a catalytic amount (0.1 mL) of DMF in ice-bath under a nitrogen atmosphere. The reaction mixture was stirred for 30 min at this temperature under nitrogen atmosphere. Then, the reaction mixture was stirred at 60° C. for 6-10 h. The completion of the reaction was confirmed FTIR. After cooling, the crude product was extracted with saturated $NaHCO_3$ and brine. The organic phase was dried over anhydrous $Na_2SO_4$. It was then concentrated under reduced pressure. Concentration in vacuo gave the target compound as yellow oil. This reaction was done using thionyl chloride. This reaction was also done as following: Thionyl chloride was added slowly to the mixture of an oleic acid with a catalytic amount of DMF in ice-bath by scrubbing gaseous products into aqueous sodium hydroxide solution. The reaction mixture was stirred at room temperature for 2-4 h. Excess thionyl chloride was distilled of. In a separate flask, the product of Example 10 was dissolved in 1,2-dichloroethane by followed by addition of triethylamine. Then, this mixture was added drop wise over a period of 30 min into oleoyl chloride in ice-bath under a nitrogen atmosphere. The reaction mixture was stirred at room temperature for 8-16 h. The completion of the reaction was confirmed FTIR. The salt formed in the reaction was filtered out and washed with the reaction solvent. The concentration of filtrate in rotavapor gave the target compound as yellow oil. This was done using other solvents such as ethyl acetate and toluene.

EXAMPLE 24

The compound in Example 23 was synthesized using thionyl chloride instead of oxalyl chloride.

EXAMPLE 25

The same method in Example 24 was used to attach oleic acid to the compounds obtained in Example 12 such as using o-cresol, o,m,p-cresol mixtures, resorcinol, and catechol. It is also used others such as using m-cresol, p-cresol, 2-sec-butylphenol, 2-tert-amylphenol, 2-tert-butylphenol, 2-isopropyl-5-methylphenol, 2-t-butyl-4-methoxyphenol, eugenol, isoeugenol, 4-ethyl-2-methoxyphenol and 4-t-butylphenol and phloroglucinol.

EXAMPLE 26

Example 25 is synthesized using thionyl chloride instead of oxalyl chloride.

EXAMPLE 27

Concentrated $H_2SO_4$ (1.9 mL, 0.036 mol) was added slowly to a reaction mixture of oleic acid (101 g, 0.36 mol) in MeOH (200 mL). Then, the mixture was refluxed for 2-4 h under nitrogen atmosphere. The completion of the reaction was confirmed by FTIR. After cooling down the reaction mixture, the crude product was concentrated in vacuo. It was then extracted with saturated $NaHCO_3$ and brine. The organic phase was dried over anhydrous $Na_2SO_4$. Concentration in vacuo gave the target product as light yellow oil.

EXAMPLE 28

The same method in Example 27 was used for the attachment of $C_4$ alkyl chain. It is also used for the attachment of $C_2$ and $C_3$ alkyl chains.

EXAMPLE 29

The mixture of oleic acid (7.51 g, 26.6 mmol), 1-octadecanol (7.19 g, 26.6 mmol), $PTSA.H_2O$ (0.51 g, 2.7 mmol) and molecular sieves were stirred at 110° C. for 4 h under a nitrogen atmosphere. The completion of the reaction was confirmed by FTIR. After cooling down the reaction mixture, molecular sieves were filtered and washed with EtOAc. The filtrate was then extracted with saturated $NaHCO_3$ and brine. The organic phase was dried over anhydrous $Na_2SO_4$. Concentration in vacuo gave the target product as a yellow wax.

EXAMPLE 30

The same method in Example 29 is used for the attachment of a linear alkyl chain of $C_8$, $C_{12}$ and $C_{16}$ atoms and a branched alkyl chain of $C_8$ atoms.

EXAMPLE 31

Example 30 is synthesized using apparatus Dean-Stark instead of molecular sieves.

EXAMPLE 32

The same method in Example 31 is used to make Example 30.

EXAMPLE 33

To a 50 ml two-neck round bottom flask equipped thermocouple-temperature controller was added methyl oleate obtained in Example 28 (25.22 g, 85.08 mmol) and maleic anhydride (8.34 g, 85.08 mmol) in dimethyl succinate (6 mL, 0.2 eq. by wt). The reaction mixture was stirred at 175° C. under a nitrogen atmosphere for 4-6 h. The completion of the reaction was confirmed by FTIR and TLC. The reaction product was used in next step without further purification.

EXAMPLE 34

The same method in Example 33 was used for the compounds obtained in Example 19.

EXAMPLE 35

The same method in Example 33 was used for the compounds obtained in Example 20 such as using phenol, o-cresol, resorcinol, and catechol. It is also used others such as 2-t-butyl-4-methoxyphenol, m-cresol, p-cresol, o,m,p-cresol mixtures, 2-sec-butylphenol, 2-tert-amylphenol, 2-tert-butylphenol, 2-isopropyl-5-methylphenol, eugenol, isoeugenol, 4-ethyl-2-methoxyphenol and 4-t-butylphenol, and phloroglucinol.

EXAMPLE 36

The same method in Example 33 was used for the compounds obtained in Example 23.

EXAMPLE 37

The same method in Example 33 was used for the compounds obtained in Example 25 such as using o-cresol, o,m,p-cresol mixtures, resorcinol, and catechol. It is also used others such as using m-cresol, p-cresol, 2-sec-butylphenol, 2-tert-amylphenol, 2-tert-butylphenol, 2-isopropyl-5-methylphenol, 2-t-butyl-4-methoxyphenol, eugenol, isoeugenol, 4-ethyl-2-methoxyphenol and 4-t-butylphenol and phloroglucinol.

EXAMPLE 38

The same method in Example 33 was used for the compound obtained in Example 28. It is also used for the attachment of $C_2$ and $C_3$ alkyl chains.

EXAMPLE 39

The same method in Example 33 was used for the compound obtained in Example 29.

EXAMPLE 40

The same method in Example 33 is used for the compounds obtained in Example 30.

EXAMPLE 41

Propylene oxide (4.45 mL, 63.76 mmol) was added slowly to a reaction mixture of phenol (5 g, 53.13 mmol) dissolved in aqueous NaOH (4.25 g, 106.2 mmol) in 15 mL water. Then, the temperature was raised to 75° C. for 16 h under nitrogen atmosphere. The completion of the reaction was confirmed by TLC and FTIR. After cooling down the reaction mixture, the crude product was acidified with 1M HCl. It was diluted with EtOAc and then extracted with saturated $NaHCO_3$, 1M NaOH (aq) and brine. The organic phase was dried over anhydrous $Na_2SO_4$. Concentration in vacuo gave the target product as a colorless liquid.

EXAMPLE 42

The same method in Example 41 is used for the substituted phenols such as 2-methoxyphenol, o-cresol, m-cresol, p-cresol and o,m,p-cresol mixtures, 2-sec-butylphenol, 2-tert-amylphenol, 2-tert-butylphenol, 2-isopropyl-5-methylphenol, eugenol, isoeugenol, 4-ethyl-2-methoxyphenol, 4-t-butylphenol, resorcinol, catechol and phloroglucinol.

EXAMPLE 43

The same method in Example 41 is used for the compound obtained in Example 10.

EXAMPLE 44

The same method in Example 41 is used for the compounds obtained in Example 11.

EXAMPLE 45

Octadecyl oleate succinic anhydride obtained in Example 36 (2.03 g, 2.57 mmol) was stirred with 1-octadecanol (0.69 g, 2.57 mmol) and dimethyl succinate (0.2 eq by weight) at 130° C. for 2-4 h under nitrogen atmosphere. The completion of the reaction was confirmed by FTIR. No work-up was required. The product appeared as yellow wax upon cooling.

EXAMPLE 46

The same method in Example 45 is used for the compound obtained in Example 33 with a linear alkyl alcohol of $C_8$, $C_{12}$ and $C_{16}$ atoms and a branched alkyl alcohol of $C_8$ atoms, ethylene glycol, hexanediol, neopentyl glycol, 2-methoxyphenol, o-cresol, m-cresol, p-cresol and o,m,p-cresol mixtures, diethanolamine, trimethylolpropane, glycerol, triethanolamine, pentaeryrthritol and di-pentaeryrthritol.

EXAMPLE 47

The same method in Example 45 is used for the compound obtained in Example 34 with the reaction of $C_1$-$C_{24}$ mono alkyl alcohols, ethylene glycol, 2-methoxyphenol, o-cresol, m-cresol, p-cresol and o,m,p-cresol mixtures, hexanediol, neopentyl glycol, diethanolamine, trimethylolpropane, glycerol, triethanolamine, pentaeryrthritol, and di-pentaeryrthritol.

EXAMPLE 48

The same method in Example 45 was used for the compound obtained in Example 35 with a linear alkyl alcohol of $C_8$, $C_{12}$ and $C_{16}$ atoms and a branched alkyl alcohol of $C_8$ atoms, 2-methoxyphenol, o-cresol, m-cresol, p-cresol and o,m,p-cresol mixtures, ethylene glycol, hexanediol, neopentyl glycol, diethanolamine, trimethylolpropane, glycerol, triethanolamine, pentaeryrthritol and di-pentaeryrthritol.

EXAMPLE 49

The same method in Example 45 was used for the compound obtained in Example 36 with a linear alkyl alcohol of $C_8$, $C_{12}$ and $C_{16}$ atoms and a branched alkyl alcohol of $C_8$ atoms.

EXAMPLE 50

The same method in Example 45 was used for the compound obtained in Example 37 with a linear alkyl alcohol of $C_8$, $C_{12}$ and $C_{16}$ atoms and a branched alkyl alcohol of $C_8$ atoms.

EXAMPLE 51

The same method in Example 45 was used for the compound obtained in Example 39 with a linear alkyl alcohol of $C_8$, $C_{12}$ and $C_{16}$ atoms and a branched alkyl alcohol of $C_8$ atoms, 2-methoxyphenol, o-cresol, m-cresol, p-cresol and o,m,p-cresol mixtures, ethylene glycol, hexanediol, neopentyl glycol, diethanolamine, trimethylolpropane, glycerol, triethanolamine, pentaeryrthritol and di-pentaeryrthritol.

EXAMPLE 52

The same method in Example 45 is used for the compound obtained in Example 40 with a linear alkyl alcohol of $C_8$, $C_{12}$ and $C_{16}$ atoms and a branched alkyl alcohol of $C_8$ atoms, 2-methoxyphenol, o-cresol, m-cresol, p-cresol and o,m,p-cresol mixtures, ethylene glycol, hexanediol, neopentyl glycol, diethanolamine, trimethylolpropane, glycerol, triethanolamine, pentaeryrthritol and di-pentaeryrthritol.

EXAMPLE 53

The same method in Example 45 is used the compound obtained in Example 10 to react with succinic anhydrides such as a DDSA, ODSA, OSA, and PIBSA.

EXAMPLE 54

The same method in Example 45 is used the compound obtained in Example 11 to react with succinic anhydrides such as DDSA, ODSA, OSA, and PIBSA.

EXAMPLE 55

The same method in Example 45 is used substituted phenols such as 2-methoxyphenol, o-cresol, m-cresol, p-cresol and o,m,p-cresol mixtures, 2-sec-butylphenol, 2-tert-amylphenol, 2-tert-butylphenol, 2-isopropyl-5-methylphenol, eugenol, isoeugenol, 4-ethyl-2-methoxyphenol, 4-t-butylphenol, resorcinol, catechol and phloroglucinol to react with succinic anhydrides such as a linear alkyl and a branched alkyl of octenyl succinic anhydride, tetradecenylsuccinic anhydride, hexadecenylsuccinic anhydride and polyisobutylene succinic anhydride.

EXAMPLE 56

The same method in Example 45 is used substituted phenols such as 2-methoxyphenol, o-cresol, m-cresol, p-cresol and o,m,p-cresol mixtures, 2-sec-butylphenol, 2-tert-amylphenol, 2-tert-butylphenol, 2-isopropyl-5-methylphenol, eugenol, isoeugenol, 4-ethyl-2-methoxyphenol, 4-t-butylphenol, resorcinol, catechol, and phloroglucinol to react with the compound obtained in Example 33.

EXAMPLE 57

The same method in Example 45 is used substituted phenols such as 2-methoxyphenol, o-cresol, m-cresol, p-cresol and o,m,p-cresol mixtures, 2-sec-butylphenol, 2-tert-amylphenol, 2-tert-butylphenol, 2-isopropyl-5-methylphenol, eugenol, isoeugenol, 4-ethyl-2-methoxyphenol, 4-t-butylphenol, resorcinol, catechol, and phloroglucinol to react with the compound obtained in Example 38.

EXAMPLE 58

The same method in Example 45 is used substituted phenols such as 2-methoxyphenol, o-cresol, m-cresol, p-cresol and o,m,p-cresol mixtures, 2-sec-butylphenol, 2-tert-amylphenol, 2-tert-butylphenol, 2-isopropyl-5-methylphenol, eugenol, isoeugenol, 4-ethyl-2-methoxyphenol, 4-t-butylphenol, resorcinol, catechol, and phloroglucinol to react with the compound obtained in Example 39.

EXAMPLE 59

The same method in Example 45 is used substituted phenols such as 2-methoxyphenol, o-cresol, m-cresol, p-cresol and o,m,p-cresol mixtures, 2-sec-butylphenol, 2-tert-amylphenol, 2-tert-butylphenol, 2-isopropyl-5-methylphenol, eugenol, isoeugenol, 4-ethyl-2-methoxyphenol, 4-t-butylphenol, resorcinol, catechol, and phloroglucinol to react with the compound obtained in Example 40.

EXAMPLE 60

The same method in Example 45 was used the compound obtained in Example 41 to react with an octadecenylsuccinic anhydride.

EXAMPLE 61

The same method in Example 45 is used the compound obtained in Example 41 to react with other succinic anhydrides such as DDSA, ODSA, OSA, and PIBSA.

EXAMPLE 62

The same method in Example 45 is used the compound obtained in Example 41 to react with the compounds obtained in Example 33.

EXAMPLE 63

The same method in Example 45 is used the compound obtained in Example 41 to react with the compounds obtained in Example 34.

EXAMPLE 64

The same method in Example 45 is used the compound obtained in Example 41 to react with the compounds obtained in Example 35.

EXAMPLE 65

The same method in Example 45 is used the compound obtained in Example 41 to react with the compounds obtained in Example 36.

EXAMPLE 66

The same method in Example 45 is used the compound obtained in Example 41 to react with the compounds obtained in Example 37.

EXAMPLE 67

The same method in Example 45 is used the compound obtained in Example 41 to react with the compounds obtained in Example 38.

EXAMPLE 64

The same method in Example 45 is used the compound obtained in Example 41 to react with the compounds obtained in Example 39.

EXAMPLE 68

The same method in Example 45 is used the compound obtained in Example 41 to react with the compounds obtained in Example 40.

The performance of corrosion inhibitor can be evaluated using ASTM D130 and ASTM D665 test methods for fluids like lubricants and fuels. ASTM D130 test method is suited to test the performance corrosion inhibitors for copper metals whereas ASTM D665 is of steel materials. The Copper Strip Tarnish Test assesses the relative degree of corrosivity of petroleum products, including aviation fuels, automotive gasoline, natural gasoline, solvents, kerosene, diesel fuel, distillate fuel oil, lubricating oil and other products. A polished copper strip is immersed in 30 mL of the sample at elevated temperature. After the test period, the strip is examined for evidence of corrosion and a classification number from 1-4 is assigned based on a comparison with the ASTM Copper Strip Corrosion Standards. The most typical test run is for 3 hours @100° C. However, time and temperature can vary according to product type and specification. Results are reported as a number followed by a letter according to the ASTM chart, a rating of 1a and 1b being an excellent corrosion inhibitor and a rating of 4 is a poor performer.

The efficacy of the corrosion inhibitor of representative samples of the present invention was tested by adding 500 ppm in canola oil, Group II oil and polyolester (synthetic oil, Group IV). The results are summarized in Table 1.

| Corrosion Inhibitor | CORROSION INHIBITION (ASTM D130) | | | | RUST INHIBITION (ASTM D665-2) | | | | DEMULSIFICATION (ASTM D1401-42) | |
|---|---|---|---|---|---|---|---|---|---|---|
| | Treat Level | Canola Oil | Group II Oil | Polyol Ester | Treat Level | Canola Oil | Treat Level | Group II Oil | Canola Oil | Group II Oil |
| Example 49 | 0.05% | 1A | 1B | 1A | 0.5% | Pass | 0.05% | Pass | 40-40-0 (30) | 40-40-0 (30) |

In a similar way, corrosion inhibitors of this invention were also tested using ASTM D665 protocol. In this method, 300 ml of fluid treated with corrosion inhibitor and 30 ml of standard synthetic sea water are mixed thoroughly at 60° C. and a standard polished, cylindrical steel rod are immersed in the fluid for 4 hours. The rod will be examined for a pass or fail the test. If there is no sign of rust on the surface of the steel rod, a rating of Pass is given to the product. The products of this invention show no rust corrosion for steel rods in canola oil if they are treated with 0.4-0.5 weight % of the oil.

The ASTM D 1401 test method was used to study water separability of the present invention. In this method is a known amount of water and oil treated with the demulsifier, 40 ml were poured in to a graduated jar of a specified diameter. The sample was kept at a constant temperature (40° C.). Both oil and water were stirred using a motorized stirrer at a specified specific rotation speed of 1500 rpm. The time taken for the two separate was measured in minutes, the faster the separation better is the demulsibility. The results are quoted as ml-ml-emulsion (time, min). For example, 40-40-0 (30) means it took 30 minutes to separate the two with no emulsion. The sample of the present invention treated at the same level for corrosion inhibitor. For example, canola was treated at 0.5% with the sample of the present invention whereas Group II oil was tested at 0.05%.

While this invention has been particularly shown and described with references to preferred embodiments thereof, it will be understood by those skilled in the art that various changes in form and details may be made therein without departing from the scope of the invention encompassed by the appended claims.

What is claimed is:
1. A compound having Structural Formula I:

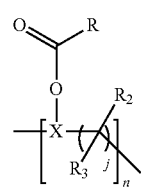

Structural Formula I wherein:
X is:

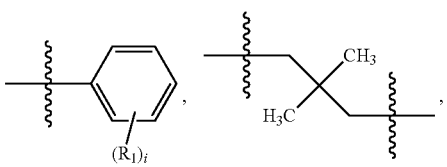

-continued

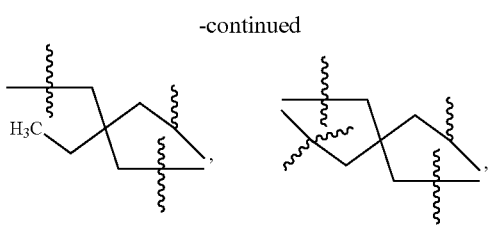

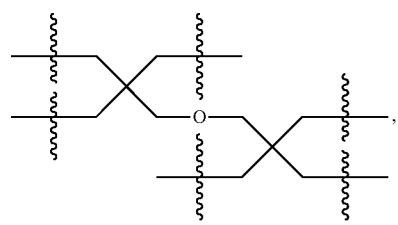

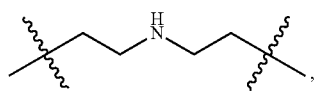

-continued

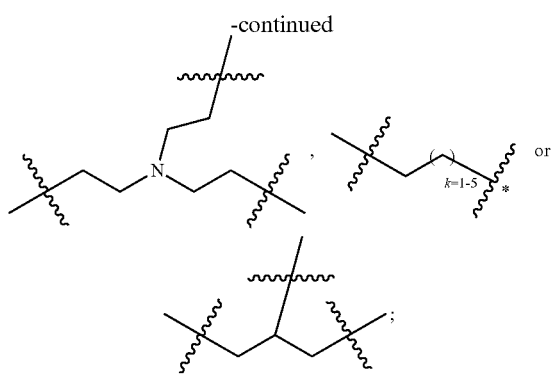

each $R_1$ is H, independently an optionally substituted $C_1$-$C_{20}$ alkyl group, an optionally substituted $C_1$-$C_{10}$ alkyl group, a tertiary carbon group, a methyl group, a methoxy group, an optionally substituted aryl group, an optionally substituted alkoxy group, an optionally substituted carbonyl group, an optionally substituted alkoxycarbonyl group, an optionally-CH(R''')(R'''COOH) wherein each R''' independently $C_1$-$C_{10}$ linear or branched alkyl chain, or an optionally substituted carbocyclic or heterocyclic non-aromatic ring;

i=0, 1, 2, 3;
j=0 or 1;
n is an integer from 1 to 1000;
and wherein,
when n=1, then j=0; and
when n>1 then j=1;

each $R_2$ and $R_3$ is independently H, a $C_1$-$C_8$ linear or branched or cyclic alkyl chain, an optionally substituted $C_1$-$C_{20}$ alkyl group, an optionally substituted $C_1$-$C_{10}$ alkyl group, a tertiary carbon group, a methyl group, a methoxy group, an optionally substituted aryl group, and optionally substituted alkoxy group, an optionally substituted carbonyl group, an optionally substituted alkoxycarbonyl group, or —CH(R''')(R'''COOH);

R is an alkenyl chain represented by (1)

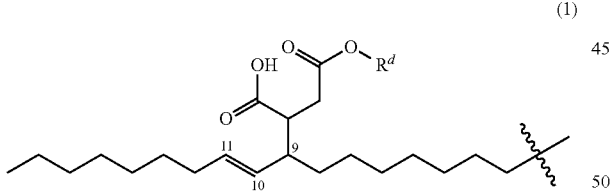

(2)

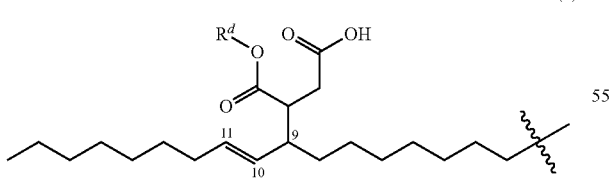

(3)

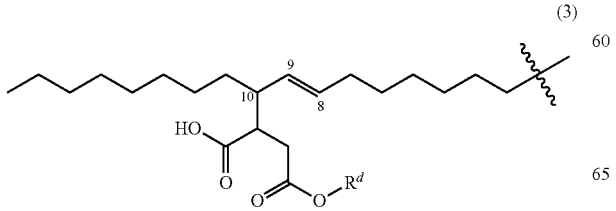

-continued (4)

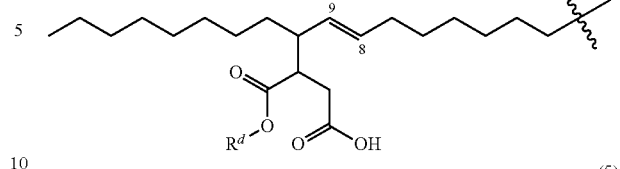

(5)

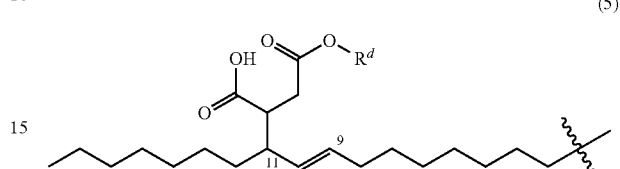

(6)

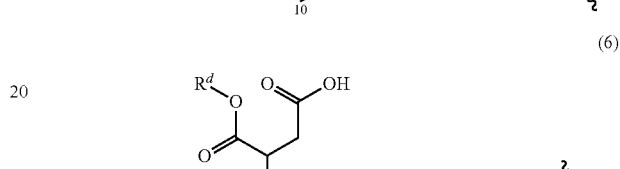

(7)

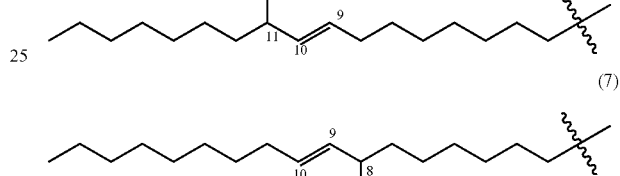

or (8)

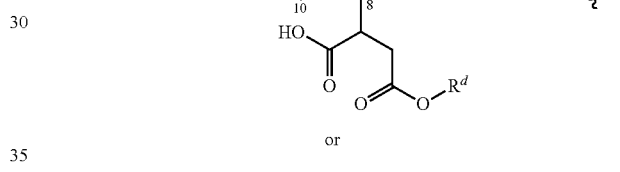

and each $R^d$ is a linear or branched $C_1$-$C_{24}$ alkyl chain.

2. The compound of claim 1, wherein:
n=1;
j=0; and
R is a structure of

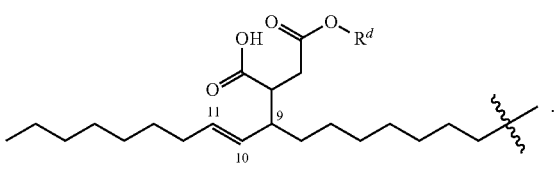

3. The compound of claim 1, wherein:

[X] is

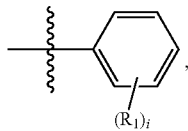

and the compound is represented by structural Formula II:

Structural Formula II

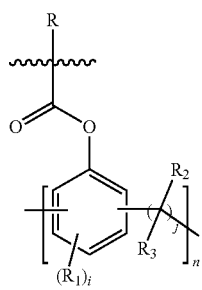

wherein:

each $R_2$, $R_3$ independently is H, methyl, or a $C_1$-$C_8$ linear or branched or cyclic alkyl chain.

4. The compound of claim 3, wherein each $R_2$, $R_3$ is H and j=1, wherein the compound structure is represented by Structural Formula III:

Structural Formula III

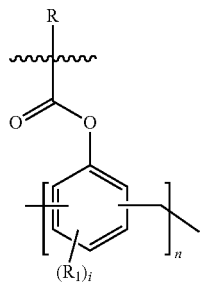

wherein, $R_1$ is selected from the group consisting of

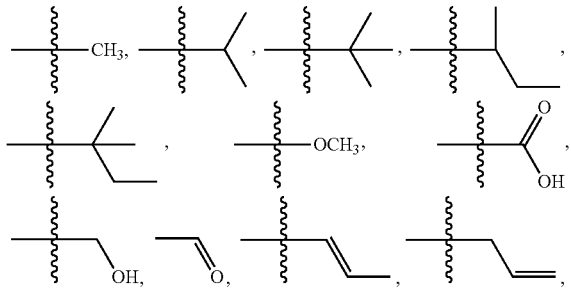

-continued

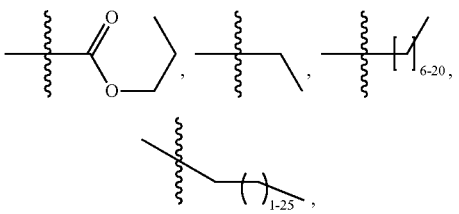

alkyl acid chain as shown below

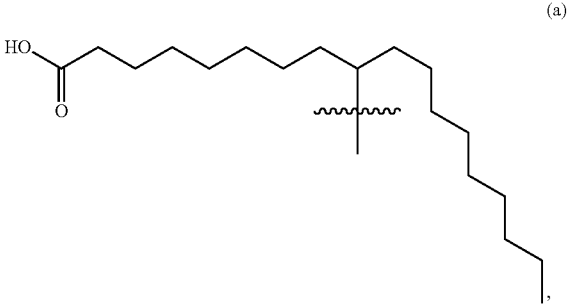

(a)

(b)

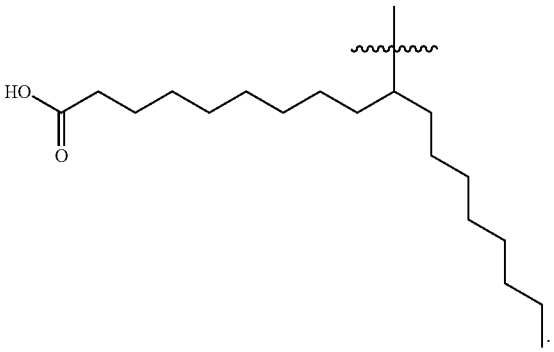

5. The compound of claim 4, wherein i is 1 and compound is represented by Structural Formula IV Structural Formula IV

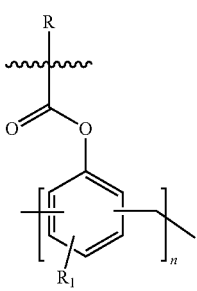

.

6. The compound of claim 3, wherein $R_1$ is H, $CH_3$, $OCH_3$, or a linear or branched $C_1$-$C_9$ alkyl chain.

7. A compound having Structural Formula I:

Structural Formula I

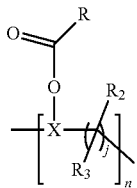

wherein:
X is

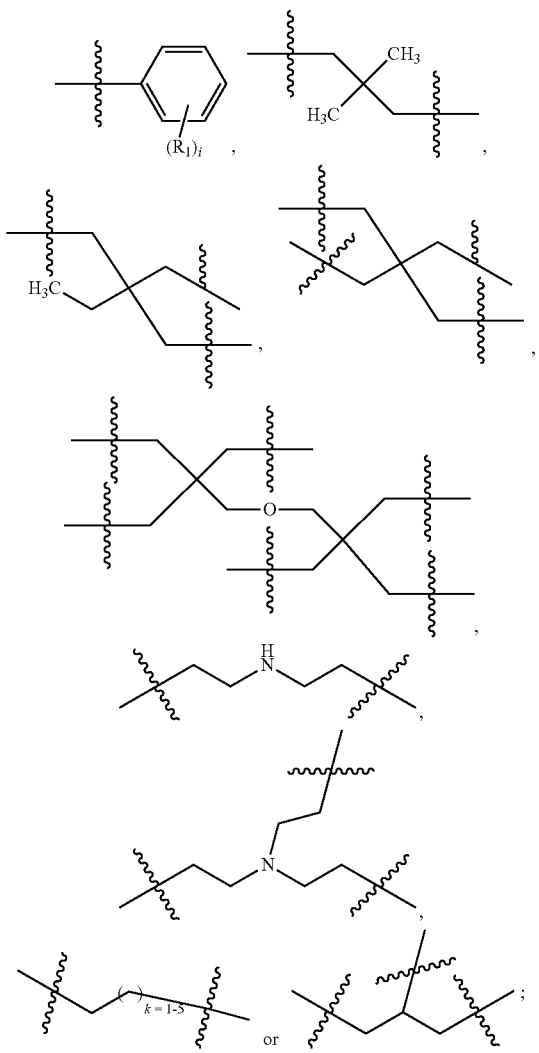

each $R_1$ is H, independently an optionally substituted $C_1$-$C_{20}$ alkyl group, an optionally substituted $C_1$-$C_{10}$ alkyl group, a tertiary carbon group, a methyl group, a methoxy group, an optionally substituted aryl group, an optionally substituted alkoxy group, an optionally substituted carbonyl group, an optionally substituted alkoxycarbonyl group, an optionally-substituted CH(R''')(R''''COOH) wherein each R''' independently is a $C_1$-$C_{10}$ linear or branched alkyl chain, or an optionally substituted carbocyclic or heterocyclic non-aromatic ring;
i=0, 1, 2, 3;
j=0 or 1;
n is an integer from 1 to 1000;
and wherein,
when n=1, then j=0; and
when n>1 then j=1,
each $R_2$ and $R_3$ is independently H, a $C_1$-$C_8$ linear or branched or cyclic alkyl chain, an optionally substituted $C_1$-$C_{20}$ alkyl group, an optionally substituted $C_1$-$C_{10}$ alkyl group, a tertiary carbon group, a methyl group, a methoxy group, an optionally substituted aryl group, and optionally substituted alkoxy group, an optionally substituted carbonyl group, an optionally substituted alkoxycarbonyl group, or —CH(R''')(R''''COOH),
R is an alkenyl chain represented by (1)

(2)

(3)

(4)

(5)

(6)

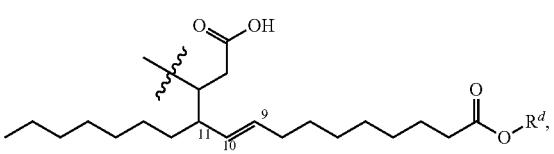

-continued

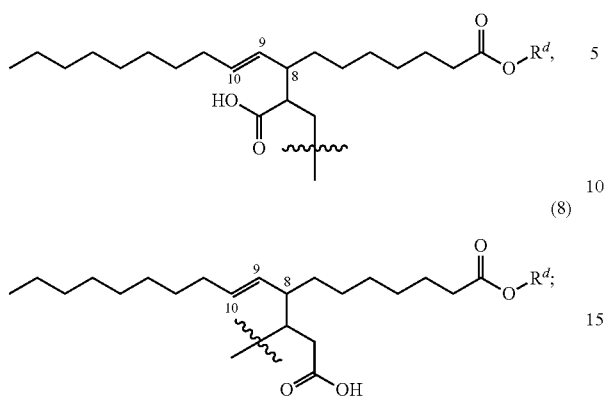

and each $R^d$ is a $C_1$-$C_{24}$ alkyl chain.

8. The compound of claim 7 wherein n=1, j=0, and the compound is represented by:

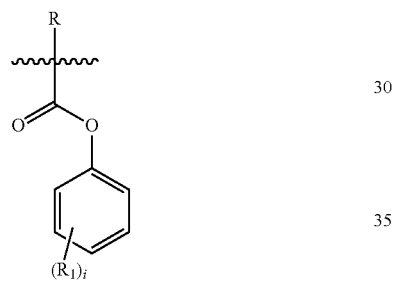

; and
wherein $R_1$ is selected from the group consisting of

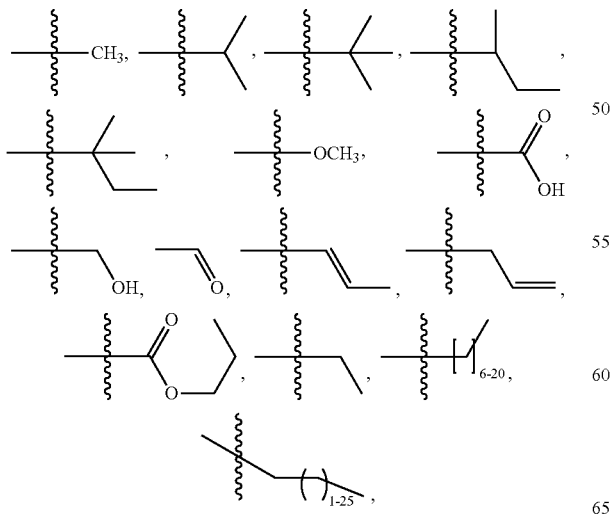

or an alkyl acid chain (a) or (b) as shown below:

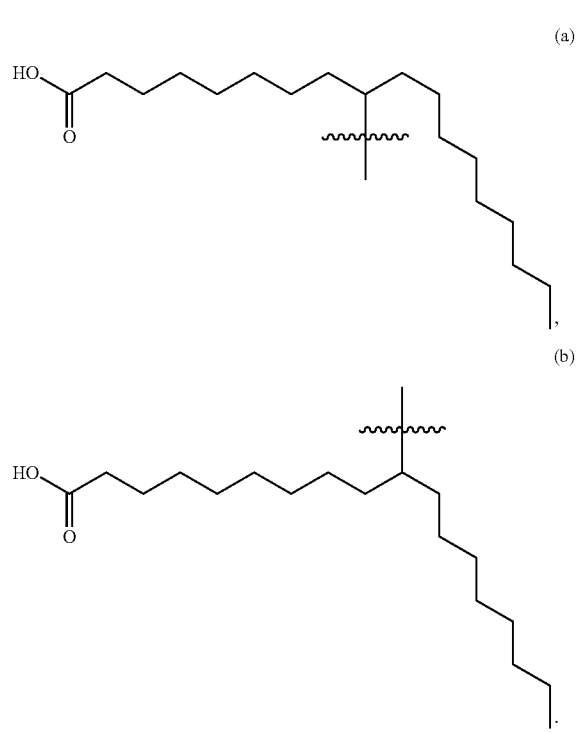

9. The compound of claim 7, wherein
i=1; and
$R_1$ is H, $CH_3$, $OCH_3$, or a linear or branched $C_1$-$C_{12}$ alkyl chain.

10. The compound of claim 7, wherein:
n=1;
j=0; and
R is a structure of

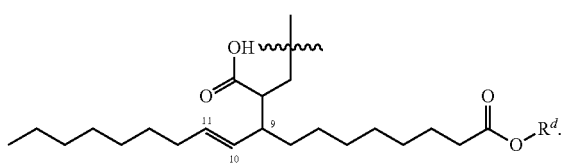

11. The compound of claim 3, wherein:
X is

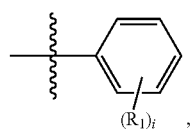

and the compound is represented by structural Formula II:

Structural Formula II

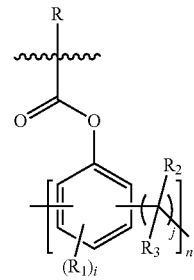

wherein:
each $R_2$, $R_3$ independently is H, methyl, or a $C_1$-$C_8$ linear or branched or cyclic alkyl chain.

12. The compound of claim 11, wherein each $R_2$, $R_3$ is H and j=1, wherein the compound structure is represented by Structural Formula III:

Structural Formula III

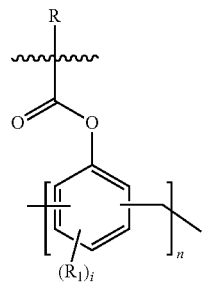

wherein,
$R_1$ is selected from the group consisting of

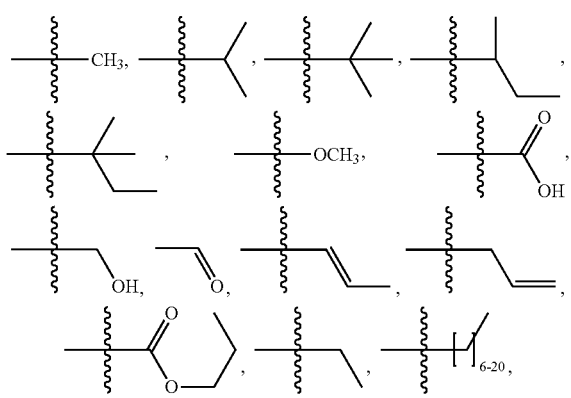

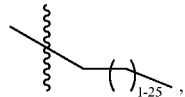

alkyl acid chain as shown below

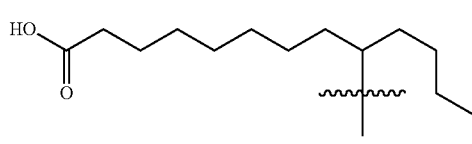

(a)

(b)

13. The compound of claim 12, wherein i is 1 and compound is represented by

Structural Formula IV

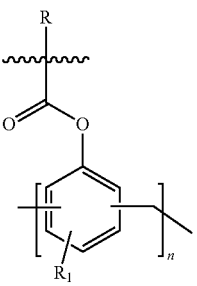

14. The compound of claim 7, wherein $R_1$ is H, $CH_3$, $OCH_3$, or a linear or branched $C_1$-$C_9$ alkyl chain.

* * * * *